(12) United States Patent
Bannister et al.

(10) Patent No.: US 10,143,671 B2
(45) Date of Patent: *Dec. 4, 2018

(54) SOLID SOLUTION COMPOSITIONS AND USE IN CHRONIC INFLAMMATION

(71) Applicant: Infirst Healthcare Limited, London (GB)

(72) Inventors: Robin M. Bannister, Essex (GB); John Brew, Hertfordshire (GB); Richard R. Reiley, III, London (GB); Wilson Caparros Wanderley, Buckinghamshire (GB)

(73) Assignee: Infirst Healthcare Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/794,214

(22) Filed: Oct. 26, 2017

(65) Prior Publication Data

US 2018/0042877 A1 Feb. 15, 2018

Related U.S. Application Data

(63) Continuation of application No. 15/195,623, filed on Jun. 28, 2016, now Pat. No. 9,827,215, which is a continuation of application No. 15/061,661, filed on Mar. 4, 2016, now Pat. No. 9,775,820, which is a continuation of application No. 14/155,108, filed on Jan. 14, 2014, now Pat. No. 9,308,213, which is a continuation-in-part of application No. 13/365,824, filed on Feb. 3, 2012, now Pat. No. 8,895,536, which is a continuation-in-part of application No. PCT/GB2011/052115, filed on Oct. 31, 2011, said application No. 14/155,108 is a continuation-in-part of application No. 13/365,828, filed on Feb. 3, 2012, now Pat. No. 8,895,537, which is a continuation-in-part of application No. PCT/GB2011/052115, filed on Oct. 31, 2011.

(60) Provisional application No. 61/752,309, filed on Feb. 4, 2013, provisional application No. 61/752,356, filed on Jan. 14, 2013.

(30) Foreign Application Priority Data

| Oct. 29, 2010 | (GB) | .................................. | 1018289.7 |
| Feb. 4, 2011 | (GB) | .................................. | 1101937.9 |
| Aug. 10, 2011 | (GB) | .................................. | 1113728.8 |
| Aug. 10, 2011 | (GB) | .................................. | 1113729.6 |
| Aug. 10, 2011 | (GB) | .................................. | 1113730.4 |

(51) Int. Cl.
| *A61K 31/192* | (2006.01) |
| *A61K 31/616* | (2006.01) |
| *A61K 9/08* | (2006.01) |
| *A61K 47/44* | (2017.01) |
| *A61K 9/20* | (2006.01) |
| *A61K 31/60* | (2006.01) |
| *A61K 47/10* | (2017.01) |
| *A61K 47/14* | (2017.01) |
| *A61K 47/22* | (2006.01) |
| *A61K 31/121* | (2006.01) |
| *A61K 31/196* | (2006.01) |
| *A61K 31/12* | (2006.01) |
| *A61K 31/25* | (2006.01) |
| *A61K 31/704* | (2006.01) |
| *A61K 31/337* | (2006.01) |
| *A61K 31/202* | (2006.01) |
| *A61K 31/201* | (2006.01) |

(52) U.S. Cl.
CPC .............. *A61K 31/192* (2013.01); *A61K 9/08* (2013.01); *A61K 9/2013* (2013.01); *A61K 31/12* (2013.01); *A61K 31/121* (2013.01); *A61K 31/196* (2013.01); *A61K 31/60* (2013.01); *A61K 31/616* (2013.01); *A61K 47/10* (2013.01); *A61K 47/14* (2013.01); *A61K 47/22* (2013.01); *A61K 47/44* (2013.01); *A61K 31/201* (2013.01); *A61K 31/202* (2013.01); *A61K 31/25* (2013.01); *A61K 31/337* (2013.01); *A61K 31/704* (2013.01); *Y02A 50/411* (2018.01)

(58) Field of Classification Search
CPC ..................................................... A61K 31/192
USPC ................................................... 514/159, 570
See application file for complete search history.

(56) References Cited

U.S. PATENT DOCUMENTS

| 3,228,831 A | 1/1966 | Nicholson et al. |
| 3,800,038 A | 3/1974 | Rudel |
| 4,571,400 A | 2/1986 | Arnold |
| 4,684,666 A | 8/1987 | Haas |
| 4,918,103 A | 4/1990 | Park et al. |

(Continued)

FOREIGN PATENT DOCUMENTS

| CN | 1736369 A | 2/2006 |
| CN | 101129335 A | 2/2008 |

(Continued)

OTHER PUBLICATIONS

Marchd et al. CAS: 144: 198910, 2006.*

(Continued)

*Primary Examiner* — Rei Tsang Shiao

(74) *Attorney, Agent, or Firm* — UltimatEdge Law Group, P.C.; Dean G. Stathakis

(57) ABSTRACT

The present specification discloses pharmaceutical compositions, methods of preparing such pharmaceutical compositions, and methods and uses of treating a chronic inflammation and/or an inflammatory disease in an individual using such pharmaceutical compositions.

26 Claims, 10 Drawing Sheets

(56) References Cited

U.S. PATENT DOCUMENTS

| | | |
|---|---|---|
| 5,011,852 A | 4/1991 | Park et al. |
| 5,059,626 A | 10/1991 | Park et al. |
| 5,154,930 A | 10/1992 | Popescu |
| 5,210,099 A * | 5/1993 | Mody ................. A61K 9/0014 514/557 |
| 5,256,699 A | 10/1993 | Murphy et al. |
| 5,445,822 A * | 8/1995 | Bracco ................. A61K 8/375 424/400 |
| 5,527,545 A | 6/1996 | Santus et al. |
| 5,552,160 A | 9/1996 | Liversidge et al. |
| 5,645,856 A | 7/1997 | Lacy et al. |
| 5,955,451 A | 9/1999 | Lichtenberger et al. |
| 6,214,386 B1 | 4/2001 | Santus |
| 6,264,981 B1 | 7/2001 | Zhang |
| 6,267,985 B1 | 7/2001 | Chen et al. |
| 6,294,192 B1 | 9/2001 | Patel et al. |
| 6,319,513 B1 | 11/2001 | Dobrozsi |
| 6,383,471 B1 | 5/2002 | Chen et al. |
| 6,451,339 B2 | 9/2002 | Patel et al. |
| 6,455,067 B1 * | 9/2002 | Woo ................. A61K 9/7053 424/449 |
| 6,923,988 B2 | 8/2005 | Patel et al. |
| 7,473,432 B2 | 1/2009 | Cevc et al. |
| 8,663,692 B1 | 5/2014 | Muller et al. |
| 8,895,536 B2 | 11/2014 | Bannister et al. |
| 8,895,537 B2 | 11/2014 | Bannister et al. |
| 9,265,742 B2 | 2/2016 | Bannister et al. |
| 9,271,950 B2 | 3/2016 | Bannister et al. |
| 9,308,213 B2 | 4/2016 | Bannister et al. |
| 9,326,958 B2 | 5/2016 | Bannister et al. |
| 9,381,180 B2 | 7/2016 | Bannister et al. |
| 9,427,422 B2 | 8/2016 | Bannister et al. |
| 9,504,664 B2 | 11/2016 | Bannister et al. |
| 9,693,980 B2 | 7/2017 | Bannister et al. |
| 9,737,500 B2 | 8/2017 | Bannister et al. |
| 9,744,132 B2 | 8/2017 | Bannister et al. |
| 9,750,810 B2 | 9/2017 | Bannister et al. |
| 9,775,820 B2 | 10/2017 | Bannister et al. |
| 9,789,075 B2 | 10/2017 | Bannister et al. |
| 9,795,577 B2 | 10/2017 | Bannister et al. |
| 9,820,952 B2 | 11/2017 | Bannister et al. |
| 9,827,215 B2 | 11/2017 | Bannister et al. |
| 2001/0005726 A1 | 6/2001 | Woo et al. |
| 2001/0006650 A1 | 7/2001 | Burnside et al. |
| 2003/0008003 A1 | 1/2003 | Jamali |
| 2003/0170279 A1 | 9/2003 | Lambert et al. |
| 2003/0232097 A1 | 12/2003 | Radhakrishnan et al. |
| 2004/0024057 A1 | 2/2004 | Earl et al. |
| 2004/0253276 A1 | 12/2004 | Sato et al. |
| 2005/0152968 A1 | 7/2005 | Brophy et al. |
| 2006/0034937 A1 | 2/2006 | Patel |
| 2006/0062810 A1 | 3/2006 | Woo et al. |
| 2006/0078616 A1 | 4/2006 | Georgewill et al. |
| 2007/0015834 A1 | 1/2007 | Flashner-Barak et al. |
| 2007/0026062 A1 | 2/2007 | Holm et al. |
| 2007/0036831 A1 | 2/2007 | Baker |
| 2007/0048284 A1 | 3/2007 | Donahue et al. |
| 2007/0048384 A1 | 3/2007 | Rosenberg et al. |
| 2007/0092559 A1 | 4/2007 | Yuan |
| 2007/0104741 A1 | 5/2007 | Murty et al. |
| 2007/0105912 A1 | 5/2007 | Holm et al. |
| 2007/0190080 A1 | 8/2007 | Friedman |
| 2007/0203173 A1 | 8/2007 | Mudumba et al. |
| 2008/0153894 A1 | 6/2008 | Britten et al. |
| 2008/0154210 A1 | 6/2008 | Jordan et al. |
| 2009/0130029 A1 | 5/2009 | Tamarkin et al. |
| 2009/0304782 A1 | 12/2009 | De Blas et al. |
| 2010/0068276 A1 | 3/2010 | Friesen et al. |
| 2010/0099767 A1 | 4/2010 | Davis |
| 2010/0125060 A1 | 5/2010 | Razzak et al. |
| 2011/0142945 A1 | 6/2011 | Chen et al. |
| 2011/0195993 A1 | 8/2011 | Masson et al. |
| 2012/0270845 A1 | 10/2012 | Bannister et al. |
| 2012/0270899 A1 | 10/2012 | Bannister et al. |
| 2013/0156853 A1 | 6/2013 | Zhang et al. |
| 2013/0178448 A1 | 7/2013 | Bannister et al. |
| 2014/0128353 A1 | 5/2014 | Bannister et al. |
| 2014/0162987 A1 | 6/2014 | Bannister et al. |
| 2014/0162988 A1 | 6/2014 | Bannister et al. |

FOREIGN PATENT DOCUMENTS

| | | |
|---|---|---|
| CN | 102793628 A | 11/2012 |
| EP | 306060 A2 | 3/1989 |
| EP | 0521344 A2 | 1/1993 |
| EP | 1923060 A1 | 5/2008 |
| EP | 1352638 B1 | 5/2009 |
| FR | 2810243 A1 | 12/2001 |
| GB | 2331458 A | 5/1999 |
| GB | 2477590 A | 8/2011 |
| JP | 6009381 A | 3/1992 |
| JP | 2008143807 A | 12/2006 |
| JP | 2009155282 A | 7/2009 |
| WO | 1986000802 A1 | 2/1986 |
| WO | 1992009272 A1 | 6/1992 |
| WO | 1995011039 A1 | 4/1995 |
| WO | 1997003655 A1 | 2/1997 |
| WO | 1998000169 A1 | 1/1998 |
| WO | 1998025595 A2 | 6/1998 |
| WO | 1999006024 A1 | 2/1999 |
| WO | 1999021534 A1 | 5/1999 |
| WO | 2000027372 A1 | 5/2000 |
| WO | 2000057859 A1 | 5/2000 |
| WO | 2000067728 A2 | 11/2000 |
| WO | 2000076478 A1 | 12/2000 |
| WO | 2002085414 A2 | 10/2002 |
| WO | 2003013566 A1 | 2/2003 |
| WO | 2004082588 A2 | 9/2004 |
| WO | 2005009436 A1 | 2/2005 |
| WO | 2005079752 A2 | 9/2005 |
| WO | 2005087194 A1 | 9/2005 |
| WO | 2006037348 A1 | 4/2006 |
| WO | 2006057903 A2 | 6/2006 |
| WO | 2006096806 A2 | 9/2006 |
| WO | 2006099325 A2 | 9/2006 |
| WO | 2006115463 A1 | 11/2006 |
| WO | 2007138339 A2 | 12/2007 |
| WO | 2008002121 A2 | 1/2008 |
| WO | 2008070950 A1 | 6/2008 |
| WO | 2008120207 A3 | 10/2008 |
| WO | 2008134512 A1 | 11/2008 |
| WO | 2009033131 A2 | 3/2009 |
| WO | 2009047785 A3 | 4/2009 |
| WO | 2009067734 A1 | 6/2009 |
| WO | 2009069139 A1 | 6/2009 |
| WO | 2010059717 A2 | 5/2010 |
| WO | 2010087947 A2 | 8/2010 |
| WO | 2010097332 A1 | 9/2010 |
| WO | 2010097334 A1 | 9/2010 |
| WO | 2010103312 A1 | 9/2010 |
| WO | 2011095814 A1 | 8/2011 |
| WO | 2012056251 A1 | 5/2012 |
| WO | 2012104654 A1 | 8/2012 |
| WO | 2012104655 A2 | 8/2012 |
| WO | 2012127037 A2 | 9/2012 |
| WO | 2014108569 A1 | 7/2014 |
| WO | 2014108572 A1 | 7/2014 |
| WO | 2014108573 A1 | 7/2014 |
| WO | 2014108574 A1 | 7/2014 |
| WO | 2014117999 A1 | 8/2014 |
| WO | 2017025517 A1 | 2/2017 |

OTHER PUBLICATIONS

Sigma-Aldrich (Millipore Sigma), Surfactants Classified by HLB Numbers, URL: https://www.sigmaaldrich.com/materials-science/material-science-products.html?TablePage=22686648, pp. 4 (downloaded Oct. 30, 2017).

Sinha, et al., Solid Dispersion as an Approach for Bioavailability Enhancement of Poorly Water-Soluble Drugs Ritonavir, AAPS Pharm. Sci. Tech. 11(2): 518-527 (2010).

Strickley, Solubilizing Excipients in Oral and Inkectable Formulations, Pharma. Res. 21: 201-230 (2004).

(56) References Cited

OTHER PUBLICATIONS

Vane, et al., Mechanism of Action of Anti-Inflammatory Drugs, Int. J. Tissue React. 20(1): 3-15 (1998). Abstract Only.
Welch, Holme & Clark Co., Inc., Partially Hydrogenated Soybean Oil, (Retrieved from Internet <URL:http://whc-oils.com/hydrogenated-soybean-oil_html>), pp. 2 (downloaded May 8, 2015).
Wikipedia, Monoglyceride, URL: https://en.wikipedia.org/wiki/Monoglyceride, pp. 3 (last edited Oct. 15, 2017).
Zeberg-Mikkelsen, et al., Predicting the Melting Points and the Enthalpies of Fusion of Saturated Triglycerides by a Group Contribution Method, Fluid Phase Equilibria 162: 7-17 (1999).
Monomuls® 90-L 12, Personal Care BASF, Product Details, URL: http://www.personalcare.basf.com/ProductDetails?PRD=30527768, pp. 4 (downloaded May 4, 2015).
Chung, et al., Oil Components Modulate Physical Characteristics and Function of the Natural Oil Emulsions as Drug or Gene Delivery System, J. Controlled Rel. 71: 339-350 (2001).
Csizmazia, E., et al., Penetration Enhancer Effect of Sucrose Laurate and Transcutol on Ibuprofen, J. Drug Del. Sci. Tech. 21(5): (2011).
Department of Health and Human Services, Attachment 3: Stability Background and Data Presentation, pp. 8 (downloaded Jan. 15, 2015).
Elburg Global, Hydrogenated Coconut Oil, URL: http://www.elburgglobal.nl/fileadmin/brochures/PDS_Hydr._Coconut_oil.pdf, p. 1, (downloaded Aug. 4, 2010).
Gattefosse, Maisine 35-1, Physicochemical Data Sheet (PCS), pp. 2 (last updated Nov. 28, 2013).
Gattefosse, Range of Products, URL: https://www.gattefosse.com/range-of-products#oral, pp. 5 (downloaded Jun. 22, 2017).
Grebe, et al., A Multicenter, Randomized, Double-Blind, Double-Dummy, Placebo- and Active-Controlled, Parallel-Group Comparison of Diclofenac-K and Ibuprofen for the Treatment of Adults with Influenza-like Symptoms, Clin. Ther. 25(2): 444-459 (2003).
Haw, The HLB System, A Time Saving Guide to Surfactant Selection, Presentation to the Midwest Chapter of the Society of Cosmetic Chemists, Uniqema, URL: http://www.lotioncrafter.com/pdf/The_HLB_System.pdf, pp. 40 (2004).
Herbarie, Emulsifiers with HLB Values, URL: http://www.theherbarie.com/files/resource-center/formulating/Emulsifiers_HLB_Values.pdf, pp. 3 (downloaded Oct. 30, 2017).
ICI Americas, Inc., The HLB System, A Time-Saving Guide to Emulsifer Selection, pp. 22 (1980).
Jain, et al., Development of Gelucire 43/01 Beads od Metformin Hydrochloride for Floating Delivery, AAPS Pharm. Sci. Tech. 10(4): 1128-1136 (2009).
Juarez-Soberanez, et al., Gelucire 39/01 as Excipient Gastroretentive Metronidazole Sustained Delivery, Int. J. Pharm. Pharm. Sci. 3(2): 86-91 (2011).
Khatri, Home Remedies for Ulcers, URL: http://www.steadyhealth.com/articles/homeremedies-for-ulcers, pp. 4 (downloaded Jun. 20, 2017).
List, et al., Hydrogenation of Soybean Oil Triglycerides: Effect of Pressure on Selectivity. JAOCS 77: 311-314 (2000).
Monzir-Pal, Characteristics of Surfactants and Emulsions, URL: http://www.monzirpal.net/Industrial/Characteristics%20of%20Surfactants%20and%20Emulsions.htm, pp. 8 (downloaded Jul. 26, 2015).
PCT Form ISA 210, International Search Report, PCT/GB2011/050189, pp. 7 (dated Jul. 1, 2011).
PCT Form ISA 237, Written Opinion, PCT/GB2011/050189, pp. 10 (dated Jul. 1, 2011).
PCT Form IB 373, International Preliminary Report on Patentability, PCT/GB2011/050189, pp. 11 (dated Aug. 7, 2012).
PCT Form ISA 210, International Search Report, PCT/GB2011/052115, pp. 4 (dated Feb. 13, 2011).
PCT Form ISA 237, Written Opinion, PCT/GB2011/052115, pp. 7 (dated Feb. 13, 2011).
PCT Form IB 373, International Preliminary Report on Patentability, PCT/GB2011/052115, pp. 8 (dated Apr. 30, 2013).
PCT Form ISA 210, International Search Report, PCT/GB2012/050241, pp. 6 (dated Jul. 13, 2012).
PCT Form ISA 237, Written Opinion, PCT/GB2012/050241, pp. 10 (dated Jul. 13, 2012).
PCT Form IB 373, International Preliminary Report on Patentability, PCT/GB2012/050241, pp. 11 (dated Aug. 6, 2013).
PCT Form ISA 210, International Search Report, PCT/GB2012/050242, pp. 7 (dated Jan. 22, 2013).
PCT Form ISA 237, Written Opinion, PCT/GB2012/050242, pp. 12 (dated Jan. 22, 2013).
PCT Form IB 373, International Preliminary Report on Patentability, PCT/GB2012/050242, pp. 12 (dated Aug. 6, 2013).
PCT Form ISA 210, International Search Report, PCT/EP2014/050627, pp. 6 (dated Apr. 25, 2014).
PCT Form ISA 237, Written Opinion, PCT/EP2014/050627, pp. 7 (dated Apr. 25, 2014).
PCT Form IB 373, International Preliminary Report on Patentability, PCT/EP2014/050627, pp. 7 (dated Aug. 4, 2015).
PCT Form ISA 210, International Search Report, PCT/EP2014/050628, pp. 3 (dated Apr. 25, 2014).
PCT Form ISA 237, Written Opinion, PCT/EP2014/050628, pp. 5 (dated Apr. 25, 2014).
PCT Form IB 373, International Preliminary Report on Patentability, PCT/EP2014/050628, pp. 7 (dated Jul. 1, 2015).
PCT Form ISA 210, International Search Report, PCT/EP2014/050636, pp. 4 (dated Apr. 3, 2014).
PCT Form ISA 237, Written Opinion, PCT/EP2014/050636, pp. 6 (dated Apr. 3, 2014).
PCT Form IB 373, International Preliminary Report on Patentability, PCT/EP2014/050636, pp. 7 (dated Jul. 14, 2015).
PCT Form ISA 210, International Search Report, PCT/EP2014/050637, pp. 4 (dated May 22, 2014).
PCT Form ISA 237, Written Opinion, PCT/EP2014/050637, pp. 6 (dated May 22, 2014).
PCT Form IB 373, International Preliminary Report on Patentability, PCT/EP2014/050637, pp. 25 (dated Apr. 8, 2015).
PCT Form ISA 210, International Search Report, PCT/EP2014/050638, pp. 4 (dated Apr. 3, 2014).
PCT Form ISA 237, Written Opinion, PCT/EP2014/050638, pp. 6 (dated Apr. 3, 2014).
PCT Form IB 373, International Preliminary Report on Patentability, PCT/EP2014/050638, pp. 7 (dated Jul. 14, 2015).
PCT Form ISA 210, International Search Report, PCT/EP2016/068900, pp. 3 (dated Oct. 26, 2016).
PCT Form ISA 237, Written Opinion, PCT/EP2016/068900, pp. 6 (dated Oct. 26, 2016).
PubChem, 1-Linoleoyl-(2S)-glycerol, URL: https://pubchem.ncbi.nlm.nih.gov/compound/6436630, pp. 20 (last modified Nov. 4, 2017).
PubChem, 1-Monolinolein, URL: https://pubchem.ncbi.nlm.nih.gov/compound/1-Monolinolein, pp. 20 (last modified Nov. 4, 2017).
Ren, et al., Optimization of Self Nanoemulsifying Drug Delivery System for Poorly Water-Soluble Drug using Response Surface Methodology, Drug. Dev. Ind. Pharm. 39(5): 799-806 (2013).
Sharma, et al., Preparation and Characterization of Meloxicam-Myrj-52 Granules Obtained by Melt Granulation, PharmaTech, URL: http://www.pharmtech.com/node/230107?rel=canonical, pp. 7 (2007).
Shen, et al., Effects of Core Tablet Size on the Functionality of Aqueous Delayed Release Coatings as Measured by SEM and LIBS, ACRYL-EZE MP, Poster Reprint (2010).
U.S. Appl. No. 13/365,824, filed Feb. 3, 2012, Feb. 4, 2011, US 20120270845, U.S. Pat. No. 8,895,536.
U.S. Appl. No. 13/365,828, filed Feb. 3, 2012, Feb. 4, 2011, US 20120270899, U.S. Pat. No. 8,895,537.
U.S. Appl. No. 13/576,758, filed Dec. 14, 2012, Feb. 5, 2010, US 20130178448.
U.S. Appl. No. 14/155,042, filed Jan. 14, 2014, Feb. 4, 2011, US 20140155485, U.S. Pat. No. 9,271,950.
U.S. Appl. No. 14/155,080, filed Jan.14, 2014, Feb. 4, 2011, US 20140128354, U.S. Pat. No. 9,265,742.
U.S. Appl. No. 14/155,108, filed Jan. 14, 2014, Feb. 4, 2011, US 20140162988, U.S. Pat. No. 9,308,213.

(56) References Cited

OTHER PUBLICATIONS

U.S. Appl. No. 14/155,147, filed Jan. 14, 2014, Feb. 4, 2011, US 20140128353.
U.S. Appl. No. 14/155,167, filed Jan. 14, 2014, Feb. 4, 2011, US 20140162987.
U.S. Appl. No. 14/520,141, filed Oct. 21, 2014, Feb. 4, 2011, US 20150051281, U.S. Pat. No. 9,326,958.
U.S. Appl. No. 14/520,150, filed Oct. 21, 2014, Feb. 4, 2011, US 20150051287, U.S. Pat. No. 9,381,180.
U.S. Appl. No. 14/520,159, filed Oct. 21, 2014, Feb. 4, 2011, US 20150051235, U.S. Pat. No. 9,427,422.
U.S. Appl. No. 14/821,687, filed Aug. 7, 2015, Feb. 4, 2011, US 20150342880, U.S. Pat. No. 9,744,132.
U.S. Appl. No. 14/975,599, filed Dec. 18, 2015, Feb. 4, 2011, US 20160101077, U.S. Pat. No. 9,504,664.
U.S. Appl. No. 14/975,608, filed Dec. 18, 2015, Feb. 4, 2011, US 20160101180, U.S. Pat. No. 9,737,500.
U.S. Appl. No. 15/043,327, filed Feb. 12, 2016, Feb. 4, 2011, US 20160158361.
U.S. Appl. No. 15/061,661, filed Jan. 14, 2014, Feb. 4, 2011, US 20160199327.
U.S. Appl. No. 15/169,617, filed May 31, 2016, Feb. 4, 2011, US 20160271087, U.S. Pat. No. 9,693,980.
U.S. Appl. No. 15/169,619, filed May 31, 2016, Feb. 4, 2011, US 20160271088.
U.S. Appl. No. 15/195,608, filed Jun. 28, 2016, Feb. 4, 2011, US 20160303060.
U.S. Appl. No. 15/195,623, filed Jun. 28, 2016, Feb. 4, 2011, US 20160317482.
U.S. Appl. No. 15/219,245, filed Jul. 25, 2016, Feb. 4, 2011, US 20160331706, U.S. Pat. No. 9,789,075.
U.S. Appl. No. 15/289,083, filed Oct. 7, 2016, Feb. 4, 2011, US 20170043016.
U.S. Appl. No. 15/295,933, filed Oct. 17, 2016, Feb. 4, 2011, US 20170027895, U.S. Pat. No. 9,795,577.
U.S. Appl. No. 15/614,592, filed Jun. 5, 2017, Feb. 4, 2011, US 20170266287.
U.S. Appl. No. 15/684,197, filed Aug. 23, 2017, Feb. 4, 2011, US 20170348262.
U.S. Appl. No. 15/684,214, filed Aug. 23, 2017, Feb. 4, 2011, US 20170360702.
U.S. Appl. No. 15/702,440, filed Sep. 12, 2017, Feb. 4, 2011, US 20180000763.
U.S. Appl. No. 15/794,178, filed Oct. 26, 2017, Feb. 4, 2011.
U.S. Appl. No. 15/794,197, filed Oct. 26, 2017, Feb. 4, 2011.
U.S. Appl. No. 15/794,214, filed Oct. 26, 2017, Feb. 4, 2011.
PCT Form IB 373, International Preliminary Report on Patentability, PCT/EP2016/068900, pp. 7 (Feb. 22, 2018).
Karatas, et al., Improved Solubility and Dissolution Rate of Piroxicam Using Gelucire 44/14 and Labrasol, II Farmaco 60: 777-782 (2005).

* cited by examiner

SOLID SOLUTION COMPOSITIONS AND USE IN CHRONIC INFLAMMATION

This continuation claims the benefit of priority pursuant to 35 U.S.C. § 120 to U.S. Non-Provisional patent application Ser. No. 15/195,623, filed Jun. 28, 2016, a continuation that claims priority to U.S. Non-Provisional patent application Ser. No. 15/061,661, filed Mar. 4, 2016, a continuation that claims priority to U.S. Non-Provisional patent application Ser. No. 14/155,108, filed Jan. 14, 2014, now U.S. Pat. No. 9,308,213, a continuation-in-part application that claims priority to U.S. patent application Ser. No. 13/365,824, filed Feb. 3, 2012, a continuation-in-part application that claims priority to patent application PCT/GB2011/052115, filed Oct. 31, 2011, an international patent application that claims priority to GB 1018289.7, filed Oct. 29, 2010; and U.S. Non-Provisional patent application Ser. No. 14/155,108, filed Jan. 14, 2014, now U.S. Pat. No. 9,308,213, a continuation-in-part application that claims priority to U.S. patent application Ser. No. 13/365,828, filed Feb. 3, 2012, a continuation-in-part application that claims priority to patent application PCT/GB2011/052115, filed Oct. 31, 2011, an international patent application that claims priority to GB 1018289.7, filed Oct. 29, 2010, and U.S. Non-Provisional patent application Ser. No. 14/155,108, filed Jan. 14, 2014, now U.S. Pat. No. 9,308,213, a continuation-in-part application that claims priority to GB 1113730.4, filed Aug. 10, 2011, GB 1113729.6, filed Aug. 10, 2011, GB 1113728.8, filed Aug. 10, 2011, and GB 1101937.9, filed Feb. 4, 2011; and U.S. Non-Provisional patent application Ser. No. 14/155,108, filed Jan. 14, 2014, now U.S. Pat. No. 9,308, 213, a continuation-in-part application that claims priority pursuant to 35 U.S.C. § 119(e) to U.S. Provisional Patent Application 61/752,309, filed Jan. 14, 2013, and U.S. Provisional Patent Application 61/752,356, filed Jan. 14, 2013, each of which is hereby incorporated by reference in its entirety.

Inflammation involves the activation of the immune system in response to harmful stimuli, such as, e.g., a pathogen, infection, irritant, or damage to cells. As a stereotyped response, inflammation is a mechanism of innate immunity, as compared to adaptive immunity, which is specific for each pathogen. Inflammation can be classified as either acute or chronic. Generally speaking, acute inflammation is mediated by granulocytes, while chronic inflammation is mediated by mononuclear cells such as monocytes and lymphocytes.

Acute inflammation is an initial protective response of the body to remove an injurious stimulus by maintaining tissue integrity and contributing to tissue repair. It a part of the body's natural defense system against injury and disease, and in the absence of acute inflammation, wounds and infections would never heal and progressive destruction of the tissue would compromise the survival of the organism.

The process of acute inflammation is initiated by cells already present in all tissues, mainly resident macrophages, dendritic cells, histiocytes, Kupffer cells, mastocytes, vascular endothelial cells, and vascular smooth muscle cells. At the onset of a harmful stimulus, these cells undergo activation and release inflammatory mediating and sensitizing molecules, such as, e.g., pro-inflammatory cytokines, pro-inflammatory prostaglandins, leukotrienes, histamine, serotonin, neutral proteases, bradykinin and nitric oxide. These inflammatory molecules modulate a complex series of biological events involving cellular and acellular components of the local vascular system, the immune system, and the injured tissue site to propagate and mature the inflammatory response. These events are responsible for eliciting an acute inflammatory response, typically characterized by 1) vasodilatation which increases blood flow into the tissue thereby causing erythema (redness and warmth), which may extend beyond this site (the flare response); 2) blood vessel permeability which increases plasma leakage into the tissue thereby causing edema (swelling); 3) alter the excitability of certain sensory neurons causing hypersensitivity and pain; 4) stimulate the release of inflammation inducing molecules such as, e.g., neuropeptides like substance P (SP) and calcitonin gene-related peptide (CGRP), prostaglandins, and amino acids like glutamate, from the peripheral nerve endings; and 5) increase migration of leukocytes, mainly granulocytes, from the blood vessels into the tissue. An acute inflammatory response requires constant stimulation to be sustained and must be actively terminated when no longer needed. Hence, acute inflammation ceases once the injurious stimulus has been removed.

However, severe or prolonged noxious stimulation results in a chronic inflammatory response that leads to a progressive shift in the type of cells present at the site of tissue injury. Chronic inflammation may be characterized as the simultaneous destruction and healing of tissue from the inflammatory process, with the net result of provoking injury rather than mediating repair. As such, chronic inflammation is a disease. As an inflammatory response can occur anywhere in the body, chronic inflammation has been implicated in the pathophysiology of a wide range of seemingly unrelated disorders which underlay a large and varied group of human diseases. For example, chronic inflammation is involved in diseases as diverse as cardiovascular diseases, cancers, allergies, obesity, diabetes, digestive system diseases, degenerative diseases, auto-immune disorders, and Alzheimer's disease.

Attempts to treat chronic inflammation have met with limited success. This is due, in part, to the fact that the etiology of chronic inflammation is a complex response based in part on the various inflammation inducing molecules and the multitude of inflammation mediating and sensitizing molecules that appear to elicit inflammation via redundant mechanism. In addition, besides blocking pro-inflammatory molecules, many anti-inflammatory drugs, also inhibit regulatory loops that release endogenous anti-inflammatory molecules. For example, NSAIDs reduce inflammation by blocking the enzymatic activity of cyclooxygenase, a key enzyme that catalyzes the conversion of arachidonic acid to prostaglandins and leukotrienes. Thus, NSAIDs reduce inflammation by preventing the synthesis of all prostaglandins. However, NSAIDs not only prevents the synthesis of proinflammatory prostaglandins, these compounds also prevent the synthesis of anti-inflammatory prostaglandins. Hence, NSAIDs have limited success as they block endogenous anti-inflammatory response, which in some instances may prolong chronic inflammation. Therefore, compounds, compositions, uses, and methods preferentially inhibiting pro-inflammatory responses would be highly desirable for the treatment of chronic inflammation.

The present specification discloses solid solution pharmaceutical compositions. The pharmaceutical compositions disclosed herein are formulated in a manner that essentially produces a lipid-adjuvant delivery system that enables a therapeutic compound having anti-inflammatory activity to be delivered in a manner that more effectively inhibits a pro-inflammatory response. The end result is an improved treatment for chronic inflammation.

SUMMARY

Aspects of the present specification disclose, in part, a solid solution pharmaceutical composition comprising a therapeutic compound, one or more room temperature solid lipids. The solid solution pharmaceutical composition disclosed herein may further comprise one or more room temperature liquid lipids, one or more stabilizing agents, one or more neutralizing agents, or any combination thereof. A therapeutic compound may have an anti-inflammatory activity.

Other aspects of the present specification disclose, in part, a method of preparing a solid solution pharmaceutical composition disclosed herein. A method disclosed herein comprises the steps of a) contacting a therapeutic compound disclosed herein with one or more room temperature liquid lipids under conditions which allow the therapeutic compound to dissolve in the lipids; and b) contacting the compound/lipid solution with one or more room temperature solid lipids under conditions which allow the formation of a solid solution composition. In aspects of this method, heat is applied to dissolve the therapeutic compound into the one or more room temperature liquid lipids to create a solution. In other aspects of this method, step (a) comprises contacting a therapeutic compound disclosed herein with one or more room temperature liquid lipids and/or one or more stabilizing agents, and/or one or more neutralizing agents under conditions which allow the therapeutic compound to dissolve in the lipids.

Other aspects of the present specification disclose a method of treating an individual with a chronic inflammation, the method comprising the step of administering to the individual in need thereof a solid solution pharmaceutical composition disclosed herein, wherein administration results in a reduction in a symptom associated with the chronic inflammation, thereby treating the individual.

Other aspects of the present specification disclose a use of a solid solution pharmaceutical composition disclosed herein in the manufacture of a medicament for the treatment of a chronic inflammation.

Other aspects of the present specification disclose a solid solution pharmaceutical composition disclosed herein for use in the treatment of a chronic inflammation.

Other aspects of the present specification disclose a use of a solid solution pharmaceutical composition disclosed herein for the treatment of a chronic inflammation.

BRIEF DESCRIPTION OF THE DRAWINGS

FIG. 1A is a DSC graph of ibuprofen alone exhibiting a melting point range of 75° C. to 78° C.; FIG. 1B is a DSC graph of GELUCIE® 43/01 alone exhibiting a melting point range of 41° C. to 45° C.; FIG. 1C is a DSC graph of a vehicle comprising GELUCIE® 43/01, MAISINE® 35-1, and PEG 400 exhibiting a melting point ranges of 32° C. to 38° C. and 41° C. to 45° C.; FIG. 1D is a DSC graph of Ibuprofen composition LA 35-1 exhibiting a melting point range of 32° C. to 44° C.; FIG. 1E is a DSC graph of Ibuprofen composition LA 35-2 exhibiting a melting point range of 32° C. to 43° C.; FIG. 1F is a DSC graph of Ibuprofen composition LA 35-1 exhibiting a melting point range of 32° C. to 42° C.; FIG. 1G is a DSC graph of Ibuprofen composition LA 35-1 exhibiting a melting point range of 32° C. to 38° C.; FIG. 1H is a DSC graph of Ibuprofen composition LA 35-1 exhibiting a melting point range of 32° C. to 42° C.

DESCRIPTION

Figure 1A:
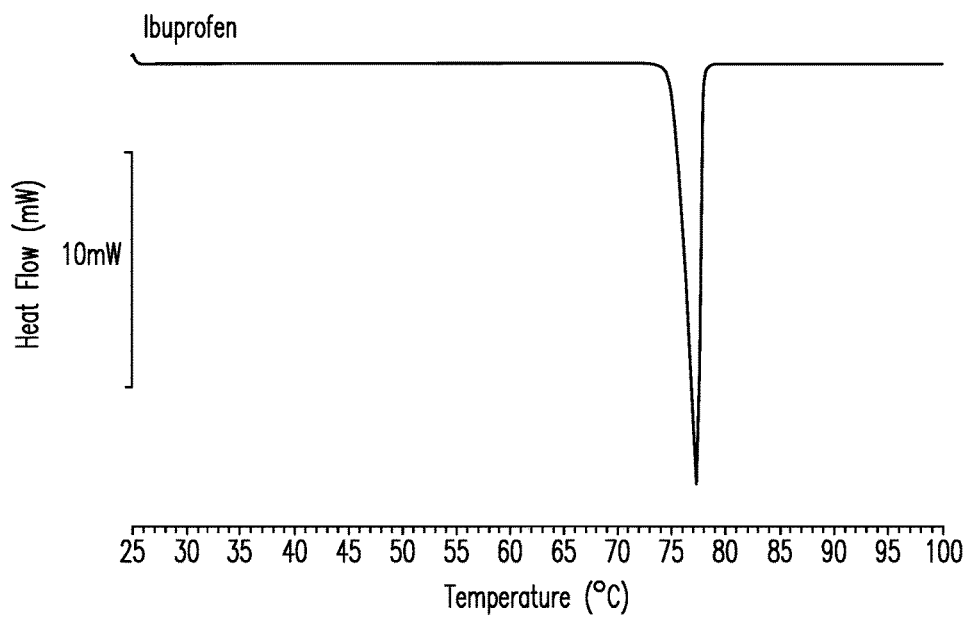
FIGS. 1A-H show differential scanning calorimetry (DSC) graphs of solid solution compositions disclosed herein comprising ibuprofen.
Figure 1B:
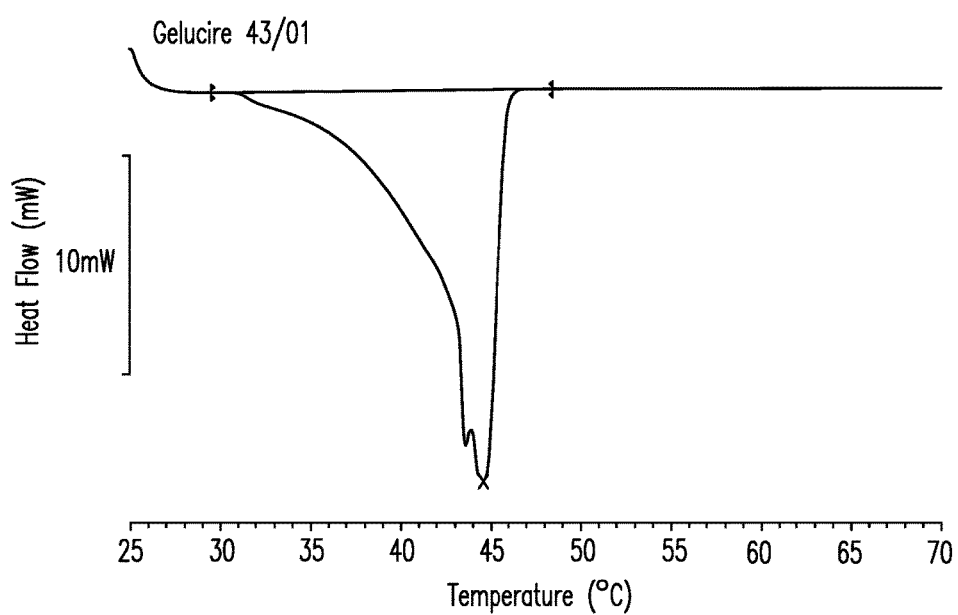

The present specification discloses solid solution compositions useful to formulate a wide variety of therapeutic compounds. Solid solution compositions are crystalline solids comprising a matrix of a solvent material (which may be solid at normal temperatures) and solutes where the molecules in the solid solution are arranged in a random fashion and not in an ordered alignment. The solid solution pharmaceutical compositions disclosed herein act as a delivery system that enable a therapeutic compound disclosed herein to be more effectively delivered or targeted to a cell type, tissue, organ, or region of the body in a manner that more effectively inhibits a pro-inflammatory response. This inhibition results in an improved treatment of a chronic inflammation.

For example, a pharmaceutical composition disclosed herein may facilitate the delivery of a therapeutic compound disclosed herein into macrophages. Macrophages exist at the crossroads of two fundamental pathways being the principle cells in the immune system and also lipid metabolism. With regards to the immune system, most pathogens have a lipid-containing surface component that macrophage recognize and then engulf the pathogen. One possible mechanism that achieves this selective biodistribution is that the pharmaceutical compositions disclosed herein may be designed to take advantage of the activity of chylomicrons. Chylomicrons are relatively large lipoprotein particles having a diameter of 75 nm to 1,200 nm. Comprising triglycerides (85-92%), phospholipids (6-12%), cholesterol (1-3%) and apolipoproteins (1-2%), chylomicrons transport dietary lipids from the intestines to other locations in the body. Chylomicrons are one of the five major groups of lipoproteins, the others being VLDL, IDL, low-density lipoproteins (LDL), high-density lipoproteins (HDL), that enable fats and cholesterol to move within the water-based solution of the bloodstream.

During digestion, fatty acids and cholesterol undergo processing in the gastrointestinal tract by the action of pancreatic juices including lipases and emulsification with bile salts to generate micelles. These micelles allow the absorption of lipid as free fatty acids by the absorptive cells of the small intestine, known as enterocytes. Once in the enterocytes, triglycerides and cholesterol are assembled into nascent chylomicrons. Nascent chylomicrons are primarily composed of triglycerides (85%) and contain some cholesterol and cholesteryl esters. The main apolipoprotein component is apolipoprotein B-48 (APOB48). These nascent chylomicrons are released by exocytosis from enterocytes into lacteals, lymphatic vessels originating in the villi of the small intestine, and are then secreted into the bloodstream at the thoracic duct's connection with the left subclavian vein.

While circulating in lymph and blood, chylomicrons exchange components with HDL. The HDL donates apolipoprotein C-II (APOC2) and apolipoprotein E (APOE) to the nascent chylomicron and thus converts it to a mature chylomicron (often referred to simply as "chylomicron"). APOC2 is the cofactor for lipoprotein lipase (LPL) activity. Once triglyceride stores are distributed, the chylomicron returns APOC2 to the HDL (but keeps APOE), and, thus, becomes a chylomicron remnant, now only 30-50 nm. APOB48 and APOE are important to identify the chylomicron remnant in the liver for endocytosis and breakdown into lipoproteins (VLDL, LDL and HDL). These lipoproteins are processed and stored by competent cells, including, e.g., hepatocytes, adipocytes and macrophages. Thus, without wishing to be limited by any theory, upon oral administration, a pharmaceutical composition disclosed herein can be processed into micelles while in the gastrointestinal tract, absorbed by enterocytes and assembled into nascent chylomicrons, remain associated with chylomicron remnants taken up by the liver, and ultimately loaded into macrophages which are present in inflamed tissues.

As another example, a pharmaceutical composition disclosed herein may facilitate the delivery of a therapeutic compound disclosed herein into dentritic cells. One possible mechanism to achieve selective biodistribution of the pharmaceutical compositions disclosed herein may be to take advantage of the endocytotic/phagocytotic activity of dentritic cells. Dendritic cells are immune cells forming part of the mammalian immune system. The main function of dendritic cells is to process antigen material and present it on the surface to other cells of the immune system. Thus, dendritic cells function as antigen-presenting cells that act as messengers between innate and adaptive immunity. Dendritic cells are present in tissues in contact with the external environment, such as, e.g., the skin (where there is a specialized dendritic cell type called Langerhans cells) and the inner lining of the nose, lungs, stomach and intestines. These cells can also be found in an immature state in the blood. Once activated, they migrate to the lymph nodes where they interact with T cells and B cells to initiate and shape the adaptive immune response. Dendritic cells are known to endocytose and phagocytose lipid particles as part of their environmental monitoring and antigen presentation processes. Without wishing to be limited by any theory, upon topical or inhalatory administration, a pharmaceutical composition disclosed herein can penetrate into the skin or inner lining of the nose, lungs, stomach and intestines, be endocytosed/phagocytosed by dendritic cells, and ultimately loaded into T cells and/or B cells which are present in inflamed tissues.

In addition to the targeted delivery of the therapeutic compound disclosed herein, a solid solution pharmaceutical composition disclosed herein take advantage of the different melting point temperatures of the various lipids used. By controlling the types and amounts of the lipids added, a pharmaceutical composition disclosed herein can be made that is substantially solid at room temperature, but melts when it reaches body temperature, such as, e.g., after being ingested. The resulting melted composition readily forms micelles which are absorbed by the intestine, assembled into chylomicrons, and ultimately absorbed by macrophages or taken up by dentritic cells as described above.

Aspects of the present specification disclose, in part, a solid solution composition. A solid solution composition disclosed herein is generally administered as a pharmaceutical acceptable composition. As used herein, the term "pharmaceutically acceptable" refers any molecular entity or composition that does not produce an adverse, allergic or other untoward or unwanted reaction when administered to an individual. As used herein, the term "pharmaceutically acceptable composition" is synonymous with "pharmaceutical composition" and means a therapeutically effective concentration of an active ingredient, such as, e.g., any of the therapeutic compounds disclosed herein. A pharmaceutical composition disclosed herein is useful for medical and veterinary applications. A pharmaceutical composition may be administered to an individual alone, or in combination with other supplementary active ingredients, agents, drugs or hormones.

To influence the pharmacodynamics of a therapeutic compound disclosed herein three features of the solid solution composition must be present. First, at least one lipid used in the solid solution composition must be made up of at least one fatty acid in which the carbon chain length is above 12 and below 24 and therefore suitable for absorption through the enterocyte pathways. Fatty acids below this $C_{12}$-$C_{24}$ length do not form a lipid-drug matrix, and thus the drug is taken up by the body by the normal absorption process. Fatty acids above this $C_{12}$-$C_{24}$ length, although forming lipid-drug matrices, cannot be absorbed and the drug leaches out of the solid solution composition and is eliminated by the body via the gastrointestinal tract.

Second, the therapeutic compound itself should have a lipohilicity that allows it to form a solid solution matric with the $C_{12}$-$C_{24}$ lipid. As discussed below, this lipohilicity can be inherent to the therapeutic compound (lipid-soluble drug formulations), or certain additives may be used that facilitate a wider range of lipid soluble drugs in the matrix (free acid/free base drug formulations, salt drug formulations, and combination drug formulations).

Third, the therapeutic compound itself should influence the biology of certain cell types that are contacted by the lipid-adjuvant nature of a solid solution composition that ultimately circulate in the body. Such constructs include chylomicron, LDL particles and HDL particles. The cell types contacted may include macrophages, dendritic cells and adipose cells and cancer cells. Tissues that have a high surface lipid content may also be preferentially targeted. These include nerve tissues and the brain.

The present specification discloses four general types of solid solution compositions, namely lipid-soluble drug formulations, free acid/free base drug formulations, salt drug formulations, and combination drug formulations. Solid solution compositions formulated using a lipid-soluble drug formulation only require a lipid component to formulate a therapeutic compound disclosed herein into a solid solution composition. Without wishing to be limited by a theory, lipid-soluble drugs can typically be dissolved in a lipid under heat. Upon cooling it is believed that the lipid component and drug form lipid-drug matrices organized in a manner where the lipids encase the drug. Since only hydrophobic interactions are present, there is no organized alignment of these lipid-drug matrices resulting in a solid solution composition (i.e., there is no crystallization into a classic solid form).

Generally, therapeutic compounds having a log P of about 3.0 or greater are useful in a lipid-soluble drug formulation. Non-limiting examples include an Artemisinin like Arteether, Artemether, Artemisinin, Artesunate, and Dihydroartemisinin; a Fibrate like Bezafibrate, Ciprofibrate, Clofibrate, Fenofibrate, and Gemfibrozil; and a Statin like Atorvastatin, Fluvastatin, Lovastatin, Pitavastatin, Pravastatin, Rosuvastatin, and Simvastatin.

A lipid-soluble drug formulation does not use or require a surfactant. In addition, a lipid-soluble drug formulation does not use or require non-lipid based solvent.

Solid solution compositions formulated using a free acid/free base drug formulation require a stabilizing agent in addition to a lipid component to formulate a therapeutic compound disclosed herein into a solid solution composition. A therapeutic compound having a free acid or free base can dissolve in a lipid under heat, but upon cooling to room temperature will crystalize to form a classic solid composition. This occurs because the thermodynamic properties of these mixtures favor the lower energy solid phase. In order to produce a solid solution composition, a stability agent must be added to stabilize the drug and prevent its transition into a classic solid phase upon cooling. Without wishing to be limited by a theory, it is believed that the stability agent coats lipid-drug matrices upon their formation. This coating impedes interactions between matrices thereby preventing the alignments necessary to form a crystalline matrix of a solid phase composition. As such, the transition to a solid phase does not occur and a solid solution composition is formed. Thus, a stability agents is a compound that provide a barrier to the thermodynamic transition to a classic solid phase or prolongs this transition to such an extent that it does not occur. Examples of stability agents include liquid polyethylene glycols, isosorbide dimethyl ether, diethylene glycol monoethyl ether (2-(2-ethoxyethoxy)ethanol), monohydrate alcohols Generally, therapeutic compounds having a log P of about 2.2 to about 3.0 are useful in a free acid/free base drug formulation. Non-limiting examples include a non-steroidal anti-inflammatory drug (NSAID) and an ester of aminobenzoic acid. A NSAID includes a salicylate derivative NSAID, a p-amino phenol derivative NSAID, a propionic acid derivative NSAID, an acetic acid derivative NSAID, an enolic acid (Oxicam) derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor. An ester of aminobenzoic acid includes Amylocaine, Benzocaine, Butacaine, Butamben, Chloroprocaine, Dimethocaine, Lidocaine, Meprylcaine, Metabutethamine, Metabutoxycaine, Orthocaine, Prilocaine, Propoxycaine, Procaine (Novocaine), Proxymetacaine, Risocaine, and Tetracaine.

Solid solution compositions formulated using a salt drug formulation require a neutralizing agent in addition to a lipid component to formulate a therapeutic compound disclosed herein into a solid solution composition. A therapeutic compound salt can dissolve in a lipid under heat, but upon cooling to room temperature will crystalize to form a classic solid composition. This occurs because the thermodynamic properties of these mixtures favor the lower energy solid phase. In order to produce a solid solution composition, a neutralizing agent must be added to neutralize a therapeutic compound salt and prevent its transition into a classic solid phase upon cooling. Without wishing to be limited by a theory, it is believed that the neutralizing agent eliminates that charges presence in the salt drugs. This neutralization impedes the ionic interactions between matrices thereby preventing the alignments necessary to form a crystalline matrix of a solid phase composition. As such, the transition to a solid phase does not occur and a solid solution composition is formed. Thus, a neutralizing agent is a compound that provide a barrier to the thermodynamic transition to a classic solid phase or prolongs this transition to such an extent that it does not occur.

Neutralizing agents include fatty acids for base-salt drugs and triethanolamine for acid-salt drugs. The degree of neutralization depends on the amount of neutralizing agent added to the formulation. For complete neutralization, one molar equivalent of neutralizing agent is added to the formulation. For partial neutralization, less than one molar equivalent is added. Partial neutralization is advantageous in producing a sustained release formulation. Upon administration, a portion of the drug is immediately made available to the body (instant bioavailability) while the bioavailability of another portion is delayed until the neutralized by the neutralizing agent. A neutralizing agent may also be added in an excessive amount, i.e., more than one molar equivalent. Besides neutralizing the salt-drug, excessive amounts of neutralizing agent can also enable adjustments to the melting point of the solid solution composition.

Generally, therapeutic compounds having a log P of about 2.2 or less are useful in a salt drug formulation. Non-limiting examples include ryanodine receptor antagonists like Azumolene and Dantrolene; and Angiotensin II receptor antagonists like Azilsartan, Candesartan, Eprosartan, Irbesartan, Losartan, Olmesartan, Telmisartan, and Valsartan.

Solid solution compositions may also comprises different combinations of lipid-soluble drugs, free-acid/free-base drugs, and salt drugs. Depending of the drugs used, such formulations, besides the lipid component and the drug, can also include a stabilizing agent, a neutralizing agent, or both.

Aspects of the present specification disclose, in part, a therapeutic compound. A therapeutic compound is a compound that provides pharmacological activity or other direct effect in the diagnosis, cure, mitigation, treatment, or prevention of disease, or to affect the structure or any function of the body of man or animals. A therapeutic compound disclosed herein may be used in the form of a pharmaceutically acceptable salt, solvate, or solvate of a salt, e.g. the hydrochloride. Additionally, therapeutic compound disclosed herein may be provided as racemates, or as individual enantiomers, including the R- or S-enantiomer. Thus, the therapeutic compound disclosed herein may comprise a R-enantiomer only, a S-enantiomer only, or a combination of both a R-enantiomer and a S-enantiomer of a therapeutic compound. A therapeutic compound disclosed herein may have anti-inflammatory activity.

In an embodiment, a therapeutic compound disclosed herein has an anti-inflammatory activity capable of reducing the levels of an inflammation inducing molecule. In an aspect of this embodiment, a therapeutic compound disclosed herein has an anti-inflammatory activity capable of reducing the levels of substance P (SP), calcitonin gene-related peptide (CGRP), glutamate, or a combination thereof. In other aspects of this embodiment, a therapeutic compound disclosed herein has an anti-inflammatory activity capable of reducing the levels of SP, CGRP, glutamate, or a combination thereof released from a sensory neuron by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a therapeutic compound disclosed herein has an anti-inflammatory activity capable of reducing the levels of SP, CGRP, glutamate, or a combination thereof released from a sensory neuron in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

Prostaglandins mediate a local inflammatory response and are involved in all inflammatory functions through action on prostaglandin receptors and mediate inflammatory signaling including chemotaxis (macrophages, neutrophils and eosinophils), vasodilation and algesia. However, the PG-mediated inflammatory response is self-limiting (resolving). The principle resolution factor is a prostaglandin called 15dPGJ2, which is an endogenous agonist of peroxisome proliferator-activator receptor gamma (PPAR-γ) signaling. PPARγ signaling pathway 1) induces apoptosis of Macrophage M1 cells, thereby reducing the levels of Th1 pro-inflammatory cytokines and 2) promotes differentiation of monocytes into Macrophage M2 cells. Macrophage M2 cells produce and release Th2 anti-inflammatory cytokines.

In an embodiment, a therapeutic compound disclosed herein has an anti-inflammatory activity capable of reducing the levels of an inflammation inducing prostaglandin. In other aspects of this embodiment, a therapeutic compound disclosed herein has an anti-inflammatory activity capable of reducing the levels of a inflammation inducing prostaglandin released from a sensory neuron by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a therapeutic compound disclosed herein has an anti-inflammatory activity capable of reducing the levels of a inflammation inducing prostaglandin released from a sensory neuron in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another embodiment, a therapeutic compound disclosed herein has an anti-inflammatory activity substantially similar to 15dPGJ2. In aspects of this embodiment, a therapeutic compound disclosed herein an anti-inflammatory activity that is, e.g., at least 5%, at least 15%, at least 25%, at least 50%, at least 55%, at least 60%, at least 65%, at least 70%, at least 75%, at least 80%, at least 85%, at least 90% or at least 95% of the activity observed for 15dPGJ2. In other aspects of this embodiment, a therapeutic compound disclosed herein an anti-inflammatory activity that is in a range from, e.g., about 5% to about 100%, about 50% to about 100%, about 60% to about 100%, about 70% to about 100%, about 80% to about 100%, about 25% to about 90%, about 50% to about 90%, about 60% to about 90%, about 70% to about 90%, about 80% to about 90%, about 25% to about 80%, about 50% to about 80%, about 60% to about 80%, about 70% to about 80%, about 25% to about 70%, about 50% to about 70%, about 25% to about 60%, about 50% to about 60%, or about 25% to about 50% of the activity observed for 15dPGJ2.

The peroxisome proliferator-activated receptors (PPARs) are a group of nuclear receptor proteins that function as transcription factors regulating the expression of genes. All PPARs are known to heterodimerize with the retinoid X receptor (RXR) and bind to specific regions on the DNA of target genes called peroxisome proliferator hormone response elements (PPREs). PPARs play essential roles in the regulation of cellular differentiation, development, and metabolism (carbohydrate, lipid, protein), and tumorigenesis of higher organisms. The family comprises three members, PPAR-α, PPAR-γ, and PPAR-δ (also known as PPAR-β). PPAR-α is expressed in liver, kidney, heart, muscle, adipose tissue, as well as other tissues. PPAR-δ is expressed in many tissues but markedly in brain, adipose tissue, and skin. PPAR-γ comprises three alternatively-spliced forms, each with a different expression pattern. PPAR-γ1 is expressed in virtually all tissues, including heart, muscle, colon, kidney, pancreas, and spleen. PPAR-γ2 is expressed mainly in adipose tissue. PPAR-γ3 is expressed in macrophages, large intestine, and white adipose tissue. Endogenous ligands for the PPARs include free fatty acids and eicosanoids. PPAR-γ is activated by PGJ2 (a prostaglandin), whereas PPAR-α is activated by leukotriene B4.

In an embodiment, a therapeutic compound disclosed herein has an anti-inflammatory activity capable of stimulating all PPAR signaling pathways. Such a therapeutic compound includes a PPAR pan-agonist. In other embodiments, a therapeutic compound disclosed herein has an anti-inflammatory activity capable of stimulating one or two of the PPAR signaling pathways. Such a therapeutic compound includes a selective PPAR agonist.

In another embodiment, a therapeutic compound disclosed herein has an anti-inflammatory activity capable of stimulating a PPAR-α signaling pathway. In aspects of this embodiment, a therapeutic compound disclosed herein stimulates a PPAR-α signaling pathway by, e.g., at least 5%, at least 15%, at least 25%, at least 50%, at least 60%, at least 70%, at least 80%, or at least 90%. In other aspects of this embodiment, a therapeutic compound disclosed herein stimulates a PPAR-α signaling pathway in a range from, e.g., about 5% to about 100%, about 50% to about 100%, about 60% to about 100%, about 70% to about 100%, about 80% to about 100%, about 25% to about 90%, about 50% to about 90%, about 60% to about 90%, about 70% to about 90%, about 80% to about 90%, about 25% to about 80%, about 50% to about 80%, about 60% to about 80%, about 70% to about 80%, about 25% to about 70%, about 50% to about 70%, about 25% to about 60%, about 50% to about 60%, or about 25% to about 50%.

In another embodiment, a therapeutic compound disclosed herein has an anti-inflammatory activity capable of stimulating a PPAR-δ signaling pathway. In aspects of this embodiment, a therapeutic compound disclosed herein stimulates a PPAR-δ signaling pathway by, e.g., at least 5%, at least 15%, at least 25%, at least 50%, at least 60%, at least 70%, at least 80%, or at least 90%. In other aspects of this embodiment, a therapeutic compound disclosed herein stimulates a PPAR-δ signaling pathway in a range from, e.g., about 5% to about 100%, about 50% to about 100%, about 60% to about 100%, about 70% to about 100%, about 80% to about 100%, about 25% to about 90%, about 50% to about 90%, about 60% to about 90%, about 70% to about 90%, about 80% to about 90%, about 25% to about 80%, about 50% to about 80%, about 60% to about 80%, about 70% to about 80%, about 25% to about 70%, about 50% to about 70%, about 25% to about 60%, about 50% to about 60%, or about 25% to about 50%.

In another embodiment, a therapeutic compound disclosed herein has an anti-inflammatory activity capable of stimulating a PPARγ signaling pathway. A therapeutic compounds disclosed herein may be capable of binding to all isoforms of PPAR-γ, or may be capable of selectively binding to either PPAR-γ1, PPAR-γ2, PPAR-γ3, or any combination of two thereof. In aspects of this embodiment, a therapeutic compound disclosed herein stimulates a PPARγ signaling pathway by, e.g., at least 5%, at least 15%, at least 25%, at least 50%, at least 60%, at least 70%, at least 80%, or at least 90%. In other aspects of this embodiment, a therapeutic compound disclosed herein stimulates a PPARγ signaling pathway in a range from, e.g., about 5% to about 100%, about 50% to about 100%, about 60% to about 100%, about 70% to about 100%, about 80% to about 100%, about 25% to about 90%, about 50% to about 90%, about 60% to about 90%, about 70% to about 90%, about 80% to about 90%, about 25% to about 80%, about 50% to about 80%, about 60% to about 80%, about 70% to about 80%, about 25% to about 70%, about 50% to about 70%, about 25% to about 60%, about 50% to about 60%, or about 25% to about 50%.

Macrophages are activated and polarized into distinct phenotypes expressing unique cell surface molecules and secreting discrete sets of cytokines and chemokines. The classical M1 phenotype supports pro-inflammatory Th1 responses driven by cytokines such as, e.g., Interleukin-6 (IL-6), IL-12 and IL-23, while the alternate M2 phenotype is generally supportive of anti-inflammatory processes driven by IL-10. M2 cells can be further classified into subsets, M2a, M2b, and M2c, based on the type of stimulation and the subsequent expression of surface molecules and cytokines.

In yet another embodiment, a therapeutic compound disclosed herein has an anti-inflammatory activity capable of promoting the resolving phenotypic change of M1 to M2. In an aspect of this embodiment, a therapeutic compound disclosed herein has an anti-inflammatory activity capable of inducing apoptosis of Macrophage M1 cells. In another aspect of this embodiment, a therapeutic compound disclosed herein has an anti-inflammatory activity capable of promoting differentiation of Macrophage M2 cells. In yet another aspect of this embodiment, a therapeutic compound disclosed herein has an anti-inflammatory activity capable of inducing apoptosis of Macrophage M1 cells and promoting differentiation of Macrophage M2 cells.

In still another embodiment, a therapeutic compound disclosed herein has an anti-inflammatory activity capable of modulating Th1 and Th2 cytokines. In an aspect of this embodiment, a therapeutic compound disclosed herein has an anti-inflammatory activity capable of reducing the levels of Interferon-gamma (IFNγ), Tumor necrosis factor-alpha (TNF-α), Interleukin-12 (IL-12), or a combination thereof released from a Th1 cell. In other aspects of this embodiment, a therapeutic compound disclosed herein has an anti-inflammatory activity capable of reducing the levels of IFNγ, TNF-α, IL-12, or a combination thereof released from a Th1 cell by, e.g., at least 10%, at least 20%, at least 30%, at least 40%, at least 50%, at least 60%, at least 70%, at least 80%, or at least 90%. In yet other aspects of this embodiment, a therapeutic compound disclosed herein has an anti-inflammatory activity capable of reducing the levels of IFNγ, TNF-α, IL-12, or a combination thereof released from a Th1 cell in a range from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another aspect of this embodiment, a therapeutic compound disclosed herein has an anti-inflammatory activity capable of increasing the levels of IL-10 released from a Th2 cell. In other aspects of this embodiment, a therapeutic compound disclosed herein has an anti-inflammatory activity capable of increasing the levels of IL-10 released from a Th2 cell by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a therapeutic compound disclosed herein has an anti-inflammatory activity capable of increasing the levels of IL-10 released from a Th2 cell in a range from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In another aspect of this embodiment, a therapeutic compound disclosed herein has an anti-inflammatory activity capable of reducing the levels of IFNγ, TNF-α, IL-12, or a combination thereof released from a Th1 cell and increasing the levels of IL-10 released from a Th2 cell. In other aspects of this embodiment, a therapeutic compound disclosed herein has an anti-inflammatory activity capable of reducing the levels of IFNγ, TNF-α, IL-12, or a combination thereof released from a Th1 cell by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%, and capable of increasing the levels of IL-10 released from a Th2 cell by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a therapeutic compound disclosed herein has an anti-inflammatory activity capable of reducing the levels of IFNγ, TNF-α, IL-12, or a combination thereof released from a Th1 cell in a range from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%, and capable of increasing the levels of IL-10 released from a Th2 cell in a range from, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

A therapeutic compound disclosed herein may have a log P value indicating that the compound is soluble in an organic solvent. As used herein, the term "log P value" refers to the logarithm (base 10) of the partition coefficient (P) for a compound and is a measure of lipophilicity. Typically, P is defined as the ratio of concentrations of a unionized compound in the two phases of a mixture of two immiscible solvents at equilibrium. Thus, log P=Log 10 (P), where P=[solute in immiscible solvent 1]/[solute in immiscible solvent 2]. With regard to organic and aqueous phases, the log P value of a compound is constant for any given pair of aqueous and organic solvents, and its value can be determined empirically by one of several phase-partitioning methods known to one skilled in the art including, e.g., a shake flask assay, a HPLC assay, and an interface between two immiscible electrolyte solutions (ITIES) assay.

In aspects of this embodiment, a therapeutic compound disclosed herein may have a log P value indicating that the compound is substantially soluble in an organic solvent. In aspects of this embodiment, a therapeutic compound disclosed herein may have a log P value indicating that the compound is, e.g., at least 50% soluble in an organic solvent, at least 60% soluble in an organic solvent, at least 70% soluble in an organic solvent, at least 80% soluble in an organic solvent, or at least 90% soluble in an organic solvent. In aspects of this embodiment, a therapeutic compound disclosed herein may have a log P value indicating that the compound is between, e.g., about 50% to about 100% soluble in an organic solvent, about 60% to about 100% soluble in an organic solvent, about 70% to about 100% soluble in an organic solvent, about 80% to about 100% soluble in an organic solvent, or about 90% to about 100% soluble in an organic solvent.

In aspects of this embodiment, a therapeutic compound disclosed herein may have a log P value of, e.g., more than 1.1, more than 1.2, more than 1.4, more than 1.6, more than 1.8, more than 2.0, more than 2.2, more than 2.4, more than 2.6, more than 2.8, more than 3.0, more than 3.2, more than 3.4, or more than 3.6. In other aspects of this embodiment, a therapeutic compound disclosed herein may have a log P value in the range of, e.g., between 1.8 and 4.0, between 2.0 and 4.0, between 2.1 and 4.0, between 2.2 and 4.0, or between 2.3 and 4.0, between 2.4 and 4.0, between 2.5 and 4.0, between 2.6 and 4.0, or between 2.8 and 4.0. In other aspects of this embodiment, a therapeutic compound disclosed herein may have a log P value in the range of, e.g., between 3.0 and 4.0, or between 3.1 and 4.0, between 3.2 and 4.0, between 3.3 and 4.0, between 3.4 and 4.0, between 3.5 and 4.0, or between 3.6 and 4.0. In still other aspects of this embodiment, a therapeutic compound disclosed herein may have a log P value in the range of, e.g., between 2.0 and 2.5, between 2.0 and 2.7, between 2.0 and 3.0, or between 2.2 and 2.5.

A therapeutic compound disclosed herein may have a polar surface area that is hydrophobic. As used herein, the term "polar surface area" refers to the surface sum over all of the polar atoms in the structure of a compound and is a measure of hydrophobicity. Typically, these polar atoms include, e.g., oxygen, nitrogen, and their attached hydrogens. In aspects of this embodiment, a therapeutic compound disclosed herein may have a polar surface area of, e.g., less than 8.0 $nm^2$, less than 7.0 $nm^2$, less than 6.0 $nm^2$, less than 5.0 $nm^2$, less than 4.0 $nm^2$, or less than 3.0 $nm^2$. In other aspects of this embodiment, a therapeutic compound disclosed herein may have a polar surface area in the range of, e.g., between 3.0 $nm^2$ and 6.5 $nm^2$, between 3.0 $nm^2$ and 6.0 $nm^2$, between 3.0 $nm^2$ and 5.5 $nm^2$, between 3.0 $nm^2$ and 5.0 $nm^2$, between 3.0 $nm^2$ and 4.5 $nm^2$, between 3.5 $nm^2$ and 6.5 $nm^2$, between 3.5 $nm^2$ and 6.0 $nm^2$, between 3.5 $nm^2$ and 5.5 $nm^2$, between 3.5 $nm^2$ and 5.0 $nm^2$, between 3.5 $nm^2$ and 4.5 $nm^2$, between 4.0 $nm^2$ and 6.5 $nm^2$, between 4.0 $nm^2$ and 6.0 $nm^2$, between 4.0 $nm^2$ and 5.5 $nm^2$, or between 4.0 $nm^2$ and 5.0 $nm^2$, between 4.0 $nm^2$ and 4.5 $nm^2$, or between 4.5 $nm^2$ and 5.5 $nm^2$. In yet other aspects of this embodiment, a therapeutic compound disclosed herein may have a polar surface area in the range of, e.g., between 2.0 $nm^2$ and 6.5 $nm^2$, between 2.0 $nm^2$ and 6.0 $nm^2$, between 2.0 $nm^2$ and 5.5 $nm^2$, between 2.0 $nm^2$ and 5.0 $nm^2$, between 2.0 $nm^2$ and 4.5 $nm^2$, between 2.5 $nm^2$ and 6.5 $nm^2$, between 2.5 $nm^2$ and 6.0 $nm^2$, between 2.5 $nm^2$ and 5.5 $nm^2$, between 2.5 $nm^2$ and 5.0 $nm^2$, or between 2.5 $nm^2$ and 4.5 $nm^2$.

A therapeutic compound disclosed herein may be a non-steroidal anti-inflammatory drug (NSAID). NSAIDs are a large group of therapeutic compounds with analgesic, anti-inflammatory, and anti-pyretic properties. NSAIDs reduce inflammation by blocking cyclooxygenase. NSAIDs include, without limitation, Aceclofenac, Acemetacin, Actarit, Alcofenac, Alminoprofen, Amfenac, Aloxipirin, Aminophenazone, Antraphenine, Aspirin, Azapropazone, Benorilate, Benoxaprofen, Benzydamine, Butibufen, Celecoxib, Chlorthenoxacin, Choline Salicylate, Clometacin, Dexketoprofen, Diclofenac, Diflunisal, Emorfazone, Epirizole; Etodolac, Etoricoxib, Feclobuzone, Felbinac, Fenbufen, Fenclofenac, Flurbiprofen, Glafenine, Hydroxyethyl salicylate, Ibuprofen, Indometacin, Indoprofen, Ketoprofen, Ketorolac, Lactyl phenetidin, Loxoprofen, Lumiracoxib, Mefenamic acid, Meloxicam, Metamizole, Metiazinic acid, Mofebutazone, Mofezolac, Nabumetone, Naproxen, Nifenazone, Niflumic acid, Oxametacin, Phenacetin, Pipebuzone, Pranoprofen, Propyphenazone, Proquazone, Protizinic acid, Rofecoxib, Salicylamide, Salsalate, Sulindac, Suprofen, Tiaramide, Tinoridine, Tolfenamic acid, Valdecoxib, and Zomepirac.

NSAIDs may be classified based on their chemical structure or mechanism of action. Non-limiting examples of NSAIDs include a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, and a selective cyclooxygenase 2 (COX 2) inhibitor. A NSAID may be a profen. Examples of a suitable salicylate derivative NSAID include, without limitation, Acetylsalicylic acid (asprin), Diflunisal, and Salsalate. Examples of a suitable p-amino phenol derivative NSAID include, without limitation, Paracetamol and Phenacetin. Examples of a suitable propionic acid derivative NSAID include, without limitation, Alminoprofen, Benoxaprofen, Dexketoprofen, Fenoprofen, Flurbiprofen, Ibuprofen, Indoprofen, Ketoprofen, Loxoprofen, Naproxen, Oxaprozin, Pranoprofen, and Suprofen. Examples of a suitable acetic acid derivative NSAID include, without limitation, Aceclofenac, Acemetacin, Actarit, Alcofenac, Amfenac, Clometacin, Diclofenac, Etodolac, Felbinac, Fenclofenac, Indometacin, Ketorolac, Metiazinic acid, Mofezolac, Nabumetone, Naproxen, Oxametacin, Sulindac, and Zomepirac. Examples of a suitable enolic acid (Oxicam) derivative NSAID include, without limitation, Droxicam, Isoxicam, Lornoxicam, Meloxicam, Piroxicam, and Tenoxicam. Examples of a suitable fenamic acid derivative NSAID include, without limitation, Flufenamic acid, Mefenamic acid, Meclofenamic acid, and Tolfenamic acid. Examples of a suitable selective COX-2 inhibitors include, without limitation, Celecoxib, Etoricoxib, Firocoxib, Lumiracoxib, Meloxicam, Paracetamol (Acetaminophen), Parecoxib, Rofecoxib, and Valdecoxib.

A therapeutic compound disclosed herein may be a PPARα agonist. Examples of a suitable PPARα agonist include, without limitation, Pirinixic (WY 14643), GW6471, and a Fibrate.

A therapeutic compound disclosed herein may be a PPARβ/δ agonist. Examples of a suitable PPARβ/δ agonist include, without limitation, Tetradecylthioacetic acid (TTA). GSK0660, GSK3787, GW501516 (GW-501, 516, GW1516, GSK-516 and Endurobol), GW0742, and GW610742X.

A therapeutic compound disclosed herein may be a PPARγ agonist. Examples of a suitable PPARγ agonist include, without limitation, Monascin, a Thiazolidinediones like Rosiglitazone, Pioglitazone, and Troglitazone and T0070907. Other suitable PPARγ agonists are described in Masson and Caumont-Bertrand, PPAR Agonist Compounds, Preparation and Uses, US 2011/0195993, which is hereby incorporated by reference in its entirety.

A therapeutic compound disclosed herein may be a Glitazar (a duel α and γ PPAR agonist). Examples of a suitable Glitazar include, without limitation, Aleglitazar, Muraglitazar, Saroglitazar, and Tesaglitazar.

A therapeutic compound disclosed herein may be an immunosupressive drug. Examples of a suitable immunosupressive drug include, without limitation, Azathioprine and Mycophenolic acid.

A therapeutic compound disclosed herein may be an uricosuric drug. Examples of a suitable uricosuric drug include, without limitation, Benzbromarone.

A therapeutic compound disclosed herein may be an Aglycone. Examples of a suitable Aglycone drug include, without limitation, Piceatannol, Pinosylvin, Pterostilbene, and Resveratrol A therapeutic compound disclosed herein may be a Cannabidiol. Examples of a suitable uricosuric drug include, without limitation, a Phytocannabinoid, an Endocannabinoid, and a synthetic cannabinoid. A Phytocannabinoid includes a Tetrahydrocannabinol (such as, e.g., Delta-9-tetrahydrocannabinol (Δ9-THC, THC), and Delta-8-tetrahydrocannabinol (Δ8-THC)), a Cannabidiol, a Cannabinol, a Cannabigerol, a Tetrahydrocannabivarin, a Cannabidivarin, and a Cannabichromene. An Endocannabinoid includes Arachidonoylethanolamine (Anandamide or AEA), 2-arachidonoyl glycerol (2-AG), 2-arachidonyl glyceryl ether (noladin ether), N-arachidonoyl-dopamine (NADA), Virodhamine (OAE), and Lysophosphatidylinositol (LPI). A synthetic cannabinoid includes Dronabinol (Marinol), Nabilone (Cesamet), Sativex, Rimonabant (SR141716), JWH-018, JWH-073, CP-55940, Dimethylheptylpyran, HU-210, HU-331, SR144528, WIN 55, 212-2, JWH-133, Levonantradol (Nantrodolum), and AM-2201.

A therapeutic compound disclosed herein may be a nuclear receptor binding agent. Examples of a suitable nuclear receptor binding agent include, without limitation, a Retinoic Acid Receptor (RAR) binding agent, a Retinoid X Receptor (RXR) binding agent, a Liver X Receptor (LXR) binding agent and a Vitamin D binding agent.

A therapeutic compound disclosed herein may be an Angiotensin II receptor antagonist. Examples of a suitable Angiotensin II receptor antagonist include, without limitation, Azilsartan, Candesartan, Eprosartan, Irbesartan, Losartan, Olmesartan, Telmisartan, and Valsartan.

A therapeutic compound disclosed herein may be an Acetylcholinesterase (ACE) inhibitor. Examples of a suitable ACE inhibitor include, without limitation, a Sulfhydryl-containing agent, a Dicarboxylate-containing agent, a Phosphonate-containing agent, a Casokinin, and a Lactokinin. A Sulfhydryl-containing agent includes Captopril (Capoten) and Zofenopril. A Dicarboxylate-containing agent includes Enalapril (Vasotec/Renitec), Ramipril (Altace/Prilace/Ramace/Ramiwin/Triatec/Tritace), Quinapril (Accupril), Perindopril (Coversyl/Aceon), Lisinopril (Listril/Lopril/Novatec/Prinivil/Zestril), Benazepril (Lotensin), Imidapril (Tanatril), Zofenopril (Zofecard), and Trandolapril (Mavik/Odrik/Gopten). A Phosphonate-containing agent includes Fosinopril (Fositen/Monopril).

A therapeutic compound disclosed herein may be a Phosphodiesterase inhibitor. Examples of a suitable Phosphodiesterase inhibitor include, without limitation, a PDE 1 selective inhibitor, a PDE 2 selective inhibitor, a PDE 3 selective inhibitor, a PDE 4 selective inhibitor, a PDE 5 selective inhibitor, and a PDE 10 selective inhibitor. A PDE1 selective inhibitor includes Vinpocetine. A PDE2 selective inhibitor includes BAY 60-7550 (2-[(3,4-dimethoxyphenyl)methyl]-7-[(1R)-1-hydroxyethyl]-4-phenylbutyl]-5-methyl-imidazo[5,1-f][1,2,4]triazin-4(1H)-one), EHNA (erythro-9-(2-hydroxy-3-nonyl)adenine), Oxindole, and PDP (9-(6-Phenyl-2-oxohex-3-yl)-2-(3,4-dimethoxybenzyl)-purin-6-one). A PDE3 selective inhibitor includes Anagrelide, Cilostazol, Enoximone, Inamrinone, and Milrinone. A PDE4 selective inhibitor includes Drotaverine, Ibudilast, Luteolin, Mesembrine, Piclamilast, Roflumilast, and Rolipram. A PDE5 selective inhibitor includes Avanafil, Dipyridamole, Icariin, 4-Methylpiperazine, Pyrazolo Pyrimidin-7-1, Sildenafil, Tadalafil, Udenafil, and Vardenafil. A PDE10 selective inhibitor includes Papaverine.

A therapeutic compound disclosed herein may be a fibrate. Fibrates are a class of amphipathic carboxylic acids with lipid level modifying properties. These therapeutic compounds are used for a range of metabolic disorders. One non-limiting use is as an anti-hyperlipidemic agent where it may lower levels of, e.g., triglycerides and LDL as well as increase levels of HDL. Examples of a suitable fibrate include, without limitation, Bezafibrate, Ciprofibrate, Clofibrate, Gemfibrozil, and Fenofibrate.

A therapeutic compound disclosed herein may be a statin. Statins (or HMG-CoA reductase inhibitors) are a class of therapeutic compounds used to lower LDL and/or cholesterol levels by inhibiting the enzyme HMG-CoA reductase, which plays a central role in the production of cholesterol in the liver. To compensate for the decreased cholesterol availability, synthesis of hepatic LDL receptors is increased, resulting in an increased clearance of LDL particles from the blood. Examples of a suitable statin include, without limitation, Atorvastatin, Fluvastatin, Lovastatin, Pitavastatin, Pravastatin, Rosuvastatin, and Simvastatin.

A therapeutic compound disclosed herein may be a tocotrienol. Tocotrienols are another class of HMG-CoA reductase inhibitors and may be used to lower LDL and/or cholesterol levels by inducing hepatic LDL receptor up-regulation and/or decreasing plasma LDL levels. Examples of a suitable tocotrienol include, without limitation, a γ-tocotrienol and a δ-tocotrienol.

A therapeutic compound disclosed herein may be a niacin. Niacins are a class of therapeutic compounds with lipid level modifying properties. For example, a niacin may lower LDL by selectively inhibiting hepatic diacyglycerol acyltransferase 2, reduce triglyceride synthesis, and VLDL secretion through a receptor HM74 and HM74A or GPR109A. These therapeutic compounds are used for a range of metabolic disorders. One non-limiting use is as an anti-hyperlipidemic agent where it may inhibit the breakdown of fats in adipose tissue. Because a niacin blocks the breakdown of fats, it causes a decrease in free fatty acids in the blood and, as a consequence, decreases the secretion of very-low-density lipoproteins (VLDL) and cholesterol by the liver. By lowering VLDL levels, a niacin may also increase the level of HDL in blood. Examples of a suitable niacin include, without limitation, Acipimox, Niacin, Nicotinamide, and Vitamin B3.

A therapeutic compound disclosed herein may be a bile acid sequestrant. Bile acid sequestrants (also known as resins) are a class of therapeutic compounds used to bind certain components of bile in the gastrointestinal tract. They disrupt the enterohepatic circulation of bile acids by sequestering them and preventing their reabsorption from the gut. Bile acid sequestrants are particularly effective for lowering LDL and cholesterol by sequestering the cholesterol-containing bile acids released into the intestine and preventing their reabsorption from the intestine. In addition, a bile acid sequestrant may also raise HDL levels. Examples of a suitable bile acid sequestrant include, without limitation, Cholestyramine, Colesevelam, and Colestipol.

A therapeutic compound disclosed herein may be a cholesterol absorption inhibitor. Cholesterol absorption inhibitors are a class of therapeutic compounds that inhibits the absorption of cholesterol from the intestine. Decreased cholesterol absorption leads to an upregulation of LDL-receptors on the surface of cells and an increased LDL-cholesterol uptake into these cells, thus decreasing levels of LDL in the blood plasma. Examples of a suitable cholesterol absorption inhibitor include, without limitation, Ezetimibe, a phytosterol, a sterol and a stanol.

A therapeutic compound disclosed herein may be a fat absorption inhibitor. Fat absorption inhibitors are a class of therapeutic compounds that inhibits the absorption of fat from the intestine. Decreased fat absorption reduces caloric intake. In one aspect, a fat absorption inhibitor inhibits pancreatic lipase, an enzyme that breaks down triglycerides in the intestine. Examples of a suitable fat absorption inhibitor include, without limitation, Orlistat.

A therapeutic compound disclosed herein may be a sympathomimetic amine. Sympathomimetic amines are a class of therapeutic compounds that mimic the effects of transmitter substances of the sympathetic nervous system such as catecholamines, epinephrine (adrenaline), norepinephrine (noradrenaline), and/or dopamine. A sympathomimetic amine may act as an α-adrenergic agonist, a β-adrenergic agonist, a dopaminergic agonist, a monoamine oxidase (MAO) inhibitor, and a COMT inhibitor. Such therapeutic compounds, among other things, are used to treat cardiac arrest, low blood pressure, or even delay premature labor. Examples of a suitable sympathomimetic amine include, without limitation, Clenbuterol, Salbutamol, ephedrine, pseudoephedrine, methamphetamine, amphetamine, phenylephrine, isoproterenol, dobutamine, methylphenidate, lisdexamfetamine, cathine, cathinone, methcathinone, cocaine, benzylpiperazine (BZP), methylenedioxypyrovalerone (MDPV), 4-methylaminorex, pemoline, phenmetrazine, and propylhexedrine. An α-adrenergic agonist includes Phenylephrine, Propylhexedrine, and Pseudoephedrine. A β-adrenergic agonist includes Clenbuterol, Dobutamine, Eephedrine, Isoproterenol, and Salbutamol. A Dopaminergic/Norepinephrinergic agonist includes Cocaine (DA/NE reuptake inhibitor), Lisdexamfetamine (5HT/DA/NE reuptake inhibitor), Methylphenidate (DA/NE reuptake inhibitor), and Methylenedioxypyrovalerone (DA/NE reuptake inhibitor). A Neurotransmitter releasing agent includes Amphetamine (DA/NE releasing agent), Benzylpiperazine (DA/NE releasing agent), Cathine (DA/NE releasing agent), Cathinone (DA/NE releasing agent), Methamphetamine (DA/NE releasing agent), Methcathinone (DA/NE releasing agent), 4-methylaminorex (DA/NE releasing agent), Pemoline, Phenmetrazine (DA/NE releasing agent), and Phenethylamine (DA/NE releasing agent).

A therapeutic compound disclosed herein may be a Ryanodine receptor antagonist. Examples of a Ryanodine receptor antagonist include, without limitation, Azumolene and Dantrolene.

A therapeutic compound disclosed herein may be a cancer drug. Examples of a suitable cancer drug include, without limitation, an alkylating agent, an anti-metabolite, a plant alkaloid and terpenoid, a topoisomerase inhibitor and a cytotoxic antibiotic. An alkylating agent includes Carboplatin, Chlorambucil, Cisplatin, Cyclophosphamide, Ifosfamide, Oxaliplatin, and Mechlorethamine. An anti-metabolite includes Azathioprine and Mercaptopurine. A plant alkaloid and terpenoid include a *Vinca* alkaloid like Vincristine, Vinblastine, Vinorelbine, and Vindesine, a Podophyllotoxin like Etoposide and Teniposide, and a Taxane like Docetaxel and Ortataxel. A Topoisomerase inhibitor includes a Type I topoisomerase inhibitor like a Camptothecins, such as, e.g., Exatecan, Irinotecan, Lurtotecan, Topotecan, BNP 1350, CKD 602, DB 67 (AR67), and ST 1481, and a Type II inhibitor like an Epipodophyllotoxin such as, e.g., Amsacrine, Etoposid, Etoposide phosphate, and Teniposide. A Cytotoxic antibiotic includes an Actinomycin like Actinomycin D, Bacitracin, Colistin (polymyxin E), and Polymyxin B, an Anthracenedione like Mitoxantrone and Pixantrone, and a Anthracycline like Bleomycin, Doxorubicin (Adriamycin), Daunorubicin (Daunomycin), Epirubicin, Idarubicin, Mitomycin, Plicamycin, and Valrubicin.

A therapeutic compound disclosed herein may be Metformin, Curcumin, glycyrrhetinic acid, or 6-shogaol.

A therapeutic compound disclosed herein may be an antibiotic. Examples of a suitable sympathomimetic amine include, without limitation, Isoniazid, Rifampicin, Pyrazinamide, and Ethambutol.

A therapeutic compound disclosed herein may be an anti-helmintic drug. Examples of a suitable anti-helmintic drug include, without limitation, Abamectin, an Aminoacetonitrile like Monepantel, a Benzimidazole, Diethylcarbamazine, Ivermectin, Levamisole, Niclosamide, an Octadepsipeptide like Emodepside, Phosphonic acid (Metrifonate), Praziquantel, a Spiroindole like Derquantel, and Suramin Pyrantel pamoate. A Benzimidazole includes Albendazole, Fenbendazole, Flubendazole, Mebendazole, Thiabendazole, and Triclabendazole.

A therapeutic compound disclosed herein may be an anti-malaria drug. Examples of a suitable anti-malaria drug include, without limitation, Amodiaquine, an Artemisinin, Atovaquone, Chloroquine, Clindamycin, Doxycycline, Halofantrine, Mefloquine, Primaquine, Proguanil, Pyrimethamine, a Quinine and related agent like Quinimax and Quinidine, Rufigallol, and a Sulfonamide like Sulfadoxine and Sulfamethoxypyridazine. An Artemisinin includes Arteether, Artemether, Artemisinin, Artesunate, and Dihydroartemisinin.

A therapeutic compound disclosed herein may be an anti-hyperlipidemic agent. There are several classes of anti-hyperlipidemic agents (also known as hypolipidemic agents). They may differ in both their impact on the cholesterol profile and adverse effects. For example, some may lower low density lipoprotein (LDL), while others may preferentially increase high density lipoprotein (HDL). Clinically, the choice of an agent will depend on the cholesterol profile of an individual, cardiovascular risk of an individual, and/or the liver and kidney functions of an individual. Examples of a suitable anti-hyperlipidemic agent include, without limitation, an Angiotensin II receptor antagonist, an ACE inhibitor, a Phosphodiesterase inhibitor, a Fibrate, a Statin, a Tocotrienol, a Niacin, a bile acid sequestrants (resin), a cholesterol absorption inhibitor, a pancreatic lipase inhibitor, and a sympathomimetic amine.

A therapeutic compound disclosed herein may be an ester of a therapeutic compound. An ester of a therapeutic compound increases the log P value relative to the same therapeutic compound, but without the ester modification. An ester group may be attached to a therapeutic compound by, e.g., a carboxylic acid or hydroxyl functional group present of the therapeutic compound. An ester of a therapeutic compound may have an increased hydrophobicity, and as such, may be dissolved in a reduced volume of solvent disclosed herein. In some instances, an ester of a therapeutic compound may be combined directly with an adjuvant disclosed herein, thereby eliminating the need of a solvent. An ester of a therapeutic compound may enable the making of a pharmaceutical composition disclosed herein, in situations where a non-esterified form of the same therapeutic compound is otherwise immiscible in a solvent disclosed herein. An ester of a therapeutic compound may still be delivered in a manner that more effectively inhibits a pro-inflammatory response as long as the compound is combined with an adjuvant disclosed herein. In one embodiment, a therapeutic compound may be reacted with ethyl ester in order to form an ethyl ester of the therapeutic compound.

A solid solution pharmaceutical composition disclosed herein may comprise a therapeutic compound in an amount sufficient to allow customary administration to an individual. In aspects of this embodiment, a pharmaceutical composition disclosed herein may comprise a therapeutic compound in an amount of, e.g., at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, or at least 100 mg. In other aspects of this embodiment, a pharmaceutical composition disclosed herein may comprise a therapeutic compound in an amount of, e.g., at least 5 mg, at least 10 mg, at least 20 mg, at least 25 mg, at least 50 mg, at least 75 mg, at least 100 mg, at least 200 mg, at least 300 mg, at least 400 mg, at least 500 mg, at least 600 mg, at least 700 mg, at least 800 mg, at least 900 mg, at least 1,000 mg, at least 1,100 mg, at least 1,200 mg, at least 1,300 mg, at least 1,400 mg, or at least 1,500 mg. In yet other aspects of this embodiment, a pharmaceutical composition disclosed herein may comprise a therapeutic compound in an amount of, e.g., about 5 mg to about 100 mg, about 10 mg to about 100 mg, about 50 mg to about 150 mg, about 100 mg to about 250 mg, about 150 mg to about 350 mg, about 250 mg to about 500 mg, about 350 mg to about 600 mg, about 500 mg to about 750 mg, about 600 mg to about 900 mg, about 750 mg to about 1,000 mg, about 850 mg to about 1,200 mg, or about 1,000 mg to about 1,500 mg. In still other aspects of this embodiment, a pharmaceutical composition disclosed herein may comprise a therapeutic compound in an amount of, e.g., about 10 mg to about 250 mg, about 10 mg to about 500 mg, about 10 mg to about 750 mg, about 10 mg to about 1,000 mg, about 10 mg to about 1,500 mg, about 50 mg to about 250 mg, about 50 mg to about 500 mg, about 50 mg to about 750 mg, about 50 mg to about 1,000 mg, about 50 mg to about 1,500 mg, about 100 mg to about 250 mg, about 100 mg to about 500 mg, about 100 mg to about 750 mg, about 100 mg to about 1,000 mg, about 100 mg to about 1,500 mg, about 200 mg to about 500 mg, about 200 mg to about 750 mg, about 200 mg to about 1,000 mg, about 200 mg to about 1,500 mg, about 5 mg to about 1,500 mg, about 5 mg to about 1,000 mg, or about 5 mg to about 250 mg.

In other aspects of this embodiment, a pharmaceutical composition disclosed herein may comprise a therapeutic compound in an amount of, e.g., less than about 90% by weight, less than about 80% by weight, less than about 70% by weight, less than about 65% by weight, less than about 60% by weight, less than about 55% by weight, less than about 50% by weight, less than about 45% by weight, less than about 40% by weight, less than about 35% by weight, less than about 30% by weight, less than about 25% by weight, less than about 20% by weight, less than about 15% by weight, less than about 10% by weight, less than about 5% by weight, or less than about 1% by weight. In other aspects of this embodiment, a pharmaceutical composition disclosed herein may comprise a therapeutic compound in an amount of, e.g., about 1% to 90% by weight, about 1% to 80% by weight, about 1% to 75% by weight, about 1% to 70% by weight, about 1% to 65% by weight, about 1% to 60% by weight, about 1% to 55% by weight, about 1% to 50% by weight, about 1% to 45% by weight, about 1% to 40% by weight, about 1% to 35% by weight, about 1% to 30% by weight, about 1% to 25% by weight, about 1% to 20% by weight, about 1% to 15% by weight, about 1% to 10% by weight, about 1% to 5% by weight, about 2% to 50% by weight, about 2% to 40% by weight, about 2% to 30% by weight, about 2% to 20% by weight, about 2% to 10% by weight, about 4% to 50% by weight, about 4% to 40% by weight, about 4% to 30% by weight, about 4% to 20% by weight, about 4% to 10% by weight, about 6% to 50% by weight, about 6% to 40% by weight, about 6% to 30% by weight, about 6% to 20% by weight, about 6% to 10% by weight, about 8% to 50% by weight, about 8% to 40% by weight, about 8% to 30% by weight, about 8% to 20% by weight, about 8% to 15% by weight, or about 8% to 12% by weight.

In other aspects of this embodiment, a pharmaceutical composition disclosed herein may comprise a therapeutic compound in an amount of, e.g., about 0.1% to about 45% by weight, about 0.1% to about 40% by weight, about 0.1% to about 35% by weight, about 0.1% to about 30% by weight, about 0.1% to about 25% by weight, about 0.1% to about 20% by weight, about 0.1% to about 15% by weight, about 0.1% to about 10% by weight, about 0.1% to about 5% by weight, about 1% to about 45% by weight, about 1% to about 40% by weight, about 1% to about 35% by weight, about 1% to about 30% by weight, about 1% to about 25% by weight, about 1% to about 20% by weight, about 1% to about 15% by weight, about 1% to about 10% by weight, about 1% to about 5% by weight, about 5% to about 45% by weight, about 5% to about 40% by weight, about 5% to about 35% by weight, about 5% to about 30% by weight, about 5% to about 25% by weight, about 5% to about 20% by weight, about 5% to about 15% by weight, about 5% to about 10% by weight, about 10% to about 45% by weight, about 10% to about 40% by weight, about 10% to about 35% by weight, about 10% to about 30% by weight, about 10% to about 25% by weight, about 10% to about 20% by weight, about 10% to about 15% by weight, about 15% to about 45% by weight, about 15% to about 40% by weight, about 15% to about 35% by weight, about 15% to about 30% by weight, about 15% to about 25% by weight, about 15% to about 20% by weight, about 20% to about 45% by weight, about 20% to about 40% by weight, about 20% to about 35% by weight, about 20% to about 30% by weight, about 20% to about 25% by weight, about 25% to about 45% by weight, about 25% to about 40% by weight, about 25% to about 35% by weight, or about 25% to about 30% by weight.

The final concentration of a therapeutic compound disclosed herein in a pharmaceutical composition disclosed herein may be of any concentration desired. In an aspect of this embodiment, the final concentration of a therapeutic compound in a pharmaceutical composition may be a therapeutically effective amount. In other aspects of this embodiment, the final concentration of a therapeutic compound in a pharmaceutical composition may be, e.g., at least 0.00001 mg/mL, at least 0.0001 mg/mL, at least 0.001 mg/mL, at least 0.01 mg/mL, at least 0.1 mg/mL, at least 1 mg/mL, at least 10 mg/mL, at least 25 mg/mL, at least 50 mg/mL, at least 100 mg/mL, at least 200 mg/mL, at least 500 mg/mL, at least 700 mg/mL, at least 1,000 mg/mL, or at least 1,200 mg/mL. In other aspects of this embodiment, the concentration of a therapeutic compound disclosed herein in the solution may be, e.g., at most 1,000 mg/mL, at most 1,100 mg/mL, at most 1,200 mg/mL, at most 1,300 mg/mL, at most 1,400 mg/mL, at most 1,500 mg/mL, at most 2,000 mg/mL, at most 2,000 mg/mL, or at most 3,000 mg/mL. In other aspects of this embodiment, the final concentration of a therapeutic compound in a pharmaceutical composition may be in a range of, e.g., about 0.00001 mg/mL to about 3,000 mg/mL, about 0.0001 mg/mL to about 3,000 mg/mL, about 0.01 mg/mL to about 3,000 mg/mL, about 0.1 mg/mL to about 3,000 mg/mL, about 1 mg/mL to about 3,000 mg/mL, about 250 mg/mL to about 3,000 mg/mL, about 500 mg/mL to about 3,000 mg/mL, about 750 mg/mL to about 3,000 mg/mL, about 1,000 mg/mL to about 3,000 mg/mL, about 100 mg/mL to about 2,000 mg/mL, about 250 mg/mL to about 2,000 mg/mL, about 500 mg/mL to about 2,000 mg/mL, about 750 mg/mL to about 2,000 mg/mL, about 1,000 mg/mL to about 2,000 mg/mL, about 100 mg/mL to about 1,500 mg/mL, about 250 mg/mL to about 1,500 mg/mL, about 500 mg/mL to about 1,500 mg/mL, about 750 mg/mL to about 1,500 mg/mL, about 1,000 mg/mL to about 1,500 mg/mL, about 100 mg/mL to about 1,200 mg/mL, about 250 mg/mL to about 1,200 mg/mL, about 500 mg/mL to about 1,200 mg/mL, about 750 mg/mL to about 1,200 mg/mL, about 1,000 mg/mL to about 1,200 mg/mL, about 100 mg/mL to about 1,000 mg/mL, about 250 mg/mL to about 1,000 mg/mL, about 500 mg/mL to about 1,000 mg/mL, about 750 mg/mL to about 1,000 mg/mL, about 100 mg/mL to about 750 mg/mL, about 250 mg/mL to about 750 mg/mL, about 500 mg/mL to about 750 mg/mL, about 100 mg/mL to about 500 mg/mL, about 250 mg/mL to about 500 mg/mL, about 0.00001 mg/mL to about 0.0001 mg/mL, about 0.00001 mg/mL to about 0.001 mg/mL, about 0.00001 mg/mL to about 0.01 mg/mL, about 0.00001 mg/mL to about 0.1 mg/mL, about 0.00001 mg/mL to about 1 mg/mL, about 0.001 mg/mL to about 0.01 mg/mL, about 0.001 mg/mL to about 0.1 mg/mL, about 0.001 mg/mL to about 1 mg/mL, about 0.001 mg/mL to about 10 mg/mL, or about 0.001 mg/mL to about 100 mg/mL.

Aspects of the present specification disclose, in part, one or more lipids. A lipid may be broadly defined as a hydrophobic or amphiphilic small molecule. The amphiphilic nature of some lipids allows them to form structures such as vesicles, liposomes, or membranes in an aqueous environment. Non-limiting examples, of lipids include fatty acids, glycerolipids, phospholipids, sphingolipids, sterol lipids, prenol lipids, saccharolipids, and polyketides.

A lipid useful in the pharmaceutical compositions disclosed herein may be a pharmaceutically-acceptable fatty acid. A fatty acid comprises a carboxylic acid with a long unbranched hydrocarbon chain which may be either saturated or unsaturated. Thus arrangement confers a fatty acid with a polar, hydrophilic end, and a nonpolar, hydrophobic end that is insoluble in water. Most naturally occurring fatty acids have a hydrocarbon chain of an even number of carbon atoms, typically between 4 and 24 carbons, and may be attached to functional groups containing oxygen, halogens, nitrogen, and sulfur. Synthetic or non-natural fatty acids may have a hydrocarbon chain of any number of carbon atoms from between 3 and 40 carbons. Where a double bond exists, there is the possibility of either a cis or a trans geometric isomerism, which significantly affects the molecule's molecular configuration. Cis-double bonds cause the fatty acid chain to bend, an effect that is more pronounced the more double bonds there are in a chain. Most naturally occurring fatty acids are of the cis configuration, although the trans form does exist in some natural and partially hydrogenated fats and oils. Examples of fatty acids include, without limitation, Capryllic acid (8:0), Pelargonic acid (9:0), Capric acid (10:0), Undecylic acid (11:0), Lauric acid (12:0), Tridecylic acid (13:0), Myristic acid (14:0), Myristoleic acid (14:1), Pentadecyclic acid (15:0), Palmitic acid (16:0), Palmitoleic acid (16:1), Sapienic acid (16:1), Margaric acid (17:0), Stearic acid (18:0), Oleic acid (18:1), Elaidic acid (18:1), Vaccenic acid (18:1), Linoleic acid (18:2), Linoelaidic acid (18:2), α-Linolenic acid (18:3), γ-Linolenic acid (18:3), Stearidonic acid (18:4), Nonadecylic acid (19:0), Arachidic acid (20:0), Eicosenoic acid (20:1), Dihomo-γ-linolenic acid (20:3), Mead acid (20:3), Arachidonic acid (20:4), Eicosapentaenoic acid (20:5), Heneicosylic acid (21:0), Behenic acid (22:0), Erucic acid (22:1), Docosahexaenoic acid (22:6), Tricosylic acid (23:0), Lignoceric acid (24:0), Nervonic acid (24:1), Pentacosylic acid (25:0), Cerotic acid (26:0), Heptacosylic acid (27:0), Montanic acid (28:0), Nonacosylic acid (29:0), Melissic acid (30:0), Henatriacontylic acid (31:0), Lacceroic acid (32:0), Psyllic acid (33:0), Geddic acid (34:0), Ceroplastic acid (35:0), and Hexatriacontylic acid (36:0).

In an embodiment, a lipid may be a pharmaceutically-acceptable saturated or unsaturated fatty acid. In aspects of this embodiment, a saturated or unsaturated fatty acid comprises, e.g., at least 8, at least 10, at least 12, at least 14, at least 16, at least 18, at least 20, at least 22, at least 24, at least 26, at least 28, or at least 30 carbon atoms, In other aspects of this embodiment, a saturated or unsaturated fatty acid comprises, e.g., between 4 and 24 carbon atoms, between 6 and 24 carbon atoms, between 8 and 24 carbon atoms, between 10 and 24 carbon atoms, between 12 and 24 carbon atoms, between 14 and 24 carbon atoms, or between 16 and 24 carbon atoms, between 4 and 22 carbon atoms, between 6 and 22 carbon atoms, between 8 and 22 carbon atoms, between 10 and 22 carbon atoms, between 12 and 22 carbon atoms, between 14 and 22 carbon atoms, or between 16 and 22 carbon atoms, between 4 and 20 carbon atoms, between 6 and 20 carbon atoms, between 8 and 20 carbon atoms, between 10 and 20 carbon atoms, between 12 and 20 carbon atoms, between 14 and 20 carbon atoms, or between 16 and 20 carbon atoms. If unsaturated, the fatty acid may have, e.g., 1 or more, 2 or more, 3 or more, 4 or more, 5 or more, or 6 or more double bonds.

A lipid useful in the pharmaceutical compositions disclosed herein may be a pharmaceutically-acceptable hard fat. Also known as a "solid fat", room temperature solid lipid", or simply "fat", a hard fat includes any fatty acid that is solid at normal room temperature, such as, e.g. about 20° C. Fats consist of a wide group of compounds that are generally soluble in organic solvents and generally insoluble in water. Examples of mixtures of pharmaceutically-acceptable hard fats include, without limitation, a mixture of one or more glycerolipids disclosed herein, a mixture of one or more glycol fatty acid esters disclosed herein, a mixture of more polyether fatty acid esters disclosed herein, a mixture of more glycerides disclosed herein.

A hard fat useful in the pharmaceutical compositions disclosed herein may be a pharmaceutically-acceptable glycerolipid. Glycerolipids are composed mainly of mono-, di-, and tri-substituted glycerols. One group of glycerolipids is the glycerides, where one, two, or all three hydroxyl groups of glycerol are each esterified using a fatty acid disclosed herein to produce monoglycerides, diglycerides, and triglycerides, respectively. In these compounds, each hydroxyl groups of glycerol may be esterified by the same fatty acid or different fatty acids. Additionally, glycerides may be acetylated to produce acetylated monoglycerides, acetylated diglycerides, and acetylated triglycerides. In aspects of this embodiment, a monoglyceride may include a saturated or unsaturated fatty acid having a carbon length of $C_{12}$-$C_{24}$. In other aspects of this embodiment, a diglyceride may include one saturated or unsaturated fatty acid having a carbon length of $C_{12}$-$C_{24}$, or two saturated or unsaturated fatty acids each having a carbon length of $C_{12}$-$C_{24}$. In yet other aspects of this embodiment, a triglyceride may include one saturated or unsaturated fatty acid having a carbon length of $C_{12}$-$C_{24}$, two saturated or unsaturated fatty acids each having a carbon length of $C_{12}$-$C_{24}$, or three saturated or unsaturated fatty acids each having a carbon length of $C_{12}$-$C_{24}$.

In aspects of this embodiment, a mixture of pharmaceutically-acceptable lipids includes a mixture of mono-, di-, and/or triglycerides having a melting point of, e.g., about 33° C., about 34° C., about 35° C., about 36° C., about 37° C., about 38° C., about 39° C., about 40° C., about 41° C., about 43° C., about 43° C., about 44° C., about 45° C., about 45° C., about 47° C., about 48° C., about 49° C., about 50° C. In aspects of this embodiment, a mixture of pharmaceutically-acceptable lipids includes a mixture of mono-, di-, and/or triglycerides having a melting point of, e.g., about 30° C. to about 44° C., about 30° C. to about 45° C., about 30° C. to about 46° C., about 30° C. to about 47° C., about 30° C. to about 48° C., about 30° C. to about 49° C., about 30° C. to about 50° C., about 32° C. to about 44° C., about 32° C. to about 45° C., about 32° C. to about 46° C., about 32° C. to about 47° C., about 32° C. to about 48° C., about 32° C. to about 49° C., about 32° C. to about 50° C., about 34° C. to about 44° C., about 34° C. to about 45° C., about 34° C. to about 46° C., about 34° C. to about 47° C., about 34° C. to about 48° C., about 34° C. to about 49° C., about 34° C. to about 50° C., about 36° C. to about 44° C., about 36° C. to about 45° C., about 36° C. to about 46° C., about 36° C. to about 47° C., about 36° C. to about 48° C., about 36° C. to about 49° C., about 36° C. to about 50° C., about 38° C. to about 44° C., about 38° C. to about 45° C., about 38° C. to about 46° C., about 38° C. to about 47° C., about 38° C. to about 48° C., about 38° C. to about 49° C., about 38° C. to about 50° C., about 40° C. to about 44° C., about 40° C. to about 45° C., about 40° C. to about 46° C., about 40° C. to about 47° C., about 40° C. to about 48° C., about 40° C. to about 49° C., about 40° C. to about 50° C., about 42° C. to about 44° C., about 42° C. to about 45° C., about 42° C. to about 46° C., about 42° C. to about 47° C., about 42° C. to about 48° C., about 42° C. to about 49° C., or about 42° C. to about 50° C.

In other aspects of this embodiment, a mixture of pharmaceutically-acceptable lipids includes a mixture PEG fatty acid esters having a melting point of, e.g., about 33° C., about 34° C., about 35° C., about 36° C., about 37° C., about 38° C., about 39° C., about 40° C., about 41° C., about 43° C., about 43° C., about 44° C., about 45° C., about 45° C., about 47° C., about 48° C., about 49° C., about 50° C. In aspects of this embodiment, a mixture of pharmaceutically-acceptable lipids includes a mixture PEG fatty acid esters having a melting point of, e.g., about 30° C. to about 44° C., about 30° C. to about 45° C., about 30° C. to about 46° C., about 30° C. to about 47° C., about 30° C. to about 48° C., about 30° C. to about 49° C., about 30° C. to about 50° C., about 32° C. to about 44° C., about 32° C. to about 45° C., about 32° C. to about 46° C., about 32° C. to about 47° C., about 32° C. to about 48° C., about 32° C. to about 49° C., about 32° C. to about 50° C., about 34° C. to about 44° C., about 34° C. to about 45° C., about 34° C. to about 46° C., about 34° C. to about 47° C., about 34° C. to about 48° C., about 34° C. to about 49° C., about 34° C. to about 50° C., about 36° C. to about 44° C., about 36° C. to about 45° C., about 36° C. to about 46° C., about 36° C. to about 47° C., about 36° C. to about 48° C., about 36° C. to about 49° C., about 36° C. to about 50° C., about 38° C. to about 44° C., about 38° C. to about 45° C., about 38° C. to about 46° C., about 38° C. to about 47° C., about 38° C. to about 48° C., about 38° C. to about 49° C., about 38° C. to about 50° C., about 40° C. to about 44° C., about 40° C. to about 45° C., about 40° C. to about 46° C., about 40° C. to about 47° C., about 40° C. to about 48° C., about 40° C. to about 49° C., about 40° C. to about 50° C., about 42° C. to about 44° C., about 42° C. to about 45° C., about 42° C. to about 46° C., about 42° C. to about 47° C., about 42° C. to about 48° C., about 42° C. to about 49° C., or about 42° C. to about 50° C.

In other aspects of this embodiment, a mixture of pharmaceutically-acceptable lipids includes a mixture of mono-, di-, and/or triglycerides and PEG fatty acid esters having a melting point of, e.g., about 33° C., about 34° C., about 35° C., about 36° C., about 37° C., about 38° C., about 39° C., about 40° C., about 41° C., about 43° C., about 43° C., about 44° C., about 45° C., about 45° C., about 47° C., about 48° C., about 49° C., about 50° C. In aspects of this embodiment, a mixture of pharmaceutically-acceptable lipids includes a mixture of mono-, di-, and/or triglycerides and PEG fatty acid esters having a melting point of, e.g., about 30° C. to about 44° C., about 30° C. to about 45° C., about 30° C. to about 46° C., about 30° C. to about 47° C., about 30° C. to about 48° C., about 30° C. to about 49° C., about 30° C. to about 50° C., about 32° C. to about 44° C., about 32° C. to about 45° C., about 32° C. to about 46° C., about 32° C. to about 47° C., about 32° C. to about 48° C., about 32° C. to about 49° C., about 32° C. to about 50° C., about 34° C. to about 44° C., about 34° C. to about 45° C., about 34° C. to about 46° C., about 34° C. to about 47° C., about 34° C. to about 48° C., about 34° C. to about 49° C., about 34° C. to about 50° C., about 36° C. to about 44° C., about 36° C. to about 45° C., about 36° C. to about 46° C., about 36° C. to about 47° C., about 36° C. to about 48° C., about 36° C. to about 49° C., about 36° C. to about 50° C., about 38° C. to about 44° C., about 38° C. to about 45° C., about 38° C. to about 46° C., about 38° C. to about 47° C., about 38° C. to about 48° C., about 38° C. to about 49° C., about 38° C. to about 50° C., about 40° C. to about 44° C., about 40° C. to about 45° C., about 40° C. to about 46° C., about 40° C. to about 47° C., about 40° C. to about 48° C., about 40° C. to about 49° C., about 40° C. to about 50° C., about 42° C. to about 44° C., about 42° C. to about 45° C., about 42° C. to about 46° C., about 42° C. to about 47° C., about 42° C. to about 48° C., about 42° C. to about 49° C., or about 42° C. to about 50° C.

A solid solution pharmaceutical composition disclosed herein may comprise a pharmaceutically-acceptable room temperature solid lipid (hard fat) in an amount sufficient to form solid solution composition disclosed herein. In other aspects of this embodiment, a pharmaceutical composition disclosed herein may comprise a pharmaceutically-acceptable room temperature solid lipid (hard fat) in an amount of, e.g., at least 10% by weight, at least 20% by weight, at least 30% by weight, at least 35% by weight, at least 40% by weight, at least 45% by weight, at least 50% by weight, at least 55% by weight, at least 60% by weight, at least 65% by weight, at least 70% by weight, at least 75% by weight, at least 80% by weight, at least 85% by weight, at least 90% by weight, at least 95% by weight, or at least 99% by weight. In other aspects of this embodiment, a pharmaceutical composition disclosed herein may comprise a pharmaceutically-acceptable room temperature solid lipid (hard fat) in an amount of, e.g., about 30% to about 99% by weight, about 35% to about 99% by weight, about 40% to about 99% by weight, about 45% to about 99% by weight, about 50% to about 99% by weight, about 30% to about 98% by weight, about 35% to about 98% by weight, about 40% to about 98% by weight, about 45% to about 98% by weight, about 50% to about 98% by weight, about 30% to about 95% by weight, about 35% to about 95% by weight, about 40% to about 95% by weight, about 45% to about 95% by weight, or about 50% to about 95% by weight. In yet other aspects of this embodiment, a pharmaceutical composition disclosed herein may comprise a pharmaceutically-acceptable room temperature solid lipid (hard fat) in an amount of, e.g., about 70% to about 97% by weight, about 75% to about 97% by weight, about 80% to about 97% by weight, about 85% to about 97% by weight, about 88% to about 97% by weight, about 89% to about 97% by weight, about 90% to about 97% by weight, about 90% to about 97% by weight, about 75% to about 96% by weight, about 80% to about 96% by weight, about 85% to about 96% by weight, about 88% to about 96% by weight, about 89% to about 96% by weight, about 90% to about 96% by weight, about 75% to about 93% by weight, about 80% to about 93% by weight, about 85% to about 93% by weight, about 88% to about 93% by weight, about 89% to about 93% by weight, or about 90% to about 93% by weight.

Commercially available mixtures of pharmaceutically-acceptable glycerolipids include, without limitation, Cocoa butter, mixtures of PEG-6 sterate and ethylene glycol palmitostearate and PEG-32 stearate (TEFOSE® 1500; TEFOSE® 63), mixtures of triceteareth-4 phosphate and ethylene glycol palmitostearate and diethylene glycol palmitostearate (SEDEFOS® 75), mixtures of glycerol monostearate and PEG-75 stearate (GELOT®), mixtures of cetyl alcohol and ethoxylated fatty alcohols (seteth-2-, steareth-20) (EMULCIRE®), mixtures of saturated $C_{10}$-$C_{18}$ triglycerides having a melting point around 33° C. (GELUCIRE® 33/01), mixtures of saturated $C_{10}$-$C_{18}$ triglycerides having a melting point around 39° C. (GELUCIRE® 39/01), mixtures of saturated $C_{10}$-$C_{18}$ triglycerides having a melting point around 43° C. (GELUCIRE® 43/01), mixtures of glycerol monostearate 40-55 (type I) and diglycerides (GELEOL® Mono and Diglycerides), and mixtures of medium-chain triglycerides (LABRAFAC® Lipophile WL 1349).

A hard fat useful in the pharmaceutical compositions disclosed herein may be a pharmaceutically-acceptable glycol fatty acid ester. A pharmaceutically-acceptable glycol fatty acid ester can be a monoester of a glycol, a diester of a glycol, or a triester of a glycol. A glycol fatty acid ester include, without limitation, an ethylene glycol fatty acid ester, a diethylene glycol fatty acid ester, a propylene glycol fatty acid ester, and a dipropylene fatty acid ester. Non-limiting examples of glycol fatty acid esters include, e.g., ethelene glycol caprylate, ethelene glycol pelargonate, ethelene glycol caprate, ethelene glycol undecylate, ethelene glycol laurate, ethelene glycol tridecylate, ethelene glycol myristate, ethelene glycol myristolate, ethelene glycol pentadecyclate, ethelene glycol palmitate, ethelene glycol palmitoleate, ethelene glycol sapienate, ethelene glycol margarate, ethelene glycol stearate, ethelene glycol palmitostearate, ethelene glycol oleate, ethelene glycol elaidate, ethelene glycol vaccinate, ethelene glycol linoleate, ethelene glycol linoelaidate, ethelene glycol α-linolenate, ethelene glycol γ-linolenate, ethelene glycol stearidonate, ethelene glycol capprylocaprate, ethelene glycol dicapprylocaprate, diethelene glycol caprylate, diethelene glycol pelargonate, diethelene glycol caprate, diethelene glycol undecylate, diethelene glycol laurate, diethelene glycol tridecylate, diethelene glycol myristate, diethelene glycol myristolate, diethelene glycol pentadecyclate, diethelene glycol palmitate, diethelene glycol palmitoleate, diethelene glycol sapienate, diethelene glycol margarate, diethelene glycol stearate, diethelene glycol palmitostearate, diethelene glycol oleate, diethelene glycol elaidate, diethelene glycol vaccinate, diethelene glycol linoleate, diethelene glycol linoelaidate, diethelene glycol α-linolenate, diethelene glycol γ-linolenate, diethelene glycol stearidonate, diethelene glycol capprylocaprate, diethelene glycol dicapprylocaprate, propylene glycol caprylate, propylene glycol pelargonate, propylene glycol caprate, propylene glycol undecylate, propylene glycol laurate, propylene glycol tridecylate, propylene glycol myristate, propylene glycol myristolate, propylene glycol pentadecyclate, propylene glycol palmitate, propylene glycol palmitoleate, propylene glycol sapienate, propylene glycol margarate, propylene glycol stearate, propylene glycol palmitostearate, propylene glycol oleate, propylene glycol elaidate, propylene glycol vaccinate, propylene glycol linoleate, propylene glycol linoelaidate, propylene glycol α-linolenate, propylene glycol γ-linolenate, propylene glycol stearidonate, propylene glycol capprylocaprate, propylene glycol dicapprylocaprate, dipropylene glycol caprylate, dipropylene glycol pelargonate, dipropylene glycol caprate, dipropylene glycol undecylate, dipropylene glycol laurate, dipropylene glycol tridecylate, dipropylene glycol myristate, dipropylene glycol myristolate, dipropylene glycol pentadecyclate, dipropylene glycol palmitate, dipropylene glycol palmitoleate, dipropylene glycol sapienate, dipropylene glycol margarate, dipropylene glycol stearate, dipropylene glycol palmitostearate, dipropylene glycol oleate, dipropylene glycol elaidate, dipropylene glycol vaccinate, dipropylene glycol linoleate, dipropylene glycol linoelaidate, dipropylene glycol α-linolenate, dipropylene glycol γ-linolenate, dipropylene glycol stearidonate, dipropylene glycol capprylocaprate, dipropylene glycol dicapprylocaprate, or any combination thereof.

Commercially available pharmaceutically-acceptable glycol fatty acid esters include, without limitation, propylene glycol monopalmitostearate (MONOSTEOL®), propylene glycol dicapprylocaprate (LABRAFAC® PG), propylene glycol monolaurate (type I) (LAUROGLYCOL® FCC), propylene glycol monolaurate (type II) (LAUROGLYCOL® 90), propylene glycol monocaprylate (type I) (CAPRYOL® PGMC), and propylene glycol monocaprylate (type II) (CAPRYOL® 90).

A hard fat useful in the pharmaceutical compositions disclosed herein may be a pharmaceutically-acceptable polyether fatty acid ester. A pharmaceutically-acceptable polyether fatty acid ester can be a mono-fatty acid ester of a polyether, a di-fatty acid ester of a polyether, or a tri-fatty acid ester of a polyether. A polyether fatty acid ester includes, without limitation, a PEG fatty acid ester, a PEG glyceryl fatty acid, a PEG fatty acid ester glyceride, a PPG fatty acid ester, a PPG glyceryl fatty acid, and a PPG fatty acid ester glyceride. A PEG or PPG may be a molecular mass of, e.g., 5-20,000. Non-limiting examples of polyether fatty acid esters include, e.g., a PEG caprylate, a PEG pelargonate, a PEG caprate, a PEG undecylate, a PEG laurate, a PEG tridecylate, a PEG myristate, a PEG myristolate, a PEG pentadecyclate, a PEG palmitate, a PEG palmitoleate, a PEG sapienate, a PEG margarate, a PEG stearate, a PEG palmitostearate, PEG oleate, PEG elaidate, PEG vaccinate, PEG linoleate, PEG linoelaidate, PEG α-linolenate, PEG γ-linolenate, PEG stearidonate, PEG capprylocaprate, PEG dicapprylocaprate, a PEG glyceryl caprylate, a PEG glyceryl pelargonate, a PEG glyceryl caprate, a PEG glyceryl undecylate, a PEG glyceryl laurate, a PEG glyceryl tridecylate, a PEG glyceryl myristate, a PEG glyceryl myristolate, a PEG glyceryl pentadecyclate, a PEG glyceryl palmitate, a PEG glyceryl palmitoleate, a PEG glyceryl sapienate, a PEG glyceryl margarate, a PEG glyceryl stearate, a PEG glyceryl palmitostearate, PEG glyceryl oleate, PEG glyceryl elaidate, PEG glyceryl vaccinate, PEG glyceryl linoleate, PEG glyceryl linoelaidate, PEG glyceryl α-linolenate, PEG glyceryl γ-linolenate, PEG glyceryl stearidonate, PEG glyceryl capprylocaprate, PEG glyceryl dicapprylocaprate, a capryloyl PEG glyceride, a pelargonoyl PEG glyceride, a caproyl PEG glyceride, an undecyloyl PEG glyceride, a lauroyl PEG glyceride, a tridecyloyl PEG glyceride, a myristoyl PEG glyceride, a myristoloyl PEG glyceride, a pentadecycloyl PEG glyceride, a palmitoyl PEG glyceride, a palmitoleoyl PEG glyceride, a sapienoyl PEG glyceride, a margaroyl PEG glyceride, a stearoyl PEG glyceride, a palmitostearoyl PEG glyceride, an oleoyl PEG glyceride, an elaidoyl PEG glyceride, a vaccinoyl PEG glyceride, a linoleoyl PEG glyceride, a linoelaidoyl PEG glyceride, an α-linolenoyl PEG glyceride, a γ-linolenoyl PEG glyceride, a stearidonoyl PEG glyceride, a capprylocaproyl PEG glyceride, a dicapprylocaproyl PEG glyceride, a PPG caprylate, a PPG pelargonate, a PPG caprate, a PPG undecylate, a PPG laurate, a PPG tridecylate, a PPG myristate, a PPG myristolate, a PPG pentadecyclate, a PPG palmitate, a PPG palmitoleate, a PPG sapienate, a PPG margarate, a PPG stearate, a PPG palmitostearate, a PPG oleate, a PPG elaidate, a PPG vaccinate, a PPG linoleate, a PPG linoelaidate, a PPG α-linolenate, a PPG γ-linolenate, a PPG stearidonate, a PPG capprylocaprate, a PPG dicapprylocaprate, a PPG glyceryl caprylate, a PPG glyceryl pelargonate, a PPG glyceryl caprate, a PPG glyceryl undecylate, a PPG glyceryl laurate, a PPG glyceryl tridecylate, a PPG glyceryl myristate, a PPG glyceryl myristolate, a PPG glyceryl pentadecyclate, a PPG glyceryl palmitate, a PPG glyceryl palmitoleate, a PPG glyceryl sapienate, a PPG glyceryl margarate, a PPG glyceryl stearate, a PPG glyceryl palmitostearate, a PPG glyceryl oleate, a PPG glyceryl elaidate, a PPG glyceryl vaccinate, a PPG glyceryl linoleate, a PPG glyceryl linoelaidate, a PPG glyceryl α-linolenate, a PPG glyceryl γ-linolenate, a PPG glyceryl stearidonate, a PPG glyceryl capprylocaprate, a PPG glyceryl dicapprylocaprate, a capryloyl PPG glyceride, a pelargonoyl PPG glyceride, a caproyl PPG glyceride, an undecyloyl PPG glyceride, a lauroyl PPG glyceride, a tridecyloyl PPG glyceride, a myristoyl PPG glyceride, a myristoloyl PPG glyceride, a pentadecycloyl PPG glyceride, a palmitoyl PPG glyceride, a palmitoleoyl PPG glyceride, a sapienoyl PPG glyceride, a margaroyl PPG glyceride, a stearoyl PPG glyceride, a palmitostearoyl PPG glyceride, an oleoyl PPG glyceride, an elaidoyl PPG glyceride, a vaccinoyl PPG glyceride, a linoleoyl PPG glyceride, a linoelaidoyl PPG glyceride, an α-linolenoyl PPG glyceride, a γ-linolenoyl PPG glyceride, a stearidonoyl PPG glyceride, a capprylocaproyl PPG glyceride, a dicapprylocaproyl PPG glyceride, or any combination thereof.

Commercially available pharmaceutically-acceptable polyether fatty acid esters include, without limitation, caprylocaproyl macrogol-8 glycerides (LABRASOL®), PEG-8 beeswax (APIFIL®), lauroyl macrogol-32 glycerides (GELUCIRE 44/14), stearoyl macrogol-32 glycerides (GELUCIRE 50.13), linoleoyl macrogol-6 glycerides (LABRAFIL® M2125CS), oleoyl macrogol-6 glycerides (LABRAFIL® M1944CS), and lauroyl macrogol-6 glycerides (LABRAFIL® M2130CS).

Another lipid useful in the pharmaceutical compositions disclosed herein may be a pharmaceutically-acceptable room temperature liquid lipid. Also known as a "liquid fat", a room temperature liquid lipid includes any fatty acid that is liquid at normal room temperature, such as, e.g. about 20° C. Room temperature liquid lipid comprise a wide group of compounds that are generally soluble in organic solvents and generally insoluble in water. Examples of mixtures of pharmaceutically-acceptable room temperature liquid lipids include, without limitation, a mixture of one or more fatty acids disclosed herein, a mixture of one or more partially hydrolyzed fat, and a mixture of one or more partially hydrogenated fat.

A pharmaceutically-acceptable room temperature liquid lipid includes a pharmaceutically-acceptable partially hydrogenated fat. The process of hydrogenation adds hydrogen atoms to unsaturated lipid, eliminating double bonds and making them into partially or completely saturated lipid.

Partial hydrogenation is a chemical rather than enzymatic, that converts a part of cis-isomers into trans-unsaturated lipids instead of hydrogenating them completely. In the first reaction step, one hydrogen is added, with the other, coordinatively unsaturated, carbon being attached to the catalyst. The second step is the addition of hydrogen to the remaining carbon, producing a saturated fatty acid. The first step is reversible, such that the hydrogen is readsorbed on the catalyst and the double bond is re-formed. The intermediate with only one hydrogen added contains no double bond and can freely rotate. Thus, the double bond can re-form as either cis or trans, of which trans is favored, regardless the starting material.

A solid solution pharmaceutical composition disclosed herein may comprise a room temperature liquid lipid in an amount sufficient to dissolve a therapeutic compound disclosed herein. In other aspects of this embodiment, a pharmaceutical composition disclosed herein may comprise a room temperature liquid lipid in an amount of, e.g., less than about 90% by weight, less than about 80% by weight, less than about 70% by weight, less than about 65% by weight, less than about 60% by weight, less than about 55% by weight, less than about 50% by weight, less than about 45% by weight, less than about 40% by weight, less than about 35% by weight, less than about 30% by weight, less than about 25% by weight, less than about 20% by weight, less than about 15% by weight, less than about 10% by weight, less than about 5% by weight, or less than about 1% by weight. In other aspects of this embodiment, a pharmaceutical composition disclosed herein may comprise a room temperature liquid lipid in an amount in a range of, e.g., about 1% to 90% by weight, about 1% to 80% by weight, about 1% to 70% by weight, about 1% to 60% by weight, about 1% to 50% by weight, about 1% to 40% by weight, about 1% to 30% by weight, about 1% to 20% by weight, about 1% to 10% by weight, about 2% to 50% by weight, about 2% to 40% by weight, about 2% to 30% by weight, about 2% to 20% by weight, about 2% to 10% by weight, about 4% to 50% by weight, about 4% to 40% by weight, about 4% to 30% by weight, about 4% to 20% by weight, about 4% to 10% by weight, about 6% to 50% by weight, about 6% to 40% by weight, about 6% to 30% by weight, about 6% to 20% by weight, about 6% to 10% by weight, about 8% to 50% by weight, about 8% to 40% by weight, about 8% to 30% by weight, about 8% to 20% by weight, about 8% to 15% by weight, or about 8% to 12% by weight.

Examples of a pharmaceutically-acceptable room temperature liquid lipids include monoglycerides including, without limitation, glycerol monomyristoleate, glycerol monopalmitoleate, glycerol monosapienate, glycerol monooleate, glycerol monoelaidate, glycerol monovaccenate, glycerol monolinoleate, glycerol monolinoelaidate, glycerol monolinolenate, glycerol monostearidonate, glycerol monoeicosenoate, glycerol monomeadate, glycerol monoarachidonate, glycerol monoeicosapentaenoate, glycerol monoerucate, glycerol monodocosahexaenoate, and glycerol mononervonate.

Commercially available pharmaceutically-acceptable room temperature liquid lipids include, without limitation, glyceryl dibehenate (COMPRITOL® 888), glycerol behenate (COMPRITOL® E ATO), glycerol dipalmitostearate (Biogapress Vegetal BM297ATO), glycerol distearate (type I) (PRECIROL® ATO 5), and glycerol monolinoleate (MAISINE™ 35-1).

Aspects of the present specification disclose, in part, a stabilizing agent. A stability agent is a compound that interacts with a free acid or base present on a therapeutic compound disclosed herein to shield the charges, thereby impeding ionic interactions between therapeutic compound/lipid matrices preventing the alignments necessary to form a crystalline matrix of a solid phase composition. Thus, a stabilizing agent prevent the thermodynamic transition of a composition into a classic solid phase or prolongs this transition to such an extent that it does not occur. Examples of stability agents include a liquid glycol polymer, a monohydric alcohol, isosorbide dimethyl ether, and diethylene glycol monoethyl ether (2-(2-ethoxyethoxy)ethanol) (TRANSCUTOL®).

A pharmaceutical composition disclosed herein may comprise a stabilizing agent in an amount sufficient to stabilize the free acid or base present in a therapeutic compound disclosed herein. In other aspects of this embodiment, a pharmaceutical composition disclosed herein may comprise a stabilizing agent in an amount of, e.g., less than about 40% by weight, less than about 35% by weight, less than about 30% by weight, less than about 25% by weight, less than about 20% by weight, less than about 19% by weight, less than about 18% by weight, less than about 17% by weight, less than about 16% by weight, less than about 15% by weight, less than about 14% by weight, less than about 13% by weight, less than about 12% by weight, less than about 11% by weight, less than about 10% by weight, less than about 9% by weight, less than about 8% by weight, less than about 7% by weight, less than about 6% by weight, less than about 5% by weight, less than about 4% by weight, less than about 3% by weight, less than about 2% by weight, or less than about 1%. In other aspects of this embodiment, a pharmaceutical composition disclosed herein may comprise a stabilizing agent in an amount of, e.g., about 1% to about 5% by weight, about 1% to about 7% by weight, about 1% to about 10% by weight, about 1% to about 12% by weight, about 1% to about 15% by weight, about 1% to about 18% by weight, about 1% to about 20% by weight, about 2% to about 5% by weight, about 2% to about 7% by weight, about 2% to about 10% by weight, about 2% to about 12% by weight, about 2% to about 15% by weight, about 2% to about 18% by weight, about 2% to about 20% by weight, about 3% to about 5% by weight, about 3% to about 7% by weight, about 3% to about 10% by weight, about 3% to about 12% by weight, about 3% to about 15% by weight, about 3% to about 18% by weight, about 3% to about 20% by weight, about 4% to about 5% by weight, about 4% to about 7% by weight, about 4% to about 10% by weight, about 4% to about 12% by weight, about 4% to about 15% by weight, about 4% to about 18% by weight, about 4% to about 20% by weight, about 5% to about 7% by weight, about 5% to about 10% by weight, about 5% to about 12% by weight, about 5% to about 15% by weight, about 5% to about 18% by weight, about 5% to about 20% by weight, about 6% to about 7% by weight, about 6% to about 10% by weight, about 6% to about 12% by weight, about 6% to about 15% by weight, about 6% to about 18% by weight, about 6% to about 20% by weight, about 7% to about 10% by weight, about 7% to about 12% by weight, about 7% to about 15% by weight, about 7% to about 18% by weight, about 7% to about 20% by weight, about 8% to about 10% by weight, about 8% to about 12% by weight, about 8% to about 15% by weight, about 8% to about 18% by weight, about 8% to about 20% by weight, about 9% to about 10% by weight, about 9% to about 12% by weight, about 9% to about 15% by weight, about 9% to about 18% by weight, about 9% to about 20% by weight, about 10% to about 12% by weight, about 10% to about 15% by weight, about 10% to about 18% by weight, or about 10% to about 20% by weight.

A stability agent as disclosed herein is not a solvent as it is used in an amount that does not result in substantial dissolving of a solute. As such, the amount stability agent used in a solid solution composition disclosed herein results in no more than 85% dissolution of a therapeutic compound disclosed herein. In aspects of this embodiment, the amount stability agent used in a solid solution composition disclosed herein results in. e.g., no more than 80%, no more than 75%, no more than 70%, no more than 65%, no more than 60%, no more than 55%, no more than 50%, no more than 45%, no more than 40%, no more than 35%, no more than 30%, no more than 25%, no more than 20%, no more than 15%, no more than 10%, or no more than 5% dissolution of a therapeutic compound disclosed herein.

In an embodiment, a glycol polymer may comprise a pharmaceutically-acceptable PEG polymer. PEG polymers, also known as polyethylene oxide (PEO) polymers or polyoxyethylene (POE) polymers, are prepared by polymerization of ethylene oxide and are commercially available over a wide range of molecular weights from 100 g/mol to 10,000,000 g/mol. PEG polymers with a low molecular mass are liquids or low-melting solids, whereas PEG polymers of a higher molecular mass are solids. In an aspect of this embodiment, a PEG polymer used as a stability agent is a liquid PEG polymer. In aspects of this embodiment, a PEG polymer has a molecular weight of, e.g., no more than 100 g/mol, no more than 200 g/mol, no more than 300 g/mol, no more than 400 g/mol, no more than 500 g/mol, no more than 600 g/mol, no more than 700 g/mol, no more than 800 g/mol, no more than 900 g/mol, or no more than 1000 g/mol.

A PEG polymer include, without limitation, PEG 100, PEG 200, PEG 300, PEG 400, PEG 500, PEG 600, PEG 700, PEG 800, PEG 900, PEG 1000, PEG 1100, PEG 1200, PEG 1300, PEG 1400, PEG 1500, PEG 1600, PEG 1700, PEG 1800, PEG 1900, PEG 2000, PEG 2100, PEG 2200, PEG 2300, PEG 2400, PEG 2500, PEG 2600, PEG 2700, PEG 2800, PEG 2900, PEG 3000, PEG 3250, PEG 3350, PEG 3500, PEG 3750, PEG 4000, PEG 4250, PEG 4500, PEG 4750, PEG 5000, PEG 5500, PEG 6000, PEG 6500, PEG 7000, PEG 7500, PEG 8000, PEG 8500, PEG 9000, PEG 9500, PEG 10,000, PEG 11,000, PEG 12,000, PEG 13,000, PEG 14,000, PEG 15,000, PEG 16,000, PEG 17,000, PEG 18,000, PEG 19,000, or PEG 20,000.

In another embodiment, a glycol polymer may comprise a pharmaceutically-acceptable polypropylene glycol (PPG) polymer. PPG polymers, also known as polypropylene oxide (PPO) polymers or polyoxypropylene (POP) polymers, are prepared by polymerization of propylene oxide and are commercially available over a wide range of molecular weights from 100 g/mol to 10,000,000 g/mol. PPG polymers with a low molecular mass are liquids or low-melting solids, whereas PPG polymers of a higher molecular mass are solids. In an aspect of this embodiment, a PPG polymer used as a stability agent is a liquid PPG polymer. In aspects of this embodiment, a PPG polymer has a molecular weight of, e.g., no more than 100 g/mol, no more than 200 g/mol, no more than 300 g/mol, no more than 400 g/mol, no more than 500 g/mol, no more than 600 g/mol, no more than 700 g/mol, no more than 800 g/mol, no more than 900 g/mol, or no more than 1000 g/mol.

A PPG polymer include, without limitation, PPG 100, PPG 200, PPG 300, PPG 400, PPG 500, PPG 600, PPG 700, PPG 800, PPG 900, PPG 1000, PPG 1100, PPG 1200, PPG 1300, PPG 1400, PPG 1500, PPG 1600, PPG 1700, PPG 1800, PPG 1900, PPG 2000, PPG 2100, PPG 2200, PPG 2300, PPG 2400, PPG 2500, PPG 2600, PPG 2700, PPG 2800, PPG 2900, PPG 3000, PPG 3250, PPG 3350, PPG 3500, PPG 3750, PPG 4000, PPG 4250, PPG 4500, PPG 4750, PPG 5000, PPG 5500, PPG 6000, PPG 6500, PPG 7000, PPG 7500, PPG 8000, PPG 8500, PPG 9000, PPG 9500, PPG 10,000, PPG 11,000, PPG 12,000, PPG 13,000, PPG 14,000, PPG 15,000, PPG 16,000, PPG 17,000, PPG 18,000, PPG 19,000, or PPG 20,000.

A monohydric alcohol may also be used as a stability agent. In aspects of this embodiment, the monohydric alcohol may be, e.g., a $C_{2-4}$ alcohol, a $C_{1-4}$ alcohol, a $C_{1-5}$ alcohol, a $C_{1-7}$ alcohol, a $C_{1-10}$ alcohol, a $C_{1-15}$ alcohol, or a $C_{1-20}$ alcohol. Examples of a monohydric alcohol include, without limitation, methanol, ethanol, propanol, butanol, pentanol, and 1-hexadecanol.

Aspects of the present specification disclose, in part, a neutralizing agent. A neutralizing agent is a compound that interacts with a therapeutic compound disclosed herein that is a salt to neutralized the ionic charges produced when the therapeutic compound dissolves, thereby impeding ionic interactions between therapeutic compound/lipid matrices preventing the alignments necessary to form a crystalline matrix of a solid phase composition. Thus, a neutralizing agent prevent the thermodynamic transition of a composition into a classic solid phase or prolongs this transition to such an extent that it does not occur. Examples of neutralizing agents include fatty acids as disclosed herein for base-salt drugs and sodium acetate or triethanolamine for acid-salt drugs.

The amount of neutralizing agent used is based upon the extent of charge neutralization desired. For complete neutralization, one molar equivalent of neutralizing agent relative to therapeutic compound is added to the formulation. For partial neutralization, less than one molar equivalent is added. Partial neutralization is advantageous in producing a sustained release formulation. Upon administration, a portion of the therapeutic compound is immediately made available to the body (instant bioavailability) while the bioavailability of another portion is delayed until the therapeutic compound is neutralized by the neutralizing agent. A neutralizing agent may also be added in an excessive amount, i.e., more than one molar equivalent relative to therapeutic compound. Besides neutralizing the salt-drug, excessive amounts of neutralizing agent can also enable adjustments to the melting point of the solid solution composition.

In aspects of this embodiment, a pharmaceutical composition disclosed herein may comprise a neutralizing agent in an amount of, e.g., at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, or at least 100 mg. In other aspects of this embodiment, a pharmaceutical composition disclosed herein may comprise a neutralizing agent in an amount of, e.g., at least 5 mg, at least 10 mg, at least 20 mg, at least 25 mg, at least 50 mg, at least 75 mg, at least 100 mg, at least 200 mg, at least 300 mg, at least 400 mg, at least 500 mg, at least 600 mg, at least 700 mg, at least 800 mg, at least 900 mg, at least 1,000 mg, at least 1,100 mg, at least 1,200 mg, at least 1,300 mg, at least 1,400 mg, or at least 1,500 mg. In yet other aspects of this embodiment, a pharmaceutical composition disclosed herein may comprise a neutralizing agent in an amount of, e.g., about 5 mg to about 100 mg, about 10 mg to about 100 mg, about 50 mg to about 150 mg, about 100 mg to about 250 mg, about 150 mg to about 350 mg, about 250 mg to about 500 mg, about 350 mg to about 600 mg, about 500 mg to about 750 mg, about 600 mg to about 900 mg, about 750 mg to about 1,000 mg, about 850 mg to about 1,200 mg, or about 1,000 mg to about 1,500 mg. In still other aspects of this embodiment, a pharmaceutical composition disclosed herein may comprise a neutralizing agent in an amount of, e.g., about 10 mg to about 250 mg, about 10 mg to about 500 mg, about 10 mg to about 750 mg, about 10 mg to about 1,000 mg, about 10 mg to about 1,500 mg, about 50 mg to about 250 mg, about 50 mg to about 500 mg, about 50 mg to about 750 mg, about 50 mg to about 1,000 mg, about 50 mg to about 1,500 mg, about 100 mg to about 250 mg, about 100 mg to about 500 mg, about 100 mg to about 750 mg, about 100 mg to about 1,000 mg, about 100 mg to about 1,500 mg, about 200 mg to about 500 mg, about 200 mg to about 750 mg, about 200 mg to about 1,000 mg, about 200 mg to about 1,500 mg, about 5 mg to about 1,500 mg, about 5 mg to about 1,000 mg, or about 5 mg to about 250 mg.

In other aspects of this embodiment, a pharmaceutical composition disclosed herein may comprise a neutralizing agent in an amount of, e.g., less than about 90% by weight, less than about 80% by weight, less than about 70% by weight, less than about 65% by weight, less than about 60% by weight, less than about 55% by weight, less than about 50% by weight, less than about 45% by weight, less than about 40% by weight, less than about 35% by weight, less than about 30% by weight, less than about 25% by weight, less than about 20% by weight, less than about 15% by weight, less than about 10% by weight, less than about 5% by weight, or less than about 1% by weight. In other aspects of this embodiment, a pharmaceutical composition disclosed herein may comprise a neutralizing agent in an amount of, e.g., about 1% to 90% by weight, about 1% to 80% by weight, about 1% to 75% by weight, about 1% to 70% by weight, about 1% to 65% by weight, about 1% to 60% by weight, about 1% to 55% by weight, about 1% to 50% by weight, about 1% to 45% by weight, about 1% to 40% by weight, about 1% to 35% by weight, about 1% to 30% by weight, about 1% to 25% by weight, about 1% to 20% by weight, about 1% to 15% by weight, about 1% to 10% by weight, about 1% to 5% by weight, about 2% to 50% by weight, about 2% to 40% by weight, about 2% to 30% by weight, about 2% to 20% by weight, about 2% to 10% by weight, about 4% to 50% by weight, about 4% to 40% by weight, about 4% to 30% by weight, about 4% to 20% by weight, about 4% to 10% by weight, about 6% to 50% by weight, about 6% to 40% by weight, about 6% to 30% by weight, about 6% to 20% by weight, about 6% to 10% by weight, about 8% to 50% by weight, about 8% to 40% by weight, about 8% to 30% by weight, about 8% to 20% by weight, about 8% to 15% by weight, or about 8% to 12% by weight.

In other aspects of this embodiment, a pharmaceutical composition disclosed herein may comprise a neutralizing agent in an amount of, e.g., about 0.1% to about 45% by weight, about 0.1% to about 40% by weight, about 0.1% to about 35% by weight, about 0.1% to about 30% by weight, about 0.1% to about 25% by weight, about 0.1% to about 20% by weight, about 0.1% to about 15% by weight, about 0.1% to about 10% by weight, about 0.1% to about 5% by weight, about 1% to about 45% by weight, about 1% to about 40% by weight, about 1% to about 35% by weight, about 1% to about 30% by weight, about 1% to about 25% by weight, about 1% to about 20% by weight, about 1% to about 15% by weight, about 1% to about 10% by weight, about 1% to about 5% by weight, about 5% to about 45% by weight, about 5% to about 40% by weight, about 5% to about 35% by weight, about 5% to about 30% by weight, about 5% to about 25% by weight, about 5% to about 20% by weight, about 5% to about 15% by weight, about 5% to about 10% by weight, about 10% to about 45% by weight, about 10% to about 40% by weight, about 10% to about 35% by weight, about 10% to about 30% by weight, about 10% to about 25% by weight, about 10% to about 20% by weight, about 10% to about 15% by weight, about 15% to about 45% by weight, about 15% to about 40% by weight, about 15% to about 35% by weight, about 15% to about 30% by weight, about 15% to about 25% by weight, about 15% to about 20% by weight, about 20% to about 45% by weight, about 20% to about 40% by weight, about 20% to about 35% by weight, about 20% to about 30% by weight, about 20% to about 25% by weight, about 25% to about 45% by weight, about 25% to about 40% by weight, about 25% to about 35% by weight, or about 25% to about 30% by weight.

A pharmaceutical composition disclosed herein may optionally include a pharmaceutically-acceptable carrier that facilitates processing of an active ingredient into pharmaceutically-acceptable compositions. As used herein, the term "pharmacologically-acceptable carrier" is synonymous with "pharmacological carrier" and means any carrier that has substantially no long term or permanent detrimental effect when administered and encompasses terms such as "pharmacologically acceptable vehicle, stabilizer, diluent, additive, auxiliary or excipient." Such a carrier generally is mixed with an active compound or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in Pharmaceutical Dosage Forms and Drug Delivery Systems (Howard C. Ansel et al., eds., Lippincott Williams & Wilkins Publishers, 7th ed. 1999); REMINGTON: THE SCIENCE AND PRACTICE OF PHARMACY (Alfonso R. Gennaro ed., Lippincott, Williams & Wilkins, 20th ed. 2000); Goodman & Gilman's The Pharmacological Basis of Therapeutics (Joel G. Hardman et al., eds., McGraw-Hill Professional, 10th ed. 2001); and Handbook of Pharmaceutical Excipients (Raymond C. Rowe et al., APhA Publications, 4th edition 2003). These protocols are routine procedures and any modifications are well within the scope of one skilled in the art and from the teaching herein.

A pharmaceutical composition disclosed herein can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed herein, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition.

In an embodiment, a pharmaceutical composition disclosed herein is solid at room temperature. In aspects of this embodiment, a pharmaceutical composition disclosed herein may be formulated to be a solid at a temperature of, e.g., about 35° C. or lower, about 34° C. or lower, about 33° C. or lower, about 32° C. or lower, about 31° C. or lower, about 30° C. or lower, about 29° C. or lower, about 28° C. or lower, about 27° C. or lower, about 26° C. or lower, about 25° C. or lower, about 24° C. or lower, about 23° C. or lower, about 22° C. or lower, about 21° C. or lower, about 20° C. or lower, about 19° C. or lower, about 18° C. or lower, about 17° C. or lower, about 16° C. or lower, about 15° C. or lower, about 14° C. or lower, about 13° C. or lower, about 12° C. or lower, about 11° C. or lower, about 10° C. or lower, about 9° C. or lower, about 8° C. or lower, about 7° C. or lower, about 6° C. or lower, about 5° C. or lower, about 4° C. or lower, about 3° C. or lower, about 2° C. or lower, about 1° C. or lower, or about 0° C. or lower.

In other aspects of this embodiment, a pharmaceutical composition disclosed has a melting point temperature of, e.g., 5° C. or higher, 10° C. or higher, 15° C. or higher, 16° C. or higher, 17° C. or higher, 18° C. or higher, 19° C. or higher, 20° C. or higher, 21° C. or higher, 22° C. or higher, 23° C. or higher, 24° C. or higher, 25° C. or higher, 26° C. or higher, 27° C. or higher, 28° C. or higher, 29° C. or higher, 30° C. or higher, 31° C. or higher, 32° C. or higher, 33° C. or higher, 34° C. or higher, 35° C. or higher, 36° C. or higher, or 37° C. or higher. In other aspects of this embodiment, a pharmaceutical composition disclosed has a melting point temperature in the range of, e.g., about 5° C. to about 24° C., about 10° C. to about 24° C. about 22° C. to about 24° C., about 23° C. to about 25° C., about 24° C. to about 26° C., about 25° C. to about 27° C., about 26° C. to about 28° C., about 27° C. to about 29° C., about 28° C. to about 30° C., about 29° C. to about 31° C., about 30° C. to about 32° C., about 31° C. to about 33° C., about 32° C. to about 34° C., about 33° C. to about 35° C., about 34° C. to about 36° C., or about 35° C. to about 37° C. In other aspects of this embodiment, a pharmaceutical composition disclosed has a melting point temperature in the range of, e.g., about 22° C. to about 26° C., about 24° C. to about 28° C., about 26° C. to about 30° C., about 28° C. to about 32° C., about 30° C. to about 34° C., about 32° C. to about 36° C., or about 34° C. to about 38° C.

Aspects of the present specification disclose, in part, a method of preparing a solid solution pharmaceutical composition disclosed herein. In one embodiment, a method disclosed herein comprises the steps of a) contacting a therapeutic compound disclosed herein with one or more room temperature liquid lipids under conditions which allow the therapeutic compound to dissolve in the one or more lipids; and b) contacting the compound/lipid solution with one or more room temperature solid lipids disclosed herein under conditions which allow the formation of a solid solution composition.

In one embodiment, a method disclosed herein comprises the steps of a) contacting a therapeutic compound disclosed herein with one or more room temperature liquid lipids and one or more stabilizing agents under conditions which allow the therapeutic compound to dissolve in the one or more lipids; and b) contacting the compound/lipid solution with one or more room temperature solid lipids disclosed herein under conditions which allow the formation of a solid solution composition.

In one embodiment, a method disclosed herein comprises the steps of a) contacting a therapeutic compound disclosed herein with one or more room temperature liquid lipids and one or more neutralizing agents under conditions which allow the therapeutic compound to dissolve in the one or more lipids; and b) contacting the compound/lipid solution with one or more room temperature solid lipids disclosed herein under conditions which allow the formation of a solid solution composition.

In one embodiment, a method disclosed herein comprises the steps of a) contacting a therapeutic compound disclosed herein with one or more room temperature liquid lipids, one or more stabilizing agents, and one or more neutralizing agents under conditions which allow the therapeutic compound to dissolve in the one or more lipids; and b) contacting the compound/lipid solution with one or more room temperature solid lipids disclosed herein under conditions which allow the formation of a solid solution composition.

The method disclosed herein is carried out under conditions which allow the therapeutic compound to dissolve in other components. In aspects of this embodiment, a method disclosed herein may be carried out at a temperature sufficient to dissolve the therapeutic compound into the one or more room temperature liquid lipids, and/or one or more stabilizing agents, and/or one or more neutralizing agents to create a solution. In other aspects of this embodiment, a method disclosed herein comprises heating a mixture comprising a therapeutic compound disclosed herein to a temperature of, e.g., about 40° C., about 45° C., about 50° C., about 55° C., about 60° C., about 65° C., about 70° C., or about 75° C. In yet other aspects of this embodiment, a method disclosed herein comprises heating a mixture comprising a therapeutic compound disclosed herein to a temperature of, e.g., at least 40° C., at least 45° C., at least 50° C., at least 55° C., at least 60° C., at least 65° C., at least 70° C., or at least 75° C. In still other aspects of this embodiment, a method disclosed herein comprises heating a mixture comprising a therapeutic compound disclosed herein to a temperature of, e.g., at most 40° C., at most 45° C., at most 50° C., at most 55° C., at most 60° C., at most 65° C., at most 70° C., or at most 75° C. In other aspects of this embodiment, a method disclosed herein comprises heating a mixture comprising a therapeutic compound disclosed herein to a temperature of, e.g., about 40° C. to about 45° C., about 40° C. to about 50° C., about 40° C. to about 55° C., about 40° C. to about 60° C., about 40° C. to about 65° C., about 40° C. to about 70° C., about 40° C. to about 75° C., about 45° C. to about 50° C., about 45° C. to about 55° C., about 45° C. to about 60° C., about 45° C. to about 65° C., about 45° C. to about 70° C., about 45° C. to about 75° C., about 50° C. to about 55° C., about 50° C. to about 60° C., about 50° C. to about 65° C., about 50° C. to about 70° C., about 50° C. to about 75° C., about 55° C. to about 60° C., about 55° C. to about 65° C., about 55° C. to about 70° C., about 55° C. to about 75° C., about 60° C. to about 65° C., about 60° C. to about 70° C., about 60° C. to about 75° C., about 65° C. to about 70° C., about 65° C. to about 75° C., or about 70° C. to about 75° C.

In other aspects of this embodiment, a method disclosed herein may be carried out at a temperature sufficient to incorporate the one or more room temperature solid lipids into the solution comprising the therapeutic compound. In other aspects of this embodiment, a method disclosed herein comprises heating a mixture comprising a therapeutic compound disclosed herein to a temperature of, e.g., about 40° C., about 45° C., about 50° C., about 55° C., about 60° C., about 65° C., about 70° C., or about 75° C. in order to incorporate the one or more room temperature solid lipids. In yet other aspects of this embodiment, a method disclosed herein comprises heating a mixture comprising a therapeutic compound disclosed herein to a temperature of, e.g., at least 40° C., at least 45° C., at least 50° C., at least 55° C., at least 60° C., at least 65° C., at least 70° C., or at least 75° C. in order to incorporate the one or more room temperature solid lipids. In still other aspects of this embodiment, a method disclosed herein comprises heating a mixture comprising a therapeutic compound disclosed herein to a temperature of, e.g., at most 40° C., at most 45° C., at most 50° C., at most 55° C., at most 60° C., at most 65° C., at most 70° C., or at most 75° C. in order to incorporate the one or more room temperature solid lipids. In other aspects of this embodiment, a method disclosed herein comprises heating a mixture comprising a therapeutic compound disclosed herein to a temperature of, e.g., about 40° C. to about 45° C., about 40° C. to about 50° C., about 40° C. to about 55° C., about 40° C. to about 60° C., about 40° C. to about 65° C., about 40° C. to about 70° C., about 40° C. to about 75° C., about 45° C. to about 50° C., about 45° C. to about 55° C., about 45° C. to about 60° C., about 45° C. to about 65° C., about 45° C. to about 70° C., about 45° C. to about 75° C., about 50° C. to about 55° C., about 50° C. to about 60° C., about 50° C. to about 65° C., about 50° C. to about 70° C., about 50° C. to about 75° C., about 55° C. to about 60° C., about 55° C. to about 65° C., about 55° C. to about 70° C., about 55° C. to about 75° C., about 60° C. to about 65° C., about 60° C. to about 70° C., about 60° C. to about 75° C., about 65° C. to about 70° C., about 65° C. to about 75° C., or about 70° C. to about 75° C. in order to incorporate the one or more room temperature solid lipids.

Aspects of the present specification disclose, in part, contacting a therapeutic compound disclosed herein with one or more lipids. In aspects of this embodiment, one or more lipids includes one, two, three, four, or five different lipids disclosed herein. In other aspects of this embodiment, one or more lipids includes two or more, three or more, four or more, or five or more different lipids disclosed herein. In yet other aspects of this embodiment, one or more lipids includes about one to about five different lipids disclosed herein, about two to about five different lipids disclosed herein, about three to about five different lipids disclosed herein, about one to about four different lipids disclosed herein, about two to about four different lipids disclosed herein, or about two to about three different lipids disclosed herein.

In other aspects of this embodiment, one or more lipids includes one or more room temperature solid lipids and one or more room temperature liquid lipids. In aspects of this embodiment, one or more lipids includes one, two, three, four, or five different hard fats disclosed herein and one, two, three, four, or five different room temperature liquid lipids disclosed herein. In other aspects of this embodiment, one or more lipids includes two or more, three or more, four or more, or five or more different room temperature solid lipids disclosed herein and two or more, three or more, four or more, or five or more different room temperature liquid lipids disclosed herein. In yet other aspects of this embodiment, one or more lipids includes about one to about five different hard fats disclosed herein, about two to about five different room temperature solid lipids disclosed herein, about three to about five different room temperature solid lipids disclosed herein, about one to about four different room temperature solid lipids disclosed herein, about two to about four different room temperature solid lipids disclosed herein, or about two to about three different room temperature solid lipids disclosed herein and about one to about five different room temperature liquid lipids disclosed herein, about two to about five different room temperature liquid lipids disclosed herein, about three to about five different room temperature liquid lipids disclosed herein, about one to about four different room temperature liquid lipids disclosed herein, about two to about four different room temperature liquid lipids disclosed herein, or about two to about three different room temperature liquid lipids disclosed herein.

In aspects of this embodiment, the method disclosed herein may use a room temperature solid lipid and a room temperature liquid lipid in a ratio of solid lipid:liquid lipid of, e.g., at least 1:1, at least 2:1, at least 3:1, at least 4:1, at least 5:1, at least 6:1, at least 7:1, at least 8:1, at least 9:1, at least 10:1, at least 15:1, or at least 20:1. In other aspects of this embodiment, the method disclosed herein may use a room temperature solid lipid and a room temperature liquid lipid in a ratio of solid lipid:liquid lipid of, e.g., about 1:1 to about 20:1, about 5:1 to about 20:1, about 2:1 to about 15:1, about 5:1 to about 15:1, about 4:1 to about 12:1, or about 6:1 to about 10:1.

In aspects of this embodiment, the method disclosed herein may use a plurality of room temperature solid lipids and a plurality of room temperature liquid lipids in a ratio of total solid lipid:total liquid lipid of, e.g., at least 1:1, at least 2:1, at least 3:1, at least 4:1, at least 5:1, at least 6:1, at least 7:1, at least 8:1, at least 9:1, at least 10:1, at least 15:1, or at least 20:1. In other aspects of this embodiment, the method disclosed herein may use a plurality of room temperature solid lipids and a plurality of room temperature liquid lipid in a ratio of total solid lipid:total liquid lipid of, e.g., about 1:1 to about 20:1, about 5:1 to about 20:1, about 2:1 to about 15:1, about 5:1 to about 15:1, about 4:1 to about 12:1, or about 6:1 to about 10:1.

The contacting a therapeutic compound and one or more lipids may comprise mixing the, e.g., by stirring, inversion, sonication, or vortexing. The mixing may be carried out for, e.g., at least 1 second, at least 5 seconds, at least 10 seconds, at least 20 seconds, at least 30 seconds, at least 45 seconds, at least 60 seconds, or more, until the therapeutic compound is fully dissolved in the lipid/glycol polymer mixture.

Aspects of the present specification disclose, in part, contacting the compound/lipid solution with one or more glycol polymers disclosed herein.

The method disclosed herein is carried out under conditions which allow the solidification of a solid solution composition. In aspects of this embodiment, the method may be carried out at a temperature sufficient to cool the composition to a temperature where the solution solidifies.

In certain embodiments, a rapid cooling step may be used to reduce the temperature of a pharmaceutical composition disclosed herein after its formation. For example, a rapid cooling step may be used in procedures were temperatures greater than room temperature are used to allow a therapeutic compound to dissolve fully in the pharmaceutically-acceptable solvent and/or to allow the solution comprising the therapeutic compound to form the pharmaceutical composition. In aspects of this embodiment, a rapid cooling step results in a temperature decrease of, e.g., about 30° C. in 20 minutes, about 25° C. in 20 minutes, about 20° C. in 20 minutes, about 15° C. in 20 minutes, about 30° C. in 15 minutes, about 25° C. in 15 minutes, about 20° C. in 15 minutes, about 15° C. in 15 minutes, about 30° C. in 10 minutes, about 25° C. in 10 minutes, about 20° C. in 10 minutes, about 15° C. in 10 minutes, about 30° C. in 5 minutes, about 25° C. in 5 minutes, about 20° C. in 5 minutes, about 15° C. in 5 minutes. In other aspects of this embodiment, a rapid cooling step results in a temperature decrease of, e.g., about 20° C. to about 30° C. in 20 minutes, about 20° C. to about 30° C. in 15 minutes, about 20° C. to about 30° C. in 10 minutes, about 20° C. to about 30° C. in 5 minutes, about 15° C. to about 25° C. in 20 minutes, about 15° C. to about 25° C. in 15 minutes, about 15° C. to about 25° C. in 10 minutes, about 15° C. to about 25° C. in 5 minutes, about 10° C. to about 20° C. in 20 minutes, about 10° C. to about 20° C. in 15 minutes, about 10° C. to about 20° C. in 10 minutes, or about 10° C. to about 20° C. in 5 minutes.

In yet aspects of this embodiment, a rapid cooling step results in a temperature decrease of, e.g., about 2.0° C./minute, about 1.9° C./minute, about 1.8° C./minute, about 1.7° C./minute, about 1.6° C./minute, about 1.5° C./minute, about 1.4° C./minute, about 1.3° C./minute, about 1.2° C./minute, about 1.1° C./minute, about 1.0° C./minute, about 0.9° C./minute, about 0.8° C./minute, about 0.7° C./minute, about 0.6° C./minute, about 0.5° C./minute, about 0.4° C./minute, about 0.3° C./minute, about 0.2° C./minute, or about 0.1° C./minute. In still aspects of this embodiment, a rapid cooling step results in a temperature decrease of, e.g., about 0.1° C. to about 0.4° C./minute, about 0.2° C. to about 0.6° C./minute, about 0.4° C. to about 0.8° C./minute, about 0.6° C. to about 1.0° C./minute, about 0.8° C. to about 1.2° C./minute, about 1.0° C. to about 1.4° C./minute, about 1.2° C. to about 1.6° C./minute, about 1.4° C. to about 1.8° C./minute, about 1.6° C. to about 2.0° C./minute, about 0.1° C. to about 0.5° C./minute, about 0.5° C. to about 1.0° C./minute, about 1.0° C. to about 1.5° C./minute, about 1.5° C. to about 2.0° C./minute, about 0.5° C. to about 1.5° C./minute, or about 1.0° C. to about 2.0° C./minute.

A formulation disclosed herein result in the formation of a solid solution of the lipids and therapeutic compound. Such formulations do not form liposomal emulsions and/or micellular particles and/or any other type of multi-phasic compositions. In addition, such formulations do not require a hydrophilic solvent, such as, e.g., water or a buffered solution. As such, a pharmaceutical composition disclosed herein need not be formulated with a hydrophilic solvent. In an embodiment, a pharmaceutical composition disclosed herein does not comprise a pharmaceutically-acceptable hydrophilic solvent.

The amount of a therapeutic compound, room temperature liquid lipid, room temperature solid lipid (hard fat), stabilizing agent and neutralizing agent used in the method disclosed herein may be in any amount desired. Factors used to determine the amount of each component used include, without limitation, the final amount the therapeutic compound desired in the pharmaceutical composition, the desired concentration of a therapeutic compound in the solution, the hydrophobicity of the therapeutic compound, the lipophobicity of the therapeutic compound, the final amount of a pharmaceutical composition desired, and the conditions used to produce the solid solution pharmaceutical composition.

In one embodiment, a pharmaceutical composition comprises one or more therapeutic compound, a room temperature solid lipids or hard fats, and one or more room temperature liquid lipids, but does not comprise a pharmaceutically-acceptable hydrophilic solvent.

In one embodiment, a pharmaceutical composition comprises a one or more therapeutic compounds, one or more room temperature solid lipids or hard fats, one or more room temperature liquid lipids, and one or more stabilizing agents, but does not comprise a pharmaceutically-acceptable hydrophilic solvent. In aspects of this embodiment, a solid solution pharmaceutical composition comprises a therapeutic compound, a room temperature solid lipid or hard fat, a room temperature liquid lipid, and a liquid glycol polymer and/or a monohydric alcohol, and/or isosorbide dimethyl ether, and/or diethylene glycol monoethyl ether (2-(2-ethoxyethoxy)ethanol), but does not comprise a pharmaceutically-acceptable hydrophilic solvent. In other aspects of this embodiment, a solid solution pharmaceutical composition comprises a therapeutic compound, a triglyceride mixture, a monoglyceride mixture, and a liquid PEG polymer and/or a $C_1$-$C_5$ monohydric alcohol, and/or isosorbide dimethyl ether, and/or diethylene glycol monoethyl ether (2-(2-ethoxyethoxy)ethanol), but does not comprise a pharmaceutically-acceptable hydrophilic solvent. In yet other aspects of this embodiment, a pharmaceutical composition comprises a therapeutic compound, GELUCIRE® 43/01 (Gattefosse), a waxy solid (as room temperature solid lipid) having a melting point of between 41° C. to 45° C. and comprising a mixture of saturated $C_{10}$-$C_{18}$ triglycerides, MAISINE® 35-1 (Gattefosse), a glyceryl monolinoleate, and a liquid PEG polymer and/or a $C_1$-$C_5$ monohydric alcohol, and/or isosorbide dimethyl ether, and/or diethylene glycol monoethyl ether (2-(2-ethoxyethoxy)ethanol), but does not comprise a pharmaceutically-acceptable hydrophilic solvent.

In aspects of this embodiment, a solid solution composition comprises about 1% to about 55% by weight of therapeutic compound, about 40% to about 90% by weight of room temperature solid lipid or hard fat, about 1% to about 10% by weight of room temperature liquid lipid, and about 1% to about 5% of a stabilizing agent. In aspects of this embodiment, a solid solution composition comprises about 1% to about 55% by weight of therapeutic compound, about 40% to about 90% by weight of room temperature solid lipid or hard fat, about 1% to about 10% by weight of room temperature liquid lipid, and about 1% to about 5% of a liquid glycol polymer and/or a monohydric alcohol, and/or isosorbide dimethyl ether, and/or diethylene glycol monoethyl ether (2-(2-ethoxyethoxy)ethanol). In other aspects of this embodiment, a solid solution composition comprises about 5% to about 50% by weight of therapeutic compound, about 40% to about 70% by weight of room temperature solid lipid or hard fat, about 1% to about 7% by weight of room temperature liquid lipid, and about 1% to about 3% of a liquid glycol polymer and/or a monohydric alcohol, and/or isosorbide dimethyl ether, and/or diethylene glycol monoethyl ether (2-(2-ethoxyethoxy)ethanol).

In one embodiment, a pharmaceutical composition comprises one or more therapeutic compounds, one or more room temperature solid lipids or hard fats, one or more room temperature liquid lipids, and one or more neutralizing agents, but does not comprise a pharmaceutically-acceptable hydrophilic solvent. In other aspects of this embodiment, a solid solution pharmaceutical composition comprises a therapeutic compound, a room temperature solid lipid or hard fat, a room temperature liquid lipid, and a fatty acid, but does not comprise a pharmaceutically-acceptable hydrophilic solvent. In yet other aspects of this embodiment, a solid solution pharmaceutical composition comprises a therapeutic compound, a triglyceride mixture, a monoglyceride mixture, and a $C_{16}$-$C_{18}$ fatty acid, but does not comprise a pharmaceutically-acceptable hydrophilic solvent. In still other aspects of this embodiment, a pharmaceutical composition comprises a therapeutic compound, GELUCIRE® 43/01 (Gattefosse), a waxy solid (as room temperature solid lipid) having a melting point of between 41° C. to 45° C. and comprising a mixture of saturated $C_{10}$-$C_{18}$ triglycerides, MAISINE® 35-1 (Gattefosse), a glyceryl monolinoleate, and stearic acid, but does not comprise a pharmaceutically-acceptable hydrophilic solvent.

In aspects of this embodiment, a solid solution composition comprises about 1% to about 55% by weight of therapeutic compound, about 30% to about 70% by weight of room temperature solid lipid or hard fat, about 1% to about 10% by weight of room temperature liquid lipid, and about 1% to about 55% of neutralizing agent. In other aspects of this embodiment, a solid solution composition comprises about 1% to about 55% by weight of therapeutic compound, about 30% to about 70% by weight of room temperature solid lipid or hard fat, about 1% to about 10% by weight of room temperature liquid lipid, and about 1% to about 55% of fatty acid. In yet other aspects of this embodiment, a solid solution composition comprises about 5% to about 50% by weight of therapeutic compound, about 30% to about 60% by weight of room temperature solid lipid or hard fat, about 1% to about 7% by weight of room temperature liquid lipid, and about 5% to about 50% of a fatty acid.

In other aspects of this embodiment, a solid solution pharmaceutical composition comprises one or more therapeutic compounds, one or more room temperature solid lipids or hard fats, one or more room temperature liquid lipids, and triethanolamine, but does not comprise a pharmaceutically-acceptable hydrophilic solvent. In yet other aspects of this embodiment, a solid solution pharmaceutical composition comprises a therapeutic compound, a triglyceride mixture, a monoglyceride mixture, and triethanolamine, but does not comprise a pharmaceutically-acceptable hydrophilic solvent. In still other aspects of this embodiment, a pharmaceutical composition comprises a therapeutic compound, GELUCIRE®43/01 (Gattefosse), a waxy solid (as room temperature solid lipid) having a melting point of between 41° C. to 45° C. and comprising a mixture of saturated $C_{10}$-$C_{18}$ triglycerides, MAISINE® 35-1 (Gattefosse), a glyceryl monolinoleate, and triethanolamine, but does not comprise a pharmaceutically-acceptable hydrophilic solvent.

In aspects of this embodiment, a solid solution composition comprises about 1% to about 55% by weight of therapeutic compound, about 30% to about 70% by weight of room temperature solid lipid or hard fat, about 1% to about 10% by weight of room temperature liquid lipid, and about 1% to about 55% of triethanolamine. In other aspects of this embodiment, a solid solution composition comprises about 5% to about 50% by weight of therapeutic compound, about 30% to about 60% by weight of room temperature solid lipid or hard fat, about 1% to about 7% by weight of room temperature liquid lipid, and about 5% to about 50% of a triethanolamine.

In one embodiment, a pharmaceutical composition comprises one or more therapeutic compound, a room temperature solid lipids or hard fats, one or more room temperature liquid lipids, one or more stabilizing agents, and one or more neutralizing agents, but does not comprise a pharmaceutically-acceptable hydrophilic solvent.

Aspects of the present specification disclose, in part, a method of treating an individual with a chronic inflammation. In one embodiment, the method comprises the step of administering to an individual in need thereof a pharmaceutical composition disclosed herein, wherein administration reduces a symptom associated with the chronic inflammation, thereby treating the individual.

Aspects of the present specification disclose, in part, a solid solution composition disclosed herein for use in the treatment of chronic inflammation.

Aspects of the present specification disclose, in part, use of a solid solution composition disclosed herein for the treatment of chronic inflammation.

Aspects of the present specification disclose, in part, treating an individual suffering from a chronic inflammation. As used herein, the term "treating," refers to reducing or eliminating in an individual a clinical symptom of a chronic inflammation; or delaying or preventing in an individual the onset of a clinical symptom of a chronic inflammation. For example, the term "treating" can mean reducing a symptom of a condition characterized by a chronic inflammation by, e.g., at least 20%, at least 25%, at least 30%, at least 35%, at least 40%, at least 45%, at least 50%, at least 55%, at least 60%, at least 65%, at least 70%, at least 75%, at least 80%, at least 85%, at least 90% at least 95%, or at least 100%. The actual symptoms associated with chronic inflammation are well known and can be determined by a person of ordinary skill in the art by taking into account factors, including, without limitation, the location of the chronic inflammation, the cause of the chronic inflammation, the severity of the chronic inflammation, and/or the tissue or organ affected by the chronic inflammation. Those of skill in the art will know the appropriate symptoms or indicators associated with a specific type of chronic inflammation and will know how to determine if an individual is a candidate for treatment as disclosed herein.

Chronic inflammation symptoms include, without limitation, edema, hyperemia, erythema, bruising, tenderness, stiffness, swollenness, fever, chills, stuffy nose, stuffy head, breathing problems, fluid retention, blood clots, loss of appetite, increased heart rate, formation of granulomas, fibrinous, pus, non-viscous serous fluid, or ulcer and pain. The actual symptoms associated with a chronic inflammation are well known and can be determined by a person of ordinary skill in the art by taking into account factors, including, without limitation, the location of the inflammation, the cause of the inflammation, the severity of the inflammation, the tissue or organ affected, and the associated disorder.

Specific patterns of chronic inflammation are seen during particular situations that arise in the body, such as when inflammation occurs on an epithelial surface, or pyogenic bacteria are involved. For example, granulomatous inflammation is an inflammation resulting from the formation of granulomas arising from a limited but diverse number of diseases, include, without limitation, tuberculosis, leprosy, sarcoidosis, and syphilis. Purulent inflammation is an inflammation resulting in large amount of pus, which consists of neutrophils, dead cells, and fluid. Infection by pyogenic bacteria such as staphylococci is characteristic of this kind of inflammation. Serous inflammation is an inflammation resulting from copious effusion of non-viscous serous fluid, commonly produced by mesothelial cells of serous membranes, but may be derived from blood plasma. Skin blisters exemplify this pattern of inflammation. Ulcerative inflammation is an inflammation resulting from the necrotic loss of tissue from the epithelial surface, exposing lower layers and forming an ulcer.

A chronic inflammation symptom can be associated with a large, unrelated group of disorders which underlay a variety of diseases and disorders. The immune system is often involved with chronic inflammatory disorders, demonstrated in both allergic reactions and some myopathies, with many immune system disorders resulting in abnormal inflammation. Non-immune diseases with etiological origins in chronic inflammatory processes include cancer, atherosclerosis, and ischaemic heart disease. Non-limiting examples of disorders exhibiting chronic inflammation as a symptom include, without limitation, acne, acid reflux/heartburn, age related macular degeneration (AMD), allergy, allergic rhinitis, Alzheimer's disease, amyotrophic lateral sclerosis, anemia, appendicitis, arteritis, arthritis, asthma. atherosclerosis, autoimmune disorders, balanitis, blepharitis, bronchiolitis, bronchitis, a bullous pemphigoid, burn, bursitis, cancer, cardiac arrest, carditis, celiac disease, cellulitis, cervicitis, cholangitis, cholecystitis, chorioamnionitis, chronic obstructive pulmonary disease (COPD), cirrhosis, colitis, congestive heart failure, conjunctivitis, cyclophosphamide-induced cystitis, cystic fibrosis, cystitis, common cold, dacryoadenitis, dementia, dermatitis, dermatomyositis, diabetes, diabetic neuropathy, diabetic retinopathy, diabetic nephropathy, diabetic ulcer, digestive system disease, eczema, emphysema, encephalitis, endocarditis, endometritis, enteritis, enterocolitis, epicondylitis, epididymitis, fasciitis, fibromyalgia, fibrosis, fibrositis, gastritis, gastroenteritis, gingivitis, glomerulonephritis, glossitis, heart disease, heart valve dysfunction, hepatitis, hidradenitis suppurativa, Huntington's disease, hyperlipidemic pancreatitis, hypertension, ileitis, infection, inflammatory bowel disease, inflammatory cardiomegaly, inflammatory neuropathy, insulin resistance, interstitial cystitis, interstitial nephritis, iritis, ischemia, ischemic heart disease, keratitis, keratoconjunctivitis, laryngitis, lupus nephritis, mastitis, mastoiditis, meningitis, metabolic syndrome (syndrome X), a migraine, multiple sclerosis, myelitis, myocarditis, myositis, nephritis, non-alcoholic steatohepatitis, obesity, omphalitis, oophoritis, orchitis, osteochondritis, osteopenia, osteomyelitis, osteoporosis, osteitis, otitis, pancreatitis, Parkinson's disease, parotitis, pelvic inflammatory disease, pemphigus vularis, pericarditis, peritonitis, pharyngitis, phlebitis, pleuritis, pneumonitis, polycystic nephritis, proctitis, prostatitis, psoriasis, pulpitis, pyelonephritis, pylephlebitis, renal failure, reperfusion injury, retinitis, rheumatic fever, rhinitis, salpingitis, sarcoidosis, sialadenitis, sinusitis, spastic colon, stenosis, stomatitis, stroke, surgical complication, synovitis, tendonitis, tendinosis, tenosynovitis, thrombophlebitis, tonsillitis, trauma, traumatic brain injury, transplant rejection, trigonitis, tuberculosis, tumor, urethritis, ursitis, uveitis, vaginitis, vasculitis, and vulvitis. See also, Eric R. First, Application of Botulinum Toxin to the Management of Neurogenic Inflammatory Disorders, U.S. Pat. No. 6,063,768, which is hereby incorporated by reference in its entirety.

In one embodiment, a chronic inflammation comprises a tissue inflammation. Tissue inflammation is a chronic inflammation that is confined to a particular tissue or organ. In aspect of this embodiment, a tissue inflammation comprises, e.g., a skin inflammation, a muscle inflammation, a tendon inflammation, a ligament inflammation, a bone inflammation, a cartilage inflammation, a lung inflammation, a heart inflammation, a liver inflammation, a pancreatic inflammation, a kidney inflammation, a bladder inflammation, a stomach inflammation, an intestinal inflammation, a neuron inflammation, and a brain inflammation.

In another embodiment, a chronic inflammation comprises a systemic inflammation. Although the processes involved are identical to tissue inflammation, systemic inflammation is not confined to a particular tissue but in fact overwhelms the body, involving the endothelium and other organ systems. When it is due to infection, the term sepsis is applied, with the terms bacteremia being applied specifically for bacterial sepsis and viremia specifically to viral sepsis. Vasodilation and organ dysfunction are serious problems associated with widespread infection that may lead to septic shock and death.

In another embodiment, a chronic inflammation comprises an arthritis. Arthritis includes a group of conditions involving damage to the joints of the body due to the inflammation of the synovium including, without limitation osteoarthritis, rheumatoid arthritis, juvenile idiopathic arthritis, spondyloarthropathies like ankylosing spondylitis, reactive arthritis (Reiter's syndrome), psoriatic arthritis, enteropathic arthritis associated with inflammatory bowel disease, Whipple disease and Behcet disease, septic arthritis, gout (also known as gouty arthritis, crystal synovitis, metabolic arthritis), pseudogout (calcium pyrophosphate deposition disease), and Still's disease. Arthritis can affect a single joint (monoarthritis), two to four joints (oligoarthritis) or five or more joints (polyarthritis) and can be either an auto-immune disease or a non-autoimmune disease.

In another embodiment, a chronic inflammation comprises an autoimmune disorder. Autoimmune diseases can be broadly divided into systemic and organ-specific autoimmune disorders, depending on the principal clinico-pathologic features of each disease. Systemic autoimmune diseases include, without limitation, systemic lupus erythematosus (SLE), Sjögren's syndrome, Scleroderma, rheumatoid arthritis and polymyositis. Local autoimmune diseases may be endocrinologic (Diabetes Mellitus Type 1, Hashimoto's thyroiditis, Addison's disease etc.), dermatologic (pemphigus vulgaris), hematologic (autoimmune haemolytic anemia), neural (multiple sclerosis) or can involve virtually any circumscribed mass of body tissue. Types of autoimmune disorders include, without limitation, acute disseminated encephalomyelitis (ADEM), Addison's disease, an allergy or sensitivity, amyotrophic lateral sclerosis, anti-phospholipid antibody syndrome (APS), arthritis, autoimmune hemolytic anemia, autoimmune hepatitis, autoimmune inner ear disease, autoimmune pancreatitis, bullous pemphigoid, celiac disease, Chagas disease, chronic obstructive pulmonary disease (COPD), diabetes mellitus type 1 (IDDM), endometriosis, fibromyalgia, Goodpasture's syndrome, Graves' disease, Guillain-Barré syndrome (GBS), Hashimoto's thyroiditis, hidradenitis suppurativa, idiopathic thrombocytopenic purpura, inflammatory bowel disease, interstitial cystitis, lupus (including discoid lupus erythematosus, drug-induced lupus erythematosus. lupus nephritis, neonatal lupus, subacute cutaneous lupus erythematosus and systemic lupus erythematosus), morphea, multiple sclerosis (MS), myasthenia gravis, myopathies, narcolepsy, neuromyotonia, pemphigus vulgaris, pernicious anaemia, primary biliary cirrhosis, recurrent disseminated encephalomyelitis (multiphasic disseminated encephalomyelitis), rheumatic fever, schizophrenia, scleroderma, Sjögren's syndrome, tenosynovitis, vasculitis, and vitiligo. See Pamela D. Van Schaack & Kenneth L. Tong, Treatment of Autoimmune Disorder with a Neurotoxin, U.S. Patent Publication 2006/138059, which is hereby incorporated by reference in its entirety.

In another embodiment, a chronic inflammation comprises a myopathy. Myopathies are caused when the immune system inappropriately attacks components of the muscle, leading to inflammation in the muscle. A myopathy includes an inflammatory myopathy and an auto-immune myopathy. Myopathies include, without limitation, dermatomyositis, inclusion body myositis, and polymyositis.

In another embodiment, a chronic inflammation comprises a vasculitis. Vasculitis is a varied group of disorders featuring inflammation of a vessel wall including lymphatic vessels and blood vessels like veins (phlebitis), arteries (arteritis) and capillaries due to leukocyte migration and resultant damage. The inflammation may affect any size blood vessel, anywhere in the body. It may affect either arteries and/or veins. The inflammation may be focal, meaning that it affects a single location within a vessel; or it may be widespread, with areas of inflammation scattered throughout a particular organ or tissue, or even affecting more than one organ system in the body. Vasculitis include, without limitation, Buerger's disease (thromboangiitis obliterans), cerebral vasculitis (central nervous system vasculitis), Churg-Strauss arteritis, cryoglobulinemia, essential cryoglobulinemic vasculitis, giant cell (temporal) arteritis, Golfer's vasculitis, Henoch-Schonlein purpura, hypersensitivity vasculitis (allergic vasculitis), Kawasaki disease, microscopic polyarteritis/polyangiitis, polyarteritis *nodosa*, polymyalgia rheumatica (PMR), rheumatoid vasculitis, Takayasu arteritis, Wegener's granulomatosis, and vasculitis secondary to connective tissue disorders like systemic lupus erythematosus (SLE), rheumatoid arthritis (RA), relapsing polychondritis, Behçet's disease, or other connective tissue disorders, vasculitis secondary to viral infection.

In another embodiment, a chronic inflammation comprises a skin disorder. Skin disorders include, without limitation, an acne, including acne vulgaris, a bullous phemigoid, a dermatitis, including atopic dermatitis and chronic actinic dermatitis, an eczema like atopic eczema, contact eczema, xerotic eczema, seborrhoeic dermatitis, dyshidrosis, discoid eczema, venous eczema, dermatitis herpetiformis, neurodermatitis, and autoeczematization, and statis dermatitis, hidradenitis suppurativa, lichen planus, psoriasis including plaqure psoriasis, nail psoriasis, guttate psoriasis, scalp psoriasis, inverse psoriasis, pustular psoriasis, erythrodermis psoriasis, and psoriatic arthritis, rosacea and scleroderma including morphea.

In another embodiment, a chronic inflammation comprises a gastrointestinal disorder. A gastrointestinal disorder includes, without limitation, irritable bowel disease, an inflammatory bowel disease including Crohn's disease and an ulcerative colitis like ulcerative proctitis, left-sided colitis, pancolitis and fulminant colitis.

In another embodiment, a chronic inflammation comprises a cardiovascular disease. When LDL cholesterol becomes embedded in arterial walls, it can invoke an immune response. Chronic inflammation eventually can damage the arteries, which can cause them to burst. Cardiovascular disease is any of a number of specific diseases that affect the heart itself and/or the blood vessel system, especially the veins and arteries leading to and from the heart. There are more than 60 types of cardiovascular disorders including, without limitation, a hypertension, endocarditis, myocarditis, heart valve dysfunction, congestive heart failure, myocardial infarction, a diabetic cardiac conditions, blood vessel inflammation like arteritis, phlebitis, vasculitis; arterial occlusive disease like arteriosclerosis and stenosis, inflammatory cardiomegaly, a peripheral arterial disease; an aneurysm; an embolism; a dissection; a pseudoaneurysm; a vascular malformation; a vascular nevus; a thrombosis; a thrombphlebitis; a varicose veins; a stroke. Symptoms of a cardiovascular disorder affecting the heart include, without limitation, chest pain or chest discomfort (angina), pain in one or both arms, the left shoulder, neck, jaw, or back, shortness of breath, dizziness, faster heartbeats, nausea, abnormal heartbeats, feeling fatigued. Symptoms of a cardiovascular disorder affecting the brain include, without limitation, sudden numbness or weakness of the face, arm, or leg, especially on one side of the body, sudden confusion or trouble speaking or understanding speech, sudden trouble seeing in one or both eyes, sudden dizziness, difficulty walking, or loss of balance or coordination, sudden severe headache with no known cause. Symptoms of a cardiovascular disorder affecting the legs, pelvis and/or arm include, without limitation, claudication, which is a pain, ache, or cramp in the muscles, and cold or numb feeling in the feet or toes, especially at night.

In another embodiment, a chronic inflammation comprises a cancer. Inflammation orchestrates the microenvironment around tumors, contributing to proliferation, survival and migration. For example, fibrinous inflammation results from a large increase in vascular permeability which allows fibrin to pass through the blood vessels. If an appropriate procoagulative stimulus is present, such as cancer cells, a fibrinous exudate is deposited. This is commonly seen in serous cavities, where the conversion of fibrinous exudate into a scar can occur between serous membranes, limiting their function. In another example, a cancer is an inflammatory cancer like a NF-κB-driven inflammatory cancer.

In another embodiment, a chronic inflammation comprises a pharmacologically-induced inflammation. Certain drugs or exogenic chemical compounds are known to affect inflammation. For example, Vitamin A deficiency causes an increase in an inflammatory response. Certain illicit drugs such as cocaine and ecstasy may exert some of their detrimental effects by activating transcription factors intimately involved with inflammation (e.g. NF-κB).

In another embodiment, a chronic inflammation comprises an infection. An infectious organism can escape the confines of the immediate tissue via the circulatory system or lymphatic system, where it may spread to other parts of the body. If an organism is not contained by the actions of acute inflammation it may gain access to the lymphatic system via nearby lymph vessels. An infection of the lymph vessels is known as lymphangitis, and infection of a lymph node is known as lymphadenitis. A pathogen can gain access to the bloodstream through lymphatic drainage into the circulatory system. Infections include, without limitation, bacterial cystitis, bacterial encephalitis, pandemic influenza, viral encephalitis, and viral hepatitis (A, B and C).

In another embodiment, a chronic inflammation comprises a tissue or organ injury. Tissue or organ injuries include, without limitation, a burn, a laceration, a wound, a puncture, or a trauma.

In another embodiment, a chronic inflammation comprises a transplant rejection. Transplant rejection occurs when a transplanted organ or tissue is not accepted by the body of the transplant recipient because the immune system of the recipient attacks the transplanted organ or tissue. An adaptive immune response, transplant rejection is mediated through both T cell mediated and humoral immune (antibodies) mechanisms. A transplant rejection can be classified as a hyperacute rejection, an acute rejection, or a chronic rejection. Chronic rejection of a transplanted organ or tissue is where the rejection is due to a poorly understood chronic inflammatory and immune response against the transplanted tissue. Also included in the term "transplant rejection" is a graft-versus-host disease (GVHD). GVHD is a common complication of allogeneic bone marrow transplantation in which functional immune cells in the transplanted marrow recognize the recipient as "foreign" and mount an immunologic attack. It can also take place in a blood transfusion under certain circumstances. GVHD is divided into acute and chronic forms. Acute and chronic GVHD appear to involve different immune cell subsets, different cytokine profiles, somewhat different host targets, and respond differently to treatment.

In another embodiment, a chronic inflammation comprises a Th1-mediated inflammatory disease. In a well-functioning immune system, an immune response should result in a well balanced pro-inflammatory Th1 response and anti-inflammatory Th2 response that is suited to address the immune challenge. Generally speaking, once a pro-inflammatory Th1 response is initiated, the body relies on the anti-inflammatory response invoked by a Th2 response to counteract this Th1 response. This counteractive response includes the release of Th2 type cytokines such as, e.g., IL-4, IL-5, and IL-13 which are associated with the promotion of IgE and eosinophilic responses in atopy, and also IL-10, which has an anti-inflammatory response. A Th1-mediated inflammatory disease involves an excessive pro-inflammatory response produced by Th1 cells that leads to chronic inflammation. The Th1-mediated disease may be virally, bacterially or chemically (e.g. environmentally) induced. For example, a virus causing the Th1-mediated disease may cause a chronic or acute infection, which may cause a respiratory disorder or influenza.

In another embodiment, a chronic inflammation comprises a chronic neurogenic inflammation. Chronic neurogenic Inflammation refers to an inflammatory response initiated and/or maintained through the release of inflammatory molecules like SP or CGRP which released from peripheral sensory nerve terminals (i.e., an efferent function, in contrast to the normal afferent signaling to the spinal cord in these nerves). Chronic neurogenic inflammation includes both primary inflammation and secondary neurogenic inflammation. As used herein, the term "primary" neurogenic inflammation refers to tissue inflammation (inflammatory symptoms) that is initiated by, or results from, the release of substances from primary sensory nerve terminals (such as C and A-delta fibers). As used herein, the term "secondary" neurogenic inflammation" refers to tissue inflammation initiated by non-neuronal sources (e.g., extravasation from vascular bed or tissue interstitium-derived, such as from mast cells or immune cells) of inflammatory mediators, such as peptides or cytokines, stimulating sensory nerve terminals and causing a release of inflammatory mediators from the nerves. The net effect of both forms (primary and secondary) of chronic neurogenic inflammation is to have an inflammatory state that is maintained by the sensitization of the peripheral sensory nerve fibers. The physiological consequence of the resulting chronic neurogenic inflammation depends on the tissue in question, producing, such as, e.g., cutaneous pain (allodynia, hyperalgesia), joint pain and/or arthritis, visceral pain and dysfunction, pulmonary dysfunction (asthma, COPD), and bladder dysfunction (pain, overactive bladder).

A composition or compound is administered to an individual. An individual is typically a human being. Typically, any individual who is a candidate for a conventional chronic inflammation treatment is a candidate for a chronic inflammation treatment disclosed herein. Pre-operative evaluation typically includes routine history and physical examination in addition to thorough informed consent disclosing all relevant risks and benefits of the procedure.

A pharmaceutical composition disclosed herein may comprise a therapeutic compound in a therapeutically effective amount. As used herein, the term "effective amount" is synonymous with "therapeutically effective amount", "effective dose", or "therapeutically effective dose" and when used in reference to treating a chronic inflammation refers to the minimum dose of a therapeutic compound disclosed herein necessary to achieve the desired therapeutic effect and includes a dose sufficient to reduce a symptom associated with a chronic inflammation. The effectiveness of a therapeutic compound disclosed herein in treating a chronic inflammation can be determined by observing an improvement in an individual based upon one or more clinical symptoms, and/or physiological indicators associated with the condition. An improvement in a chronic inflammation also can be indicated by a reduced need for a concurrent therapy.

The appropriate effective amount of a therapeutic compound disclosed herein to be administered to an individual for a particular chronic inflammation can be determined by a person of ordinary skill in the art by taking into account factors, including, without limitation, the type of chronic inflammation, the location of the chronic inflammation, the cause of the chronic inflammation, the severity of the chronic inflammation, the degree of relief desired, the duration of relief desired, the particular therapeutic compound used, the rate of excretion of the therapeutic compound used, the pharmacodynamics of the therapeutic compound used, the nature of the other compounds to be included in the composition, the particular formulation, the particular route of administration, the particular characteristics, history and risk factors of the patient, such as, e.g., age, weight, general health and the like, or any combination thereof. Additionally, where repeated administration of a therapeutic compound is used, an effective amount of a therapeutic compound will further depend upon factors, including, without limitation, the frequency of administration, the half-life of the therapeutic compound, or any combination thereof. In is known by a person of ordinary skill in the art that an effective amount of a therapeutic compound disclosed herein can be extrapolated from in vitro assays and in vivo administration studies using animal models prior to administration to humans.

In aspects of this embodiment, a therapeutically effective amount of a therapeutic compound disclosed herein reduces a symptom associated with a chronic inflammation by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of a therapeutic compound disclosed herein reduces a symptom associated with a chronic inflammation by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of a therapeutic compound disclosed herein reduces a symptom associated with a chronic inflammation by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

In yet other aspects of this embodiment, a therapeutically effective amount of a therapeutic compound disclosed herein generally is in the range of about 0.001 mg/kg/day to about 100 mg/kg/day. In aspects of this embodiment, an effective amount of a therapeutic compound disclosed herein may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In other aspects of this embodiment, an effective amount of a therapeutic compound disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In yet other aspects of this embodiment, an effective amount of a therapeutic compound disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day. In still other aspects of this embodiment, an effective amount of a therapeutic compound disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

In other aspects of this embodiment, an effective amount of a therapeutic compound disclosed herein may be in the range of, e.g., about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In yet other aspects of this embodiment, an effective amount of a therapeutic compound disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

Dosing can be single dosage or cumulative (serial dosing), and can be readily determined by one skilled in the art. For instance, treatment of a chronic inflammation may comprise a one-time administration of an effective dose of a pharmaceutical composition disclosed herein. Alternatively, treatment of a chronic inflammation may comprise multiple administrations of an effective dose of a pharmaceutical composition carried out over a range of time periods, such as, e.g., once daily, twice daily, trice daily, once every few days, or once weekly. The timing of administration can vary from individual to individual, depending upon such factors as the severity of an individual's symptoms. For example, an effective dose of a pharmaceutical composition disclosed herein can be administered to an individual once daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly.

Various routes of administration can be useful for administering a therapeutic compound disclosed herein, according to a method of treating a chronic inflammation disclosed herein. A pharmaceutical composition may be administered to an individual by any of a variety of means depending, e.g., on the type of the chronic inflammation to be treated, the location of the chronic inflammation to be treated, the specific therapeutic compound or composition used, or other compound to be included in the composition, and the history, risk factors and symptoms of the individual. As such, topical, enteral or parenteral routes of administration may be suitable for of treating a chronic inflammation disclosed herein and such routes include both local and systemic delivery of a therapeutic compound or composition disclosed herein. Compositions comprising either a single therapeutic compound disclosed herein, or two or more therapeutic compounds disclosed herein are intended for inhaled, topical, intranasal, sublingual, injection, infusion, instillation, rectal and/or vaginal use may be prepared according to any method known to the art for the manufacture of pharmaceutical compositions.

In one embodiment, upon administration to an individual, a pharmaceutical composition comprising a therapeutic compound disclosed herein results in a bio-distribution of the therapeutic compound different than a bio-distribution of the therapeutic compound included in the same pharmaceutical composition, except without an adjuvant disclosed herein.

In another embodiment, upon administration to an individual, a therapeutic compound of the pharmaceutical composition disclosed herein is delivered to a macrophage. Macrophages are one of the key cell types believed to be involved in the control of the inflammation response. The resultant high level of a therapeutic compound having anti-inflammatory activity present in the macrophages results in a clinically effective treatment of chronic inflammation. In an aspect of this embodiment, upon administration to an individual, a therapeutically effective amount of a therapeutic compound of the pharmaceutical composition disclosed herein is preferentially delivered to a macrophage. In other aspect of this embodiment, upon administration to an individual, a therapeutic compound of the pharmaceutical composition disclosed herein is substantially delivered to a macrophage. In yet other aspect of this embodiment, upon administration to an individual, the amount of a therapeutic compound of the pharmaceutical composition disclosed herein delivered to a macrophage is, e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the total amount of the therapeutic compound contained in the administered pharmaceutical composition. In still other aspects of this embodiment, upon administration to an individual, the amount of a therapeutic compound of the pharmaceutical composition disclosed herein delivered to a macrophage is in a range of, e.g., about 5% to about 100%, about 10% to about 100%, about 15% to about 100%, about 20% to about 100%, about 25% to about 100%, about 30% to about 100%, about 35% to about 100%, about 40% to about 100%, about 45% to about 100%, about 50% to about 100%, about 5% to about 90%, about 10% to about 90%, about 15% to about 90%, about 20% to about 90%, about 25% to about 90%, about 30% to about 90%, about 35% to about 90%, about 40% to about 90%, about 45% to about 90%, about 50% to about 90%, about 5% to about 80%, about 10% to about 80%, about 15% to about 80%, about 20% to about 80%, about 25% to about 80%, about 30% to about 80%, about 35% to about 80%, about 40% to about 80%, about 45% to about 80%, about 50% to about 80%, about 5% to about 70%, about 10% to about 70%, about 15% to about 70%, about 20% to about 70%, about 25% to about 70%, about 30% to about 70%, about 35% to about 70%, about 40% to about 70%, about 45% to about 70%, or about 50% to about 70% of the total amount of the therapeutic compound contained in the administered pharmaceutical composition.

In another embodiment, upon administration to an individual, a therapeutic compound of the pharmaceutical composition disclosed herein is delivered to a dentritic cell. Dendritic cells are one of the key cell types believed to coordinate the interplay between innate and adaptive immunity. The resultant high level of a therapeutic compound having anti-pain activity present in the dentritic cells results in a clinically effective treatment of chronic inflammation. In an aspect of this embodiment, upon administration to an individual, a therapeutically effective amount of a therapeutic compound of the pharmaceutical composition disclosed herein is preferentially delivered to a dentritic cell. In other aspect of this embodiment, upon administration to an individual, a therapeutic compound of the pharmaceutical composition disclosed herein is substantially delivered to a dentritic cell. In yet other aspect of this embodiment, upon administration to an individual, the amount of a therapeutic compound of the pharmaceutical composition disclosed herein delivered to a dentritic cell is, e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the total amount of the therapeutic compound contained in the administered pharmaceutical composition. In still other aspects of this embodiment, upon administration to an individual, the amount of a therapeutic compound of the pharmaceutical composition disclosed herein delivered to a dentritic cell is in a range of, e.g., about 5% to about 100%, about 10% to about 100%, about 15% to about 100%, about 20% to about 100%, about 25% to about 100%, about 30% to about 100%, about 35% to about 100%, about 40% to about 100%, about 45% to about 100%, about 50% to about 100%, about 5% to about 90%, about 10% to about 90%, about 15% to about 90%, about 20% to about 90%, about 25% to about 90%, about 30% to about 90%, about 35% to about 90%, about 40% to about 90%, about 45% to about 90%, about 50% to about 90%, about 5% to about 80%, about 10% to about 80%, about 15% to about 80%, about 20% to about 80%, about 25% to about 80%, about 30% to about 80%, about 35% to about 80%, about 40% to about 80%, about 45% to about 80%, about 50% to about 80%, about 5% to about 70%, about 10% to about 70%, about 15% to about 70%, about 20% to about 70%, about 25% to about 70%, about 30% to about 70%, about 35% to about 70%, about 40% to about 70%, about 45% to about 70%, or about 50% to about 70% of the total amount of the therapeutic compound contained in the administered pharmaceutical composition.

In another embodiment, upon administration to an individual, a pharmaceutical composition disclosed herein reduces gastric irritation. In an aspect of this embodiment, a pharmaceutical composition disclosed herein substantially reduces gastric irritation. In yet another embodiment, upon administration to an individual, a pharmaceutical composition disclosed herein reduces gastric irritation when compared to the same pharmaceutical composition disclosed herein, except without the pharmaceutically-acceptable adjuvant. In an aspect of this embodiment, a pharmaceutical composition disclosed herein substantially reduces gastric irritation when compared to the same pharmaceutical composition disclosed herein, except without the pharmaceutically-acceptable adjuvant. In other aspects of this embodiment, a pharmaceutical composition disclosed herein reduces gastric irritation by, e.g., at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In yet other aspects of this embodiment, a pharmaceutical composition disclosed herein reduces gastric irritation in a range of, e.g., about 5% to about 100%, about 10% to about 100%, about 15% to about 100%, about 20% to about 100%, about 25% to about 100%, about 30% to about 100%, about 35% to about 100%, about 40% to about 100%, about 45% to about 100%, about 50% to about 100%, about 5% to about 90%, about 10% to about 90%, about 15% to about 90%, about 20% to about 90%, about 25% to about 90%, about 30% to about 90%, about 35% to about 90%, about 40% to about 90%, about 45% to about 90%, about 50% to about 90%, about 5% to about 80%, about 10% to about 80%, about 15% to about 80%, about 20% to about 80%, about 25% to about 80%, about 30% to about 80%, about 35% to about 80%, about 40% to about 80%, about 45% to about 80%, about 50% to about 80%, about 5% to about 70%, about 10% to about 70%, about 15% to about 70%, about 20% to about 70%, about 25% to about 70%, about 30% to about 70%, about 35% to about 70%, about 40% to about 70%, about 45% to about 70%, or about 50% to about 70%.

In another embodiment, upon administration to an individual, a pharmaceutical composition disclosed herein reduces intestinal irritation. In an aspect of this embodiment, a pharmaceutical composition disclosed herein substantially reduces intestinal irritation. In yet another embodiment, upon administration to an individual, a pharmaceutical composition disclosed herein reduces intestinal irritation when compared to the same pharmaceutical composition disclosed herein, except without the pharmaceutically-acceptable adjuvant. In an aspect of this embodiment, a pharmaceutical composition disclosed herein substantially reduces intestinal irritation when compared to the same pharmaceutical composition disclosed herein, except without the pharmaceutically-acceptable adjuvant. In other aspects of this embodiment, a pharmaceutical composition disclosed herein reduces intestinal irritation by, e.g., at least 5%, at least 10%, at least 20%, at least 30%, at least 40%, at least 50%, at least 60%, at least 70%, at least 80%, at least 90%, or at least 100% when compared to the same pharmaceutical composition disclosed herein, except without the pharmaceutically-acceptable adjuvant. In yet other aspects of this embodiment, a pharmaceutical composition disclosed herein reduces intestinal irritation by, e.g., about 5% to about 100%, about 10% to about 100%, about 15% to about 100%, about 20% to about 100%, about 25% to about 100%, about 30% to about 100%, about 35% to about 100%, about 40% to about 100%, about 45% to about 100%, about 50% to about 100%, about 5% to about 90%, about 10% to about 90%, about 15% to about 90%, about 20% to about 90%, about 25% to about 90%, about 30% to about 90%, about 35% to about 90%, about 40% to about 90%, about 45% to about 90%, about 50% to about 90%, about 5% to about 80%, about 10% to about 80%, about 15% to about 80%, about 20% to about 80%, about 25% to about 80%, about 30% to about 80%, about 35% to about 80%, about 40% to about 80%, about 45% to about 80%, about 50% to about 80%, about 5% to about 70%, about 10% to about 70%, about 15% to about 70%, about 20% to about 70%, about 25% to about 70%, about 30% to about 70%, about 35% to about 70%, about 40% to about 70%, about 45% to about 70%, or about 50% to about 70% when compared to the same pharmaceutical composition disclosed herein, except without the pharmaceutically-acceptable adjuvant.

A pharmaceutical composition disclosed herein can also be administered to an individual in combination with other therapeutic compounds to increase the overall therapeutic effect of the treatment. The use of multiple compounds to treat an indication can increase the beneficial effects while reducing the presence of side effects.

Aspects of the present invention can also be described as follows:
1. A solid solution pharmaceutical composition comprising: a) a therapeutic compound, wherein the therapeutic compound has an anti-inflammatory activity; b) a room temperature solid lipid; and c) a room temperature liquid lipid.
2. The solid solution pharmaceutical composition according to embodiment 1, wherein the composition further comprises a stabilizing agent.
3. The solid solution pharmaceutical composition according to embodiment 1 or 2, wherein the composition further comprises a neutralizing agent.
4. A solid solution pharmaceutical composition according to embodiments 1-3, wherein the solid solution pharmaceutical composition does not comprise a surfactant.
5. A solid solution pharmaceutical composition according to embodiments 1-4, wherein the solid solution pharmaceutical composition does not comprise a hydrophilic solvent.
6. The solid solution pharmaceutical composition according to embodiments 1-5, wherein the anti-inflammatory activity reduces the level of an inflammation inducing molecule.
7. The solid solution pharmaceutical composition according to embodiment 6, wherein the inflammation inducing molecule comprises substance P (SP), calcitonin gene-related peptide (CGRP), glutamate, or a combination thereof.
8. The solid solution pharmaceutical composition according to embodiment 7, wherein the anti-inflammatory activity reduces the level of SP, CGRP, glutamate, or a combination thereof by at least 10%.
9. The solid solution pharmaceutical composition according to embodiments 1-8, wherein the anti-inflammatory activity reduces the level of an inflammation inducing prostaglandin.
10. The solid solution pharmaceutical composition according to embodiment 9, wherein the level of the inflammation inducing prostaglandin is reduced by at least 10%.
11. The solid solution pharmaceutical composition according to embodiments 1-10, wherein the anti-inflammatory activity stimulates a PPAR signaling pathway.
12. The solid solution pharmaceutical composition according to embodiment 11, wherein the PPAR signaling pathway is stimulated by at least 10%.
13. The solid solution pharmaceutical composition according to embodiments 1-12, wherein the anti-inflammatory activity induces apoptosis of Macrophage M1 cells, promotes differentiation of Macrophage M2 cells, or both.
14. The solid solution pharmaceutical composition according to embodiments 1-13, wherein the anti-inflammatory activity reducing the levels of Interferon-gamma (IFNγ), Tumor necrosis factor-alpha (TNF-α), Interleukin-12 (IL-12), or a combination thereof released from Th1 cells, increases the levels of IL-10 released from a Th2 cell, or both.
15. The solid solution pharmaceutical composition according to embodiment 14, wherein the levels of IFNγ, TNF-α, IL-12, or a combination thereof released from a Th1 cell are reduced by at least 10%.
16. The solid solution pharmaceutical composition according to embodiment 14, wherein the levels of IL-10 released from a Th2 cell are increased by at least 10%.
17. The solid solution pharmaceutical composition according to embodiments 1-16, wherein the therapeutic compound has a log P value of 3.0 or greater.
18. The solid solution pharmaceutical composition according to embodiments 1-16, wherein the therapeutic compound has a log P value of about 2.2 to about 3.0.
19. The solid solution pharmaceutical composition according to embodiments 1-16, wherein the therapeutic compound has a log P value of about 2.0 or less.
20. The pharmaceutical composition according to embodiments 1-19, wherein the therapeutic compound has a polar surface area that is hydrophobic.

21. The pharmaceutical composition according to embodiments 1-20, wherein the therapeutic compound has a polar surface area that is less than 8.0 nm$^2$.
22. The pharmaceutical composition according to embodiments 1-20, wherein the therapeutic compound has a polar surface area that is less than 6.0 nm$^2$.
23. The pharmaceutical composition according to embodiments 1-22, wherein the therapeutic compound comprises a non-steroidal anti-inflammatory drug (NSAID).
24. The pharmaceutical composition according to embodiment 23, wherein the NSAID comprises a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor or a combination thereof.
25. The pharmaceutical composition according to embodiments 1-24, wherein the therapeutic compound comprises a PPARα agonist, a PPARβ/δ agonist, a PPARγ agonist, or a Glitazar.
26. The pharmaceutical composition according to embodiments 1-25, wherein the therapeutic compound comprises an immunosupressive drug, an uricosuric drug, an Aglycone, or a Cannabidiol.
27. The pharmaceutical composition according to embodiments 1-26, wherein the therapeutic compound comprises a Ryanodine receptor antagonist.
28. The pharmaceutical composition according to embodiment 27, wherein the Ryanodine receptor antagonist is Azumolene or Dantrolene.
29. The pharmaceutical composition according to embodiments 1-28, wherein the therapeutic compound comprises a nuclear receptor binding agent.
30. The pharmaceutical composition according to embodiment 29, wherein the nuclear receptor binding agent comprises a Retinoic Acid Receptor (RAR) binding agent, a Retinoid X Receptor (RXR) binding agent, a Liver X Receptor (LXR) binding agent, a Vitamin D binding agent, or a combination thereof.
31. The pharmaceutical composition according to embodiments 1-30, wherein the therapeutic compound comprises an anti-hyperlipidemic agent.
32. The pharmaceutical composition according to embodiment 31, wherein the anti-hyperlipidemic agent comprises an Angiotension II receptor antagonist, a ACE inhibitor, a phosphodiesterase inhibitor, a fibrate, a statin, a tocotrienol, a niacin, a bile acid sequestrants (resin), a cholesterol absorption inhibitor, a pancreatic lipase inhibitor, a sympathomimetic amine, or a combination thereof.
33. The pharmaceutical composition according to embodiment 32, wherein the Angiotension II receptor antagonist comprises Azilsartan, Candesartan, Eprosartan, Irbesartan, Losartan, Olmesartan, Telmisartan, and Valsartan.
34. The pharmaceutical composition according to embodiment 32, wherein the ACE inhibitor comprises a Sulfhydryl-containing agent, a Dicarboxylate-containing agent, a Phosphonate-containing agent, a Casokinin, and a Lactokinin.
35. The pharmaceutical composition according to embodiment 32, wherein the phosphodiesterase inhibitor comprises a PDE 1 selective inhibitor, a PDE 2 selective inhibitor, a PDE 3 selective inhibitor, a PDE 4 selective inhibitor, a PDE 5 selective inhibitor, or a PDE 10 selective inhibitor.
36. The pharmaceutical composition according to embodiment 32, wherein the fibrate comprises Bezafibrate, Ciprofibrate, Clofibrate, Gemfibrozil, Fenofibrate, or a combination thereof.
37. The pharmaceutical composition according to embodiment 32, wherein the statin comprises Atorvastatin, Fluvastatin, Lovastatin, Pitavastatin, Pravastatin, Rosuvastatin, Simvastatin, or a combination thereof.
38. The pharmaceutical composition according to embodiment 32, wherein the niacin comprises acipimox, niacin, nicotinamide, vitamin B3, or a combination thereof.
39. The pharmaceutical composition according to embodiment 32, wherein the bile acid sequestrant comprises Cholestyramine, Colesevelam, Colestipol, or a combination thereof.
40. The pharmaceutical composition according to embodiment 32, wherein the cholesterol absorption inhibitor comprises Ezetimibe, a phytosterol, a sterol, a stanol, or a combination thereof.
41. The pharmaceutical composition according to embodiment 32, wherein the fat absorption inhibitor comprises Orlistat
42. The pharmaceutical composition according to embodiment 32, wherein the sympathomimetic amine comprises Clenbuterol, Salbutamol, ephedrine, pseudoephedrine, methamphetamine, amphetamine, phenylephrine, isoproterenol, dobutamine, methylphenidate, lisdexamfetamine, cathine, cathinone, methcathinone, cocaine, benzylpiperazine (BZP), methylenedioxypyrovalerone (MDPV), 4-methylaminorex, pemoline, phenmetrazine, propylhexedrine, or a combination thereof.
43. The pharmaceutical composition according to embodiments 1-42, wherein the therapeutic compound comprises a cancer drug.
44. The pharmaceutical composition according to embodiment 43, wherein the cancer drug comprises an alkylating agent, an anti-metabolite, a plant alkaloid and terpenoid, a topoisomerase inhibitor or a cytotoxic antibiotic.
45. The pharmaceutical composition according to embodiments 1-44, wherein the therapeutic compound comprises Metformin, Curcumin, glycyrrhetinic acid, or 6-shogaol.
46. The pharmaceutical composition according to embodiments 1-44, wherein the therapeutic compound comprises an antibiotic.
47. The pharmaceutical composition according to embodiment 46, wherein the antibiotic comprises Isoniazid, Rifampicin, Pyrazinamide, or Ethambutol.
48. The pharmaceutical composition according to embodiments 1-47, wherein the therapeutic compound comprises an anti-helmintic drug.
49. The pharmaceutical composition according to embodiment 48, wherein the anti-helmintic drug comprises Abamectin, an Aminoacetonitrile like Monepantel, a Benzimidazole, Diethylcarbamazine, Ivermectin, Levamisole, Niclosamide, an Octadepsipeptide like Emodepside, Phosphonic acid (Metrifonate), Praziquantel, a Spiroindole like Derquantel, or Suramin Pyrantel pamoate.
50. The pharmaceutical composition according to embodiments 1-49, wherein the therapeutic compound comprises an anti-malaria drug.
51. The pharmaceutical composition according to embodiment 50, wherein the anti-malaria drug comprises Amodiaquine, an Artemisinin, Atovaquone, Chloroquine, Clindamycin, Doxycycline, Halofantrine, Mefloquine, Primaquine, Proguanil, Pyrimethamine, a Quinine and related agent like Quinimax and Quinidine, Rufigallol, and a Sulfonamide like Sulfadoxine or Sulfamethoxypyridazine.

52. The pharmaceutical composition according to embodiment 51, wherein the Artemisinin comprises Arteether, Artemether, Artemisinin, Artesunate, or Dihydroartemisinin.

53. The pharmaceutical composition according to embodiments 1-52, wherein the therapeutic compound comprises an ester of a therapeutic compound.

54. The pharmaceutical composition according to embodiments 1-53, wherein the therapeutic compound comprises an ester of a therapeutic compound according to embodiments 23-53.

55. The pharmaceutical composition according to embodiments 1-54, wherein the therapeutic compound is in an amount less than about 90% by weight, less than about 80% by weight, less than about 70% by weight, less than about 65% by weight, less than about 60% by weight, less than about 55% by weight, less than about 50% by weight, less than about 45% by weight, less than about 40% by weight, less than about 35% by weight, less than about 30% by weight, less than about 25% by weight, less than about 20% by weight, less than about 15% by weight, less than about 10% by weight, less than about 5% by weight, or less than about 1% by weight or about 1% to 90% by weight, about 1% to 80% by weight, about 1% to 75% by weight, about 1% to 70% by weight, about 1% to 65% by weight, about 1% to 60% by weight, about 1% to 55% by weight, about 1% to 50% by weight, about 1% to 45% by weight, about 1% to 40% by weight, about 1% to 35% by weight, about 1% to 30% by weight, about 1% to 25% by weight, about 1% to 20% by weight, about 1% to 15% by weight, about 1% to 10% by weight, about 1% to 5% by weight, about 2% to 50% by weight, about 2% to 40% by weight, about 2% to 30% by weight, about 2% to 20% by weight, about 2% to 10% by weight, about 4% to 50% by weight, about 4% to 40% by weight, about 4% to 30% by weight, about 4% to 20% by weight, about 4% to 10% by weight, about 6% to 50% by weight, about 6% to 40% by weight, about 6% to 30% by weight, about 6% to 20% by weight, about 6% to 10% by weight, about 8% to 50% by weight, about 8% to 40% by weight, about 8% to 30% by weight, about 8% to 20% by weight, about 8% to 15% by weight, or about 8% to 12% by weight.

56. The pharmaceutical composition according to embodiments 1-55, wherein the therapeutic compound is in an amount of about 0.1% to about 45% by weight, about 0.1% to about 40% by weight, about 0.1% to about 35% by weight, about 0.1% to about 30% by weight, about 0.1% to about 25% by weight, about 0.1% to about 20% by weight, about 0.1% to about 15% by weight, about 0.1% to about 10% by weight, about 0.1% to about 5% by weight, about 1% to about 45% by weight, about 1% to about 40% by weight, about 1% to about 35% by weight, about 1% to about 30% by weight, about 1% to about 25% by weight, about 1% to about 20% by weight, about 1% to about 15% by weight, about 1% to about 10% by weight, about 1% to about 5% by weight, about 5% to about 45% by weight, about 5% to about 40% by weight, about 5% to about 35% by weight, about 5% to about 30% by weight, about 5% to about 25% by weight, about 5% to about 20% by weight, about 5% to about 15% by weight, about 5% to about 10% by weight, about 10% to about 45% by weight, about 10% to about 40% by weight, about 10% to about 35% by weight, about 10% to about 30% by weight, about 10% to about 25% by weight, about 10% to about 20% by weight, about 10% to about 15% by weight, about 15% to about 45% by weight, about 15% to about 40% by weight, about 15% to about 35% by weight, about 15% to about 30% by weight, about 15% to about 25% by weight, about 15% to about 20% by weight, about 20% to about 45% by weight, about 20% to about 40% by weight, about 20% to about 35% by weight, about 20% to about 30% by weight, about 20% to about 25% by weight, about 25% to about 45% by weight, about 25% to about 40% by weight, about 25% to about 35% by weight, or about 25% to about 30% by weight.

57. The pharmaceutical composition according to embodiments 1-56, wherein the pharmaceutically-acceptable room temperature solid lipid is a pharmaceutically-acceptable glycerolipid, a pharmaceutically-acceptable glycol fatty acid ester, a pharmaceutically-acceptable polyether fatty acid ester, a mixture of pharmaceutically-acceptable lipids, or any combination thereof.

58. The pharmaceutical composition according to embodiments 1-57, wherein the pharmaceutically-acceptable glycerolipids is Cocoa butter, mixtures of PEG-6 sterate and ethylene glycol palmitostearate and PEG-32 stearate (TEFOSE® 1500; TEFOSE® 63), mixtures of triceteareth-4 phosphate and ethylene glycol palmitostearate and diethylene glycol palmitostearate (SEDEFOS® 75), mixtures of glycerol monostearate and PEG-75 stearate (GELOT®), mixtures of cetyl alcohol and ethoxylated fatty alcohols (seteth-2-, steareth-20) (EMULCIRE®), mixtures of saturated $C_{10}$-$C_{18}$ triglycerides having a melting point around 33° C. (GELUCIRE® 33/01), mixtures of saturated $C_{10}$-$C_{18}$ triglycerides having a melting point around 39° C. (GELUCIRE® 39/01), mixtures of saturated $C_{10}$-$C_{18}$ triglycerides having a melting point around 43° C. (GELUCIRE® 43/01), mixtures of glycerol monostearate 40-55 (type I) and diglycerides (GELEOL® Mono and Diglycerides), and mixtures of medium-chain triglycerides (LABRAFAC® Lipophile WL 1349).

59. The pharmaceutical composition according to embodiments 1-58, wherein the pharmaceutically-acceptable glycol fatty acid ester is an ethylene glycol fatty acid ester, a diethylene glycol fatty acid ester, a propylene glycol fatty acid ester, and a dipropylene fatty acid ester, ethelene glycol caprylate, ethelene glycol pelargonate, ethelene glycol caprate, ethelene glycol undecylate, ethelene glycol laurate, ethelene glycol tridecylate, ethelene glycol myristate, ethelene glycol myristolate, ethelene glycol pentadecyclate, ethelene glycol palmitate, ethelene glycol palmitoleate, ethelene glycol sapienate, ethelene glycol margarate, ethelene glycol stearate, ethelene glycol palmitostearate, ethelene glycol oleate, ethelene glycol elaidate, ethelene glycol vaccinate, ethelene glycol linoleate, ethelene glycol linoelaidate, ethelene glycol α-linolenate, ethelene glycol γ-linolerate, ethelene glycol stearidonate, ethelene glycol capprylocaprate, ethelene glycol dicapprylocaprate, diethelene glycol caprylate, diethelene glycol pelargonate, diethelene glycol caprate, diethelene glycol undecylate, diethelene glycol laurate, diethelene glycol tridecylate, diethelene glycol myristale, diethelene glycol myristolate, diethelene glycol pentadecyclate, diethelene glycol palmitate, diethelene glycol palmitoleate, diethelene glycol sapienate, diethelene glycol margarate, diethelene glycol stearate, diethelene glycol palmitostearate, diethelene glycol oleate, diethelene glycol elaidate, diethelene glycol vaccinate, diethelene glycol linoleate, diethelene glycol linoelaidate, diethelene glycol α-linolenate. diethelene glycol γ-linolenate, diethelene glycol stearidonate, diethelene glycol capprylocaprate, diethelene glycol dicapprylocaprate. propylene glycol caprylate. propylene glycol pelargonate. propylene glycol caprate. propylene glycol undecylate. propylene glycol laurate. propylene glycol tridecylate. propylene glycol myristate, propylene glycol myristolate. propylene glycol pentadecyclate, propylene glycol palmlate, propylene glycol palmitoleate, propylene glycol sapienate. propylene glycol margarate. propylene glycol stearate, propylene glycol palmitostearate, propylene glycol oleate. propylene glycol elaidate. propylene glycol vaccinate, propylene glycol linoleate. propylene glycol linoelaidate. propylene glycol α-linolenate, propylene glycol γ-linolenate, propylene glycol stearidonate. propylene glycol capprylocaprate, propylene glycol dicapprylocaprate. dipropylene glycol caprylate. dipropylene glycol pelargonate. dipropylene glycol caprate. dipropylene glycol undecylate. dipropylene glycol laurate. dipropylene glycol tricecylate, dipropylene glycol myristate. dipropylene glycol myristolate. dipropylene glycol pentadecyclate. dipropylene glycol palmitate. dipropylene glycol palmitoleate, dipropylene glycol sapienate. dipropylene glycol margarate. dipropylene glycol stearate, dipropylene glycol palmitostearate, dipropylene glycol oleate. dipropylene glycol elaidate. dipropylene glycol vaccinate, dipropylene glycol linoleate, dipropylene glycol linoelaidate. dipropylene glycol α-linolenate, dipropylene glycol γ-linolenate, dipropylene glycol stearidonate. dipropylene glycol capprylocaprate, dipropylene glycol dicapprylocaprate. propylene glycol monopalmitostearate (MONOSTEOL®), propylene glycol dicaprylocaprate (LABRAFAC® PG), propylene glycol monolaurate (type I) (LAUROGLYCOL® FCC), propylene glycol monolaurate (type II) (LAUROGLYCOL® 90). propylene glycol monocaprylate (type I) (CAPRYOL® PGMC), propylene glycol monocaprylate (type II) (CAPRYOL® 90), or any combination thereof.

60. The pharmaceutical composition according to embodiments 1-59, wherein the pharmaceutically-acceptable polyether fatty acid ester is a PEG fatty acid ester, a PEG glyceryl fatty acid, a PEG fatty acid ester glyceride, a PPG fatty acid ester, a PPG glyceryl fatty acid, or a PPG fatty acid ester glyceride 61. The pharmaceutical composition according to embodiments 1-60, wherein the pharmaceutically-acceptable room temperature solid lipid is in an amount sufficient to form solid solution composition.

62. The pharmaceutical composition according to embodiments 1-61, wherein the pharmaceutically-acceptable room temperature solid lipid is in an amount of at least 10% by weight, at least 20% by weight, at least 30% by weight, at least 35% by weight, at least 40% by weight, at least 45% by weight, at least 50% by weight, at least 55% by weight, at least 60% by weight, at least 65% by weight, at least 70% by weight, at least 75% by weight, at least 80% by weight, at least 85% by weight, at least 90% by weight, at least 95% by weight, or at least 99% by weight or about 30% to about 99% by weight, about 35% to about 99% by weight, about 40% to about 99% by weight, about 45% to about 99% by weight, about 50% to about 99% by weight, about 30% to about 98% by weight, about 35% to about 98% by weight, about 40% to about 98% by weight, about 45% to about 98% by weight, about 50% to about 98% by weight, about 30% to about 95% by weight, about 35% to about 95% by weight, about 40% to about 95% by weight, about 45% to about 95% by weight, or about 50% to about 95% by weight or about 70% to about 97% by weight, about 75% to about 97% by weight, about 80% to about 97% by weight, about 85% to about 97% by weight, about 88% to about 97% by weight, about 89% to about 97% by weight, about 90% to about 97% by weight, about 75% to about 96% by weight, about 80% to about 96% by weight, about 85% to about 96% by weight, about 88% to about 96% by weight, about 89% to about 96% by weight, about 90% to about 96% by weight, about 75% to about 93% by weight, about 80% to about 93% by weight, about 85% to about 93% by weight, about 88% to about 93% by weight, about 89% to about 93% by weight, or about 90% to about 93% by weight.

63. The pharmaceutical composition according to embodiments 1-62, wherein the pharmaceutically-acceptable room temperature liquid lipid is a monoglyceride.

64. The pharmaceutical composition according to embodiment 63, wherein the monoglyceride is glycerol monomyristoleate, glycerol monopalmitoleate, glycerol monosapienate, glycerol monooleate, glycerol monoelaidate, glycerol monovaccenate, glycerol monolinoleate, glycerol monolinoelaidate, glycerol monolinolenate, glycerol monostearidonate, glycerol monoeicosenoate, glycerol monomeadate, glycerol monoarachidonate, glycerol monoeicosapentaenoate, glycerol monoerucate, glycerol monodocosahexaenoate, glycerol mononervonate, glyceryl dibehenate (COMPRITOL® 888), glycerol behenate (COMPRITOL® E ATO), glycerol dipalmitostearate (Biogapress Vegetal BM297ATO), glycerol distearate (type I) (PRECIROL® ATO 5), and glycerol monolinoleate (MAISINE™ 35-1).

65. The pharmaceutical composition according to embodiments 1-64, wherein the pharmaceutically-acceptable room temperature liquid lipid is in an amount sufficient to dissolve a therapeutic compound.

66. The pharmaceutical composition according to embodiments 1-65, wherein the pharmaceutically-acceptable room temperature liquid lipid is in an amount of less than about 90% by weight, less than about 80% by weight, less than about 70% by weight, less than about 65% by weight, less than about 60% by weight, less than about 55% by weight, less than about 50% by weight, less than about 45% by weight, less than about 40% by weight, less than about 35% by weight, less than about 30% by weight, less than about 25% by weight, less than about 20% by weight, less than about 15% by weight, less than about 10% by weight, less than about 5% by weight, or less than about 1% by weight or about 1% to 90% by weight, about 1% to 80% by weight, about 1% to 70% by weight, about 1% to 60% by weight, about 1% to 50% by weight, about 1% to 40% by weight, about 1% to 30% by weight, about 1% to 20% by weight, about 1% to 10% by weight, about 2% to 50% by weight, about 2% to 40% by weight, about 2% to 30% by weight, about 2% to 20% by weight, about 2% to 10% by weight, about 4% to 50% by weight, about 4% to 40% by weight, about 4% to 30% by weight, about 4% to 20% by weight, about 4% to 10% by weight, about 6% to 50% by weight, about 6% to 40% by weight, about 6% to 30% by weight, about 6% to 20% by weight, about 6% to 10% by weight, about 8% to 50% by weight, about 8% to 40% by weight, about 8% to 30% by weight, about 8% to 20% by weight, about 8% to 15% by weight, or about 8% to 12% by weight.

67. The pharmaceutical composition according to embodiments 1-66, wherein the stabilizing agent is a liquid glycol polymer, a monohydric alcohol, isosorbide dimethyl ether, and diethylene glycol monoethyl ether (2-(2-ethoxyethoxy)ethanol) (TRANSCUTOL®).

68. The pharmaceutical composition according to embodiment 67, wherein the liquid glycol polymer is a liquid PEG polymer and/or a liquid PPH polymer.
69. The pharmaceutical composition according to embodiment 68, wherein the monohydric alcohol is ethanol, propanol, butanol, pentanol, or 1-hexadecanol.
70. The pharmaceutical composition according to embodiments 1-69, wherein the pharmaceutically-acceptable stabilizing agent is in an amount sufficient to stabilize the free acid or base present in the therapeutic compound.
71. The pharmaceutical composition according to embodiments 1-70, wherein the pharmaceutically-acceptable stabilizing agent is in an amount of less than about 40% by weight, less than about 35% by weight, less than about 30% by weight, less than about 25% by weight, less than about 20% by weight, less than about 19% by weight, less than about 18% by weight, less than about 17% by weight, less than about 16% by weight, less than about 15% by weight, less than about 14% by weight, less than about 13% by weight, less than about 12% by weight, less than about 11% by weight, less than about 10% by weight, less than about 9% by weight, less than about 8% by weight, less than about 7% by weight, less than about 6% by weight, less than about 5% by weight, less than about 4% by weight, less than about 3% by weight, less than about 2% by weight, or less than about 1% or about 1% to about 5% by weight, about 1% to about 7% by weight, about 1% to about 10% by weight, about 1% to about 12% by weight, about 1% to about 15% by weight, about 1% to about 18% by weight, about 1% to about 20% by weight, about 2% to about 5% by weight, about 2% to about 7% by weight, about 2% to about 10% by weight, about 2% to about 12% by weight, about 2% to about 15% by weight, about 2% to about 18% by weight, about 2% to about 20% by weight, about 3% to about 5% by weight, about 3% to about 7% by weight, about 3% to about 10% by weight, about 3% to about 12% by weight, about 3% to about 15% by weight, about 3% to about 18% by weight, about 3% to about 20% by weight, about 4% to about 5% by weight, about 4% to about 7% by weight, about 4% to about 10% by weight, about 4% to about 12% by weight, about 4% to about 15% by weight, about 4% to about 18% by weight, about 4% to about 20% by weight, about 5% to about 7% by weight, about 5% to about 10% by weight, about 5% to about 12% by weight, about 5% to about 15% by weight, about 5% to about 18% by weight, about 5% to about 20% by weight, about 6% to about 7% by weight, about 6% to about 10% by weight, about 6% to about 12% by weight, about 6% to about 15% by weight, about 6% to about 18% by weight, about 6% to about 20% by weight, about 7% to about 10% by weight, about 7% to about 12% by weight, about 7% to about 15% by weight, about 7% to about 18% by weight, about 7% to about 20% by weight, about 8% to about 10% by weight, about 8% to about 12% by weight, about 8% to about 15% by weight, about 8% to about 18% by weight, about 8% to about 20% by weight, about 9% to about 10% by weight, about 9% to about 12% by weight, about 9% to about 15% by weight, about 9% to about 18% by weight, about 9% to about 20% by weight, about 10% to about 12% by weight, about 10% to about 15% by weight, about 10% to about 18% by weight, or about 10% to about 20% by weight.
72. The pharmaceutical composition according to embodiments 1-71, wherein the pharmaceutically-acceptable stabilizing agent is not used as a solvent.
73. The pharmaceutical composition according to embodiments 1-72, wherein the pharmaceutically-acceptable stabilizing agent results in no more than 85%, no more than 80%, no more than 75%, no more than 70%, no more than 65%, no more than 60%, no more than 55%, no more than 50%, no more than 45%, no more than 40%, no more than 35%, no more than 30%, no more than 25%, no more than 20%, no more than 15%, no more than 10%, or no more than 5% dissolution of the therapeutic compound.
74. The pharmaceutical composition according to embodiments 1-73, wherein the pharmaceutically-acceptable neutralizing agent is in an amount sufficient to neutralized the ionic charges produced when the therapeutic compound dissolves.
75. The pharmaceutical composition according to embodiments 1-74, wherein the pharmaceutically-acceptable neutralizing agent is in an amount of one molar equivalent relative to the therapeutic compound.
76. The pharmaceutical composition according to embodiments 1-75, wherein the pharmaceutically-acceptable neutralizing agent is in an amount of less than one molar equivalent relative to the therapeutic compound.
77. The pharmaceutical composition according to embodiments 1-76, wherein the pharmaceutically-acceptable neutralizing agent is in an amount of more than one molar equivalent relative to the therapeutic compound.
78. The pharmaceutical composition according to embodiments 1-77, wherein the neutralizing agent is in an amount less than about 90% by weight, less than about 80% by weight, less than about 70% by weight, less than about 65% by weight, less than about 60% by weight, less than about 55% by weight, less than about 50% by weight, less than about 45% by weight, less than about 40% by weight, less than about 35% by weight, less than about 30% by weight, less than about 25% by weight, less than about 20% by weight, less than about 15% by weight, less than about 10% by weight, less than about 5% by weight, or less than about 1% by weight or about 1% to 90% by weight, about 1% to 80% by weight, about 1% to 75% by weight, about 1% to 70% by weight, about 1% to 65% by weight, about 1% to 60% by weight, about 1% to 55% by weight, about 1% to 50% by weight, about 1% to 45% by weight, about 1% to 40% by weight, about 1% to 35% by weight, about 1% to 30% by weight, about 1% to 25% by weight, about 1% to 20% by weight, about 1% to 15% by weight, about 1% to 10% by weight, about 1% to 5% by weight, about 2% to 50% by weight, about 2% to 40% by weight, about 2% to 30% by weight, about 2% to 20% by weight, about 2% to 10% by weight, about 4% to 50% by weight, about 4% to 40% by weight, about 4% to 30% by weight, about 4% to 20% by weight, about 4% to 10% by weight, about 6% to 50% by weight, about 6% to 40% by weight, about 6% to 30% by weight, about 6% to 20% by weight, about 6% to 10% by weight, about 8% to 50% by weight, about 8% to 40% by weight, about 8% to 30% by weight, about 8% to 20% by weight, about 8% to 15% by weight, or about 8% to 12% by weight.
79. The pharmaceutical composition according to embodiments 1-78, wherein the neutralizing agent is in an amount of about 0.1% to about 45% by weight, about 0.1% to about 40% by weight, about 0.1% to about 35% by weight, about 0.1% to about 30% by weight, about 0.1% to about 25% by weight, about 0.1% to about 20% by weight, about 0.1% to about 15% by weight, about 0.1% to about 10% by weight, about 0.1% to about 5% by weight, about 1% to about 45% by weight, about 1% to about 40% by weight, about 1% to about 35% by weight, about 1% to about 30% by weight, about 1% to about 25% by weight, about 1% to about 20% by weight, about 1% to about 15% by weight, about 1% to about 10% by weight, about 1% to about 5% by weight, about 5% to about 45% by weight, about 5% to about 40% by weight, about 5% to about 35% by weight, about 5% to about 30% by weight, about 5% to about 25% by weight, about 5% to about 20% by weight, about 5% to about 15% by weight, about 5% to about 10% by weight, about 10% to about 45% by weight, about 10% to about 40% by weight, about 10% to about 35% by weight, about 10% to about 30% by weight, about 10% to about 25% by weight, about 10% to about 20% by weight, about 10% to about 15% by weight, about 15% to about 45% by weight, about 15% to about 40% by weight, about 15% to about 35% by weight, about 15% to about 30% by weight, about 15% to about 25% by weight, about 15% to about 20% by weight, about 20% to about 45% by weight, about 20% to about 40% by weight, about 20% to about 35% by weight, about 20% to about 30% by weight, about 20% to about 25% by weight, about 25% to about 45% by weight, about 25% to about 40% by weight, about 25% to about 35% by weight, or about 25% to about 30% by weight.

80 A method of treating an individual with a chronic inflammation, the method comprising the step of: administering to the individual in need thereof a pharmaceutical composition according to embodiments 1-72, wherein administration results in a reduction in a symptom associated with the chronic inflammation, thereby treating the individual.

81. Use of a pharmaceutical composition according to embodiments 1-79 in the manufacture of a medicament for the treatment of a chronic inflammation.

82. Use of a pharmaceutical composition according to embodiments 1-79 for the treatment of a chronic inflammation.

83. The method according to embodiment 80 or the use according to embodiment 81 or 82, wherein the chronic inflammation is associated with acne, acid reflux/heartburn, age related macular degeneration (AMD), allergy, allergic rhinitis, Alzheimer's disease, amyotrophic lateral sclerosis, anemia, appendicitis, arteritis, arthritis, asthma. atherosclerosis, autoimmune disorders, balanitis, blepharitis, bronchiolitis, bronchitis, a bullous pemphigoid, burn, bursitis, cancer, cardiac arrest, carditis, celiac disease, cellulitis, cervicitis, cholangitis, cholecystitis, chorioamnionitis, chronic obstructive pulmonary disease (COPD), cirrhosis, colitis, congestive heart failure, conjunctivitis, cyclophosphamide-induced cystitis, cystic fibrosis, cystitis, common cold, dacryoadenitis, dementia, dermatitis, dermatomyositis, diabetes, diabetic neuropathy, diabetic retinopathy, diabetic nephropathy, diabetic ulcer, digestive system disease, eczema, emphysema, encephalitis, endocarditis, endometritis, enteritis, enterocolitis, epicondylitis, epididymitis, fasciitis, fibromyalgia, fibrosis, fibrositis, gastritis, gastroenteritis, gingivitis, glomerulonephritis, glossitis, heart disease, heart valve dysfunction, hepatitis, hidradenitis suppurativa, Huntington's disease, hyperlipidemic pancreatitis, hypertension, ileitis, infection, inflammatory bowel disease, inflammatory cardiomegaly, inflammatory neuropathy, insulin resistance, interstitial cystitis, interstitial nephritis, iritis, ischemia, ischemic heart disease, keratitis, keratoconjunctivitis, laryngitis, lupus nephritis, mastitis, mastoiditis, meningitis, metabolic syndrome (syndrome X), a migraine, multiple sclerosis, myelitis, myocarditis, myositis, nephritis, non-alcoholic steatohepatitis, obesity, omphalitis, oophoritis, orchitis, osteochondritis, osteopenia, osteomyelitis, osteoporosis, osteitis, otitis, pancreatitis, Parkinson's disease, parotitis, pelvic inflammatory disease, pemphigus vularis, pericarditis, peritonitis, pharyngitis, phlebitis, pleuritis, pneumonitis, polycystic nephritis, proctitis, prostatitis, psoriasis, pulpitis, pyelonephritis, pylephlebitis, renal failure, reperfusion injury, retinitis, rheumatic fever, rhinitis, salpingitis, sarcoidosis, sialadenitis, sinusitis, spastic colon, stenosis, stomatitis, stroke, surgical complication, synovitis, tendonitis, tendinosis, tenosynovitis, thrombophlebitis, tonsillitis, trauma, traumatic brain injury, transplant rejection, trigonitis, tuberculosis, tumor, urethritis, ursitis, uveitis, vaginitis, vasculitis, or vulvitis.

84. The method according to embodiment 80 or the use according to embodiment 81 or 82, wherein the chronic inflammation is a tissue inflammation.

85. The method according to embodiment 80 or the use according to embodiment 81 or 82, wherein the chronic inflammation is a systemic inflammation.

86. The method according to embodiment 80 or the use according to embodiment 81 or 82, wherein the chronic inflammation is an arthritis.

87. The method or use according to embodiment 83 or 86, wherein the arthritis is a monoarthritis, an oligoarthritis, or a polyarthritis.

88. The method or use according to embodiment 140 or 143, wherein the arthritis is an auto-immune disease or a non-autoimmune disease.

89. The method or use according to embodiment 83 or 86, wherein the arthritis is an osteoarthritis, a rheumatoid arthritis, a juvenile idiopathic arthritis, a septic arthritis, a spondyloarthropathy, a gout, a pseudogout, or Still's disease.

90. The method or use according to embodiment 89, wherein the spondyloarthropathy is an ankylosing spondylitis, a reactive arthritis (Reiter's syndrome), a psoriatic arthritis, an enteropathic arthritis associated with inflammatory bowel disease, a Whipple disease or a Behcet disease.

91. The method according to embodiment 80 or the use according to embodiment 81 or 82, wherein the chronic inflammation is an autoimmune disorder.

92. The method or use according to embodiment 83 or 91, wherein the autoimmune disorder is a systemic autoimmune disorder or an organ-specific autoimmune disorder.

93. The method or use according to embodiment 83 or 91, wherein the autoimmune disorder is an acute disseminated encephalomyelitis (ADEM), an Addison's disease, an allergy, an anti-phospholipid antibody syndrome (APS), an autoimmune hemolytic anemia, an autoimmune hepatitis, an autoimmune inner ear disease, a bullous pemphigoid, a celiac disease, a Chagas disease, a chronic obstructive pulmonary disease (COPD), a diabetes mellitus type 1 (IDDM), an endometriosis, a Goodpasture's syndrome, a Graves' disease, a Guillain-Barré syndrome (GBS), a Hashimoto's thyroiditis, a hidradenitis suppurativa, an idiopathic thrombocytopenic purpura, an inflammatory bowel disease, an interstitial cystitis, a lupus (including a discoid lupus erythematosus, a drug-induced lupus erythematosus. a lupus nephritis, a neonatal lupus, a subacute cutaneous lupus erythematosus, a systemic lupus erythematosus, a morphea, a multiple sclerosis (MS), a myasthenia gravis, a myopathy, a narcolepsy, a neuromyotonia, a pemphigus vulgaris, a pernicious anaemia, a primary biliary cirrhosis, a recurrent disseminated encephalomyelitis, a rheumatic fever, a schizophrenia, a scleroderma, a Sjögren's syndrome, a tenosynovitis, a vasculitis, or a vitiligo.
94. The method according to embodiment 80 or the use according to embodiment 81 or 82, wherein the chronic inflammation is a myopathy.
95. The method or use according to embodiment 93 or 94, wherein the myopathy is a dermatomyositis, an inclusion body myositis, or a polymyositis.
96. The method according to embodiment 80 or the use according to embodiment 81 or 82, wherein the chronic inflammation is a vasculitis.
97. The method or use according to embodiment 83, 93, or 96, wherein the vasculitis is vasculitis is a Buerger's disease, an arteritis, a cerebral vasculitis, a Churg-Strauss arteritis, a cryoglobulinemia, an essential cryoglobulinemic vasculitis, a giant cell arteritis, a Golfer's vasculitis, a Henoch-Schonlein purpura, a hypersensitivity vasculitis, a Kawasaki disease, a phlebitis, a microscopic polyarteritis/polyangiitis, a polyarteritis *nodosa*, a polymyalgia rheumatica (PMR), a rheumatoid vasculitis, a Takayasu arteritis, a thrombophlebitis, a Wegener's granulomatosis, or a vasculitis secondary to connective tissue disorder, or vasculitis secondary to viral infection.
98. The method according to embodiment 80 or the use according to embodiment 81 or 82, wherein the chronic inflammation is associated with a skin disorder.
99. The method or use according to embodiment 98, wherein the skin disorder is a dermatitis, an eczema, a statis dermatitis, a hidradenitis suppurativa, a psoriasis, a rosacea or a scleroderma.
100. The method or use according to embodiment 99, wherein the eczema is an atopic eczema, a contact eczema, a xerotic eczema, a seborrhoeic dermatitis, a dyshidrosis, a discoid eczema, a venous eczema, a dermatitis herpetiformis, a neurodermatitis, or an autoeczematization.
101. The method or use according to embodiment 99, wherein the psoriasis is a plaqure psoriasis, a nail psoriasis, a guttate psoriasis, a scalp psoriasis, an inverse psoriasis, a pustular psoriasis, or an erythrodermis psoriasis.
102. The method according to embodiment 80 or the use according to embodiment 81 or 82, wherein the chronic inflammation is associated with a gastrointestinal disorder.
103. The method or use according to embodiment 102, wherein the gastrointestinal disorder is an irritable bowel disease or an inflammatory bowel.
104. The method or use according to embodiment 103, wherein the inflammatory bowel is a Crohn's disease or an ulcerative colitis.
105. The method according to embodiment 80 or the use according to embodiment 81 or 82, wherein the chronic inflammation is associated with a cardiovascular disease.
106. The method or use according to embodiment 105, wherein the cardiovascular disease is a hypertension, heart valve dysfunction, congestive heart failure, myocardial infarction, a diabetic cardiac conditions, a blood vessel inflammation, arterial occlusive disease, a peripheral arterial disease, an aneurysm, an embolism, a dissection, a pseudoaneurysm, a vascular malformation, a vascular nevus, a thrombosis, a thrombphlebitis, a varicose veins, or a stroke.
107. The method according to embodiment 80 or the use according to embodiment 81 or 82, wherein the chronic inflammation is associated with a cancer.
108. The method according to embodiment 80 or the use according to embodiment 81 or 82, wherein the chronic inflammation is associated with a pharmacologically-induced inflammation.
109. The method according to embodiment 80 or the use according to embodiment 81 or 82, wherein the chronic inflammation is associated with an infection.
110. The method or use according to embodiment 83 or 109, wherein the infection is a bacterial cystitis, a bacterial encephalitis, a pandemic influenza, a viral encephalitis, a viral hepatitis A, a viral hepatitis B, or a viral hepatitis C.
111. The method according to embodiment 80 or the use according to embodiment 81 or 82, wherein the chronic inflammation is associated with a tissue or organ injury.
112. The method according to embodiment 80 or the use according to embodiment 81 or 82, wherein the chronic inflammation is associated with a transplant rejection or a graft-versus-host disease.
113. The method according to embodiment 80 or the use according to embodiment 81 or 82, wherein the chronic inflammation is associated with a Th1-mediated inflammatory disease.
114. The method according to embodiment 80 or the use according to embodiment 81 or 82, wherein the chronic inflammation is associated with chronic neurogenic inflammation.
115. The method according to embodiments 80 or 83-114 or the use according to embodiments 81-114, wherein upon administration to an individual, the pharmaceutical composition comprising the therapeutic compound according to embodiments 1-79 results in a bio-distribution of the therapeutic compound different than a bio-distribution of the therapeutic compound included in the same pharmaceutical composition, except without the pharmaceutically-acceptable adjuvant.
116. The method according to embodiments 80 or 83-115 or the use according to embodiments 81-115, wherein upon administration to an individual, the amount of the therapeutic compound of the pharmaceutical composition according to embodiments 1-79 delivered to a macrophage is at least 5% of the total amount of the therapeutic compound contained in the administered pharmaceutical composition.
117. The method according to embodiments 80 or 83-116 or the use according to embodiments 81-116, wherein upon administration to an individual, the pharmaceutical composition according to embodiments 1-79 reduces intestinal irritation by at least 5% when compared to the pharmaceutical composition according to embodiments 1-79, except without the pharmaceutically-acceptable adjuvant.
118. The method according to embodiments 80 or 83-117 or the use according to embodiments 81-117, wherein upon administration to an individual, the pharmaceutical composition according to embodiments 1-79 reduces gastric irritation by at least 5% when compared to the pharmaceutical composition according to embodiments 1-79, except without the pharmaceutically-acceptable adjuvant.

EXAMPLES

The following non-limiting examples are provided for illustrative purposes only in order to facilitate a more complete understanding of the disclosed subject matter. These examples should not be construed to limit any of the embodiments described in the present specification, including those pertaining to the pharmaceutical compositions, methods of preparing pharmaceutical compositions, or methods or uses of treating a chronic inflammation or disease associated with chronic inflammation.

Example 1 Differential Scanning Calorimetry

This example illustrates formulation of solid solution pharmaceutical composition as disclosed herein comprising a therapeutic compound.

To prepare a solid solution pharmaceutical composition disclosed herein the following general procedure was used. All ingredient, except the room temperature solid lipid, were mixed together. This mixture was heated to a temperature in the range about 50° C. to about 60° C. with stirring in order to dissolve the therapeutic compound thereby creating a solution. The room temperature solid lipid was then added to the solution and the mixture stirred until incorporated. The mixture was then allowed to solidify by cooling to room temperature. Representative formulations containing various therapeutic compounds are show in Table 1.

TABLE 1

Solid Solution Formulations of Ibuprofen

| Formulation | Therapeutic Compound | RT Liquid Lipid | Stabilizing Agent | Neutralizing Agent | RT Solid Lipid |
|---|---|---|---|---|---|
| Ibuprofen | 200 mg | — | — | — | — |
| RT Solid Lipid | — | — | — | — | 622 mg G43[a] |
| Vehicle | — | 0.26 mL M35-1[b] | 0.06 mL PEG400 | — | 260 mg G43 |
| Ibuprofen LA 3-51 | 200 mg | 0.38 mL M35-1 | 0.04 mL PEG400 | — | 160 mg G43 |
| Ibuprofen LA 3-57 | 200 mg | 0.26 mL M35-1 | 0.06 mL PEG400 | — | 260 mg G43 |
| Ibuprofen LA 35-1 | 200 mg | 0.18 mL M35-1 | 0.08 mL PEG400 | — | 380 mg G43 |
| Ibuprofen LA 35-2 | 200 mg | 0.10 mL M35-1 | 0.08 mL PEG400 | — | 460 mg G43 |
| Ibuprofen LA 35-3 | 200 mg | 0.04 mL M35-1 | 0.08 mL PEG400 | — | 520 mg G43 |

[a]G43 is GELUCIRE ® 43/01
[b]M35-1 is MAISINE ® 35-1

The mixture was then allowed to solidify by cooling to room temperature. Solidified compositions were then assessed by appearance and by Differential Scanning calorimetry (DSC).

During the course of the analysis using DSC, a general trend was observed where a formulation which solidified with a cloudy appearance formed a classic solid composition having a crystalline structure while one which solidified with a clear appearance suggested a solid solution composition having an amorphic structure. Additionally, solidified compositions with a clear appearance that were then remelted with no appearance of a precipitate where indicative of a solid solution composition having an amorphic structure.

Using the visual appearance and remelt assays, large numbers of formulations was accessed for the ability to for a solid-solution composition. A formulation that failed to form a solid, or formed a solid with a cloudy appearance were not further analyzed and discarded. Similarly, formulations were not further analyzed and discarded if a precipitate formed after remelting of a solidified compositions with a clear appearance. Formulations that formed a clear solid were also subsequently analyzed by DSC.

Data for representative ibuprofen formulations solidifying with a clear appearance are shown in FIG. 1. The DSC analysis revealed that individual components exhibited sharp, well-defined peaks. For example, ibuprofen possessed a well-defined melting point range of 75° C. to 78° C. (FIG. 1A). Similarly, a room temperature solid lipid, or hard fat, like GELUCIRE® 43/01 had a well-defined melting point range of 41° C. to 45° C. (FIG. 1B). These sharp, well defined melting point temperature ranges are indicative of a composition in a classic solid transition phase having a well-defined crystalline structure. MAISINE® 35-1 and PEG 400 are liquids at room temperature, and as such has a melting point below 20° C. For example, MAISINE® 35-1 has a melting point temperature range of about 14° C. to about 16° C. and PEG 400 has a melting point temperature range of about 4° C. to about 8° C.

Figure 1C:
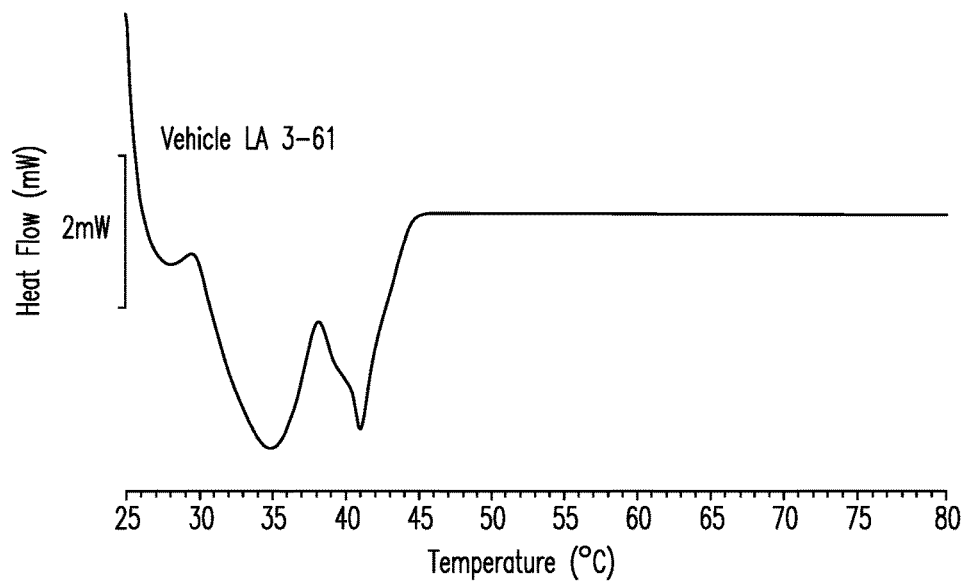

Unexpectedly, when a vehicle comprising a room temperature solid lipid (hard fat), a room temperature liquid lipid and a stabilizing agent were examined by DSC, a new melting point temperature peak appeared. For example, in addition to the GELUCIRE® 43/01 peak of 41° C. to 45° C., DSC analysis identified a new broad melting point temperature range of about 32° C. to about 38° C. (FIG. 1C). This temperature range was different than that for the individual components alone: 41° C. to 45° C. for GELUCIRE®43/01, 14° C. to 16° C. for MAISINE® 35-1, and 4° C. to 8° C. for PEG 400. These results indicate that a portion of the composition was forming into a solid solution phase instead of a classic solid phase.

Surprisingly, formulation comprising the therapeutic compound with this vehicle exhibited a broad melting range with a melting point temperature different than the individual components (FIGS. 1D-1H). Furthermore, no peaks relating to either the therapeutic compound alone or the hard fat alone were detected. For example, ibuprofen has a melting point temperature range of 75° C. to 78° C., GELUCIRE® 43/01 had a melting point of 41° C. to 45° C., MAISINE® 35-1 has a melting point temperature of 14° C. to 16° C., and PEG400 has a melting point temperature of 4° C. to 8° C. However, a formulation comprising these components results in a composition with a melting point of between 35° C. to 40° C., depending on the amounts and ratios used. In a classic mixed phase of distinct solid components, each individual peak would have been resolved, i.e., 75° C. to 78° C. for Ibuprofen, 41° C. to 45° C. and GELUCIRE® 43/01. This was not the case, these peaks disappeared altogether. The presence of a single new melting point peak, and the concomitant disappearance of the individual component melting point peaks, for the solidified composition indicates that a novel solid solution structure of therapeutic compound and room temperature solid lipid (hard fat) was formed.

Example 2 Solid Solution Pharmaceutical Compositions Comprising Artemether

This example illustrates how to make a solid solution pharmaceutical composition disclosed herein comprising Artemether.

To prepare a solid solution pharmaceutical composition disclosed herein using Artemether, the following method was performed. About 1.0 g GELUCIRE® 43/01 (Gattefosse), a waxy solid (as room temperature solid lipid) having a melting point of between 41° C. to 45° C. and comprising a mixture of saturated $C_{10}$-$C_{18}$ triglycerides, and about 0.5 mL tributyrin (as room temperature liquid lipid) were added to a vessel and heated to about 40° C. to about 50° C. with stirring until all components of the mixture were incorporated. About 40 mg Artemether was added to about 0.8 mL of this incorporated mixture and stirred until dissolved. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds.

Figure 2:
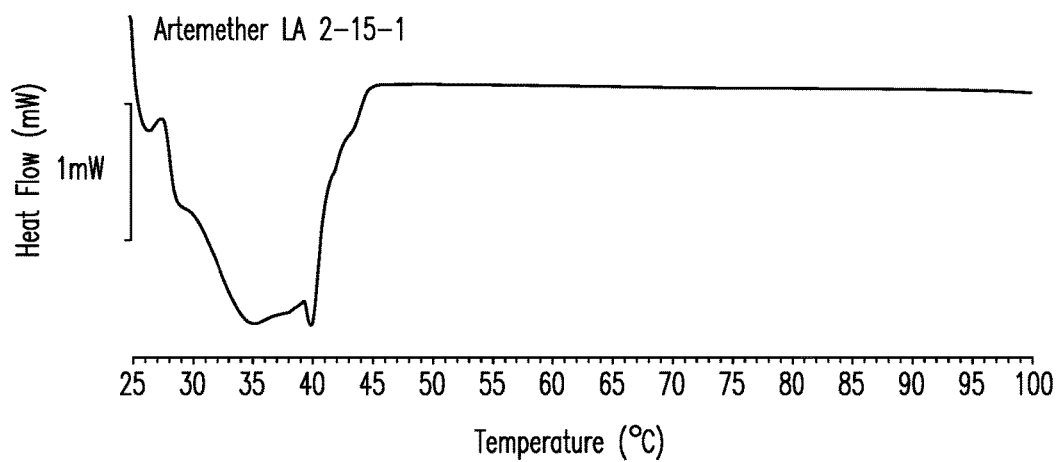
FIG. 2 shows a DSC graph of Artemether composition LA 2-15-1 exhibiting a melting point range of 35° C. to 40° C.

The formulation solidified with a clear appearance. In addition, DSC analysis indicated a new broad melting point temperature range of about 35° C. to about 40° C. (FIG. 2). This temperature range was different than that for the individual components alone: 41° C. to 45° C. for GELUCIRE® 43/01 (Gattefosse) and 86° C. to 90° C. for Artemether. Tributyrin is a liquid at room temperature, and as such has a melting point below 20° C. These results indicate that a solid solution formulation as disclosed herein comprising Artemether was formed.

Example 3 Solid Solution Pharmaceutical Compositions Comprising Aspirin

This example illustrates how to make a solid solution pharmaceutical composition disclosed herein comprising Aspirin.

To prepare a solid solution pharmaceutical composition disclosed herein using Aspirin, the following method was performed. About 120 mg Aspirin and about 0.5 mL isosorbide dimethyl ester (as stabilizing agent) were added to a vessel and heated to about 50° C. to about 60° C. with stirring until all components of the mixture were dissolved. About 1.0 g GELUCIRE® 43/01 (Gattefosse), a waxy solid (as room temperature solid lipid) having a melting point of between 41° C. to 45° C. and comprising a mixture of saturated $C_{10}$-$C_{18}$ triglycerides, was added to this solution and stirred until incorporated. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds.

Figure 3:
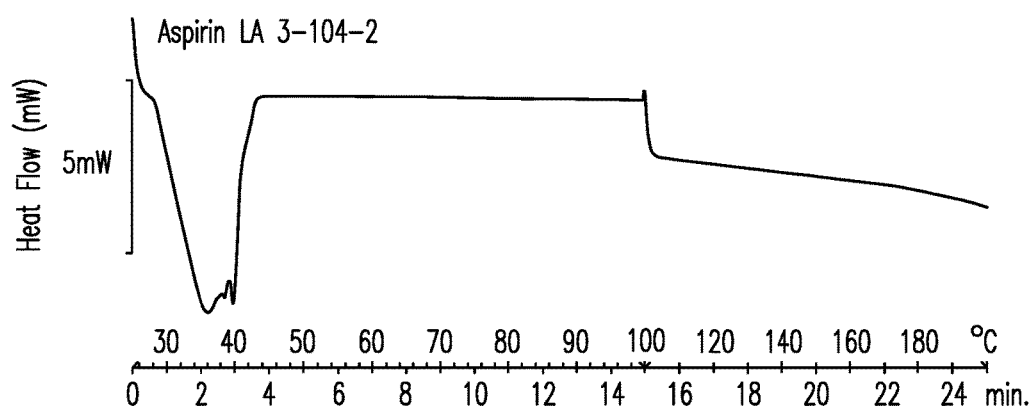
FIG. 3 shows a DSC graph of Aspirin composition LA 3-86-3 exhibiting a melting point range of 35° C. to 40° C.

The formulation solidified with a clear appearance. In addition, DSC analysis indicated a new broad melting point temperature range of about 35° C. to about 40° C. (FIG. 3). This temperature range was different than that for the individual components alone: 41° C. to 45° C. for GELUCIRE® 43/01 (Gattefosse) and 138° C. to 140° C. for Aspirin. Isosorbide dimethyl ester is a liquid at room temperature, and as such has a melting point below 20° C. These results indicate that a solid solution formulation as disclosed herein comprising Aspirin was formed.

Example 4 Solid Solution Pharmaceutical Compositions Comprising Dantrolene

This example illustrates how to make a solid solution pharmaceutical composition disclosed herein comprising Dantrolene.

To prepare a solid solution pharmaceutical composition disclosed herein using Dantrolene, the following method was performed. Add about 232.7 mg stearic acid (as neutralizing agent) to a vessel and heat to about 70° C. to about 75° C. with stirring until melted. Add about 250.2 mg Dantrolene sodium salt and 20 mL isosorbide dimethyl ester (as stabilizing agent) to melted stearic acid and stir until uniform consistency is achieved. About 20.02 g GELUCIRE®43/01 (Gattefosse), a waxy solid (as room temperature solid lipid) having a melting point of between 41° C. to 45° C. and comprising a mixture of saturated $C_{10}$-$C_{18}$ triglycerides was added to this solution and stirred until incorporated. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds.

Figure 4:
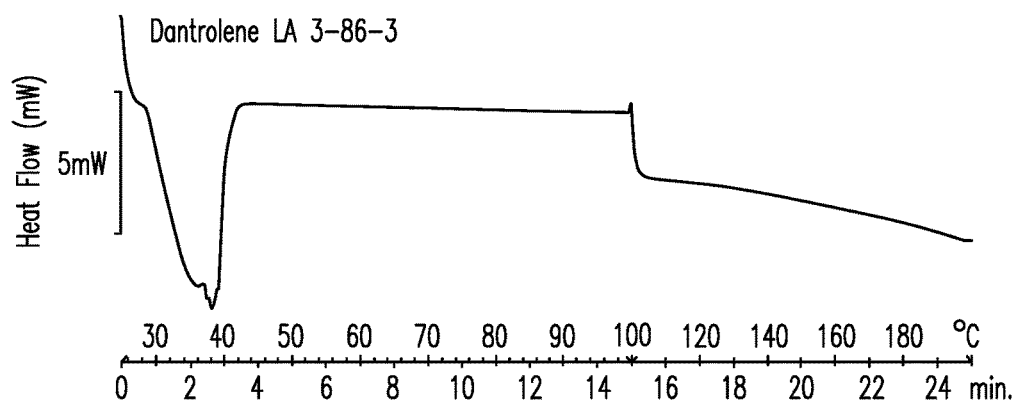
FIG. 4 shows a DSC graph of Dantrolene composition LA 3-104-2 exhibiting a melting point range of 34° C. to 39° C.

The formulation solidified with a clear appearance. In addition, DSC analysis indicated a new broad melting point temperature range of about 34° C. to about 39° C. (FIG. 4). This temperature range was different than that for the individual components alone: 41° C. to 45° C. for GELUCIRE® 43/01 (Gattefosse), stearic acid is 70° C., and 279° C. to 280° C. for Dantrolene. Isosorbide dimethyl ester is a liquid at room temperature, and as such has a melting point below 20° C. These results indicate that a solid solution formulation as disclosed herein comprising Dantrolene was formed.

To prepare a solid solution pharmaceutical composition disclosed herein using Dantrolene, the following method was performed. Add about 309.8 mg stearic acid (as neutralizing agent) to a vessel and heat to about 70° C. to about 75° C. with stirring until melted. Add about 59.6 mg Dantrolene sodium salt to melted stearic acid and stir until uniform consistency is achieved. Add 0.75 mL isosorbide dimethyl ester (as stabilizing agent) and stir mixture until all components are dissolved. About 760.3 mg GELUCIRE® 43/01 (Gattefosse), a waxy solid (as room temperature solid lipid) having a melting point of between 41° C. to 45° C. and comprising a mixture of saturated $C_{10}$-$C_{18}$ triglycerides was added to this solution and stirred until incorporated. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds. The formulation solidified with a clear appearance and remelted without forming a precipitate. These results indicate that a solid solution formulation as disclosed herein comprising Dantrolene was formed.

To prepare a solid solution pharmaceutical composition disclosed herein using Dantrolene, the following method was performed. Add about 250.2 mg stearic acid (as neutralizing agent) to a vessel and heat to about 70° C. to about 75° C. with stirring until melted. Add about 50.3 mg Dantrolene sodium salt to melted stearic acid and stir until uniform consistency is achieved. Add 5.0 mL isosorbide dimethyl ester (as stabilizing agent) and stir mixture until all components are dissolved. About 5.0 g GELUCIRE®43/01 (Gattefosse), a waxy solid (as room temperature solid lipid) having a melting point of between 41° C. to 45° C. and comprising a mixture of saturated $C_{10}$-$C_{18}$ triglycerides was added to this solution and stirred until incorporated. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds. The formulation solidified with a clear appearance and remelted without forming a precipitate. These results indicate that a solid solution formulation as disclosed herein comprising Dantrolene was formed.

To prepare a solid solution pharmaceutical composition disclosed herein using Dantrolene, the following method was performed. Add about 225.0 mg stearic acid (as neutralizing agent) to a vessel and heat to about 70° C. to about 75° C. with stirring until melted. Add about 25.1 mg Dantrolene sodium salt to melted stearic acid and stir until uniform consistency is achieved. Add 2.0 mL isosorbide dimethyl ester (as stabilizing agent) and stir mixture until all components are dissolved. About 2.07 g GELUCIRE® 43/01 (Gattefosse), a waxy solid (as room temperature solid lipid) having a melting point of between 41° C. to 45° C. and comprising a mixture of saturated $C_{10}$-$C_{18}$ triglycerides was added to this solution and stirred until incorporated. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds. The formulation solidified with a clear appearance and remelted without forming a precipitate. These results indicate that a solid solution formulation as disclosed herein comprising Dantrolene was formed.

To prepare a solid solution pharmaceutical composition disclosed herein using Dantrolene, the following method was performed. Add about 224.9 mg stearic acid (as neutralizing agent) to a vessel and heat to about 70° C. to about 75° C. with stirring until melted. Add about 25.1 mg Dantrolene sodium salt to melted stearic acid and stir until uniform consistency is achieved. Add 0.75 mL isosorbide dimethyl ester (as stabilizing agent) and stir mixture until all components are dissolved. About 304.1 mg GELUCIRE® 43/01 (Gattefosse), a waxy solid (as room temperature solid lipid) having a melting point of between 41° C. to 45° C. and comprising a mixture of saturated $C_{10}$-$C_{18}$ triglycerides was added to this solution and stirred until incorporated. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds. The formulation solidified with a clear appearance and remelted without forming a precipitate. These results indicate that a solid solution formulation as disclosed herein comprising Dantrolene was formed.

Example 5 Solid Solution Pharmaceutical Compositions Comprising Diclofenac

This example illustrates how to make a solid solution pharmaceutical composition disclosed herein comprising Diclofenac.

To prepare a solid solution pharmaceutical composition disclosed herein using Diclofenac, the following method was performed. About 119 mg Diclofenac, about 1.0 mL MAISINE® 35-1 (Gattefosse), a glyceryl monolinoleate (as room temperature liquid lipid), and about 0.3 mL isosorbide dimethyl ester (as stabilizing agent) were added to a vessel and heated to about 50° C. to about 60° C. with stirring until all components of the mixture were dissolved. About 1.0 g GELUCIRE®43/01 (Gattefosse), a waxy solid (as room temperature solid lipid) having a melting point of between 41° C. to 45° C. and comprising a mixture of saturated $C_{10}$-$C_{18}$ triglycerides, was added to this solution and stirred until incorporated. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds.

Figure 5:
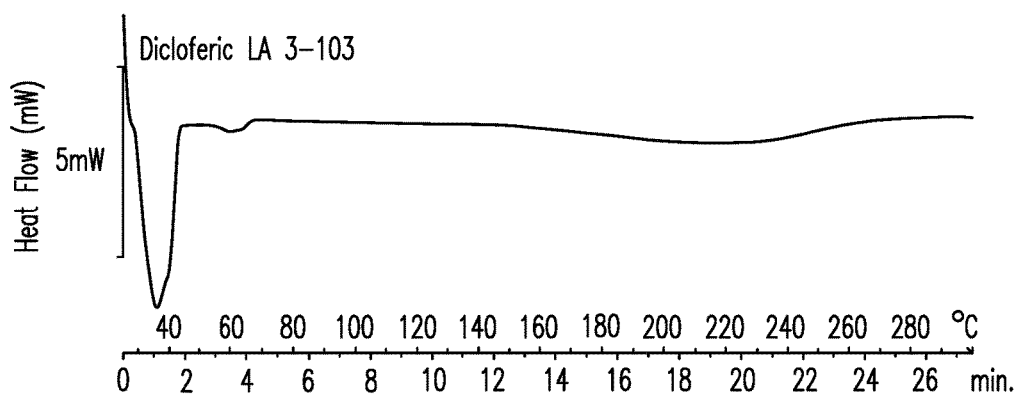
FIG. 5 shows a DSC graph of Diclofenac composition LA 3-103 exhibiting a melting point range of 35° C. to 40° C.

The formulation solidified with a clear appearance. In addition, DSC analysis indicated a new broad melting point temperature range of about 35° C. to about 40° C. (FIG. 5). This temperature range was different than that for the individual components alone: 41° C. to 45° C. for GELUCIRE® 43/01 (Gattefosse) and 157° C. to 158° C. for Diclofenac. MAISINE® 35-1 and isosorbide dimethyl ester are liquids at room temperature, and as such both have melting points below 20° C. These results indicate that a solid solution formulation as disclosed herein comprising Diclofenac was formed.

Example 6 Solid Solution Pharmaceutical Compositions Comprising Fenofibrate

This example illustrates how to make a solid solution pharmaceutical composition disclosed herein comprising Fenofibrate.

To prepare a solid solution pharmaceutical composition disclosed herein using Fenofibrate, the following method was performed. About 400 mg Fenofibrate and 4.0 g GELUCIRE®43/01 (Gattefosse), a waxy solid (as room temperature solid lipid) having a melting point of between 41° C. to 45° C. and comprising a mixture of saturated $C_{10}$-$C_{18}$ triglycerides, were added to a vessel and heated to about 45° C. to about 55° C. with stirring until all components of the mixture were incorporated. About 0.76 mL isosorbide dimethyl ester (as stabilizing agent) was added to this mixture and stirred until incorporated. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds.

Figure 6:
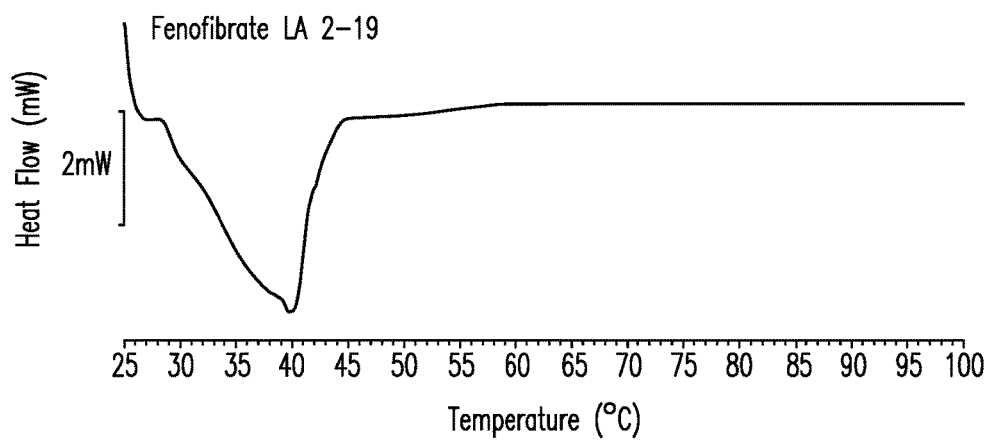
FIG. 6 shows a DSC graph of Fenofibrate composition LA 2-19 exhibiting a melting point range of 34° C. to 39° C.

The formulation solidified with a clear appearance. In addition, DSC analysis indicated a new broad melting point temperature range of about 34° C. to about 39° C. (FIG. 6). This temperature range was different than that for the individual components alone: 41° C. to 45° C. for GELUCIRE® 43/01 (Gattefosse) and 80° C. to 85° C. for Fenofibrate. Isosorbide dimethyl ester is a liquid at room temperature, and as such has a melting point below 20° C. These results indicate that a solid solution formulation as disclosed herein comprising Fenofibrate was formed.

Example 7 Solid Solution Pharmaceutical Compositions Comprising Gemifibrozil This example illustrates how to make a solid solution pharmaceutical composition disclosed herein comprising Gemifibrozil.

To prepare a solid solution pharmaceutical composition disclosed herein using Gemifibrozil, the following method was performed. About 1 g Gemifibrozil, about 0.9 mL MAISINE® 35-1 (Gattefosse), a glyceryl monolinoleate (as room temperature liquid lipid), and about 0.4 mL PEG 400 (as stabilizing agent) were added to a vessel and heated to about 50° C. to about 60° C. with stirring until all components of the mixture were dissolved. About 1.9 g GELUCIRE® 43/01 (Gattefosse), a waxy solid (as room temperature solid lipid) having a melting point of between 41° C. to 45° C. and comprising a mixture of saturated $C_{10}$-$C_{18}$ triglycerides, was added to this solution and stirred until incorporated. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds. The formulation solidified with a clear appearance and remelted without forming a precipitate. These results indicate that a solid solution formulation as disclosed herein comprising Gemifibrozil was formed.

To prepare a solid solution pharmaceutical composition disclosed herein using Gemifibrozil, the following method was performed. About 1 g Gemifibrozil and 7.5 g Cocoa Butter a waxy solid (as room temperature solid lipid) having a melting point of between 34° C. to 38° C. and comprising a mixture of saturated $C_{16}$-$C_{18}$ triglycerides, were added to a vessel and heated to about 50° C. to about 60° C. with stirring until all components of the mixture were incorporated. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds. The formulation solidified with a clear appearance and remelted without forming a precipitate. These results indicate that a solid solution formulation as disclosed herein comprising Gemifibrozil was formed.

Example 8 Solid Solution Pharmaceutical Compositions Comprising Ibuprofen

This example illustrates how to make a solid solution pharmaceutical composition disclosed herein comprising Ibuprofen.

To prepare a solid solution pharmaceutical composition disclosed herein using Ibuprofen, the following method was performed. About 1 g ibuprofen sodium salt, about 0.9 mL MAISINE® 35-1 (Gattefosse), a glyceryl monolinoleate (as room temperature liquid lipid), and about 0.4 mL PEG 400 were added to a vessel heated to about 50° C. to about 60° C. with stirring until all components of the mixture were dissolved. About 1.9 g GELUCIRE® 43/01 (Gattefosse), a waxy solid (as room temperature solid lipid) having a melting point of between 41° C. to 45° C. and comprising a mixture of saturated $C_{10}$-$C_{18}$ triglycerides, was added to this solution and stirred until incorporated. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds.

Figure 1D:
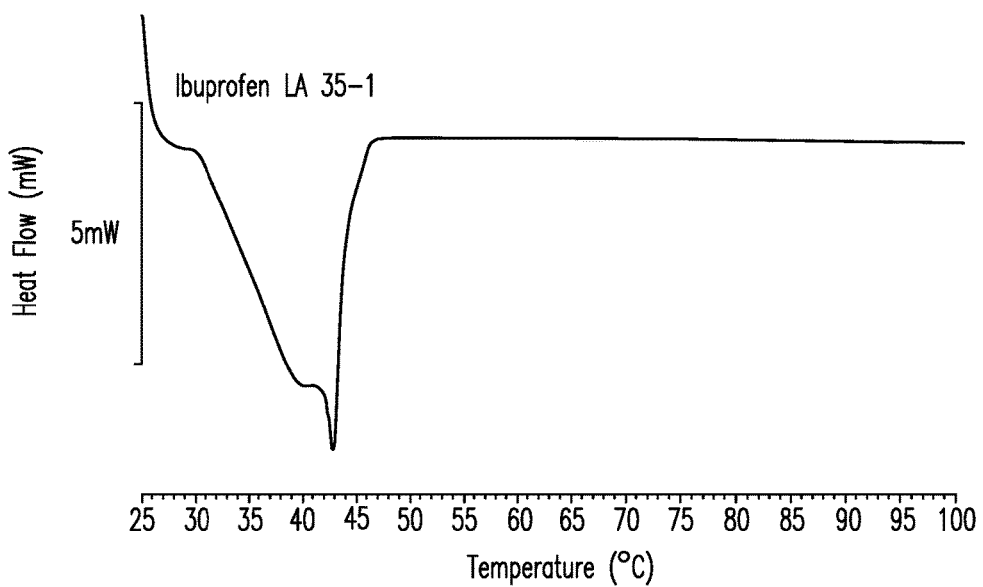

The formulation solidified with a clear appearance. In addition, DSC analysis indicated a new broad melting point temperature range of about 32° C. to about 44° C. (FIG. 1D). This temperature range was different than that for the individual components alone: 41° C. to 45° C. for GELUCIRE® 43/01 (Gattefosse) and 75° C. to 78° C. for Ibuprofen. MAISINE® 35-1 and PEG 400 are liquids at room temperature, and as such both have melting points below 20° C. These results indicate that a solid solution formulation as disclosed herein comprising Ibuprofen was formed.

To prepare a solid solution pharmaceutical composition disclosed herein using Ibuprofen, the following method was performed. About 1 g ibuprofen sodium salt, about 0.5 mL MAISINE® 35-1 (Gattefosse), a glyceryl monolinoleate (as room temperature liquid lipid), and about 0.4 mL PEG 400 were added to a vessel heated to about 50° C. to about 60° C. with stirring until all components of the mixture were dissolved. About 2.3 g GELUCIRE® 43/01 (Gattefosse), a waxy solid (as room temperature solid lipid) having a melting point of between 41° C. to 45° C. and comprising a mixture of saturated $C_{10}$-$C_{18}$ triglycerides, was added to this solution and stirred until incorporated. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds.

Figure 1E:
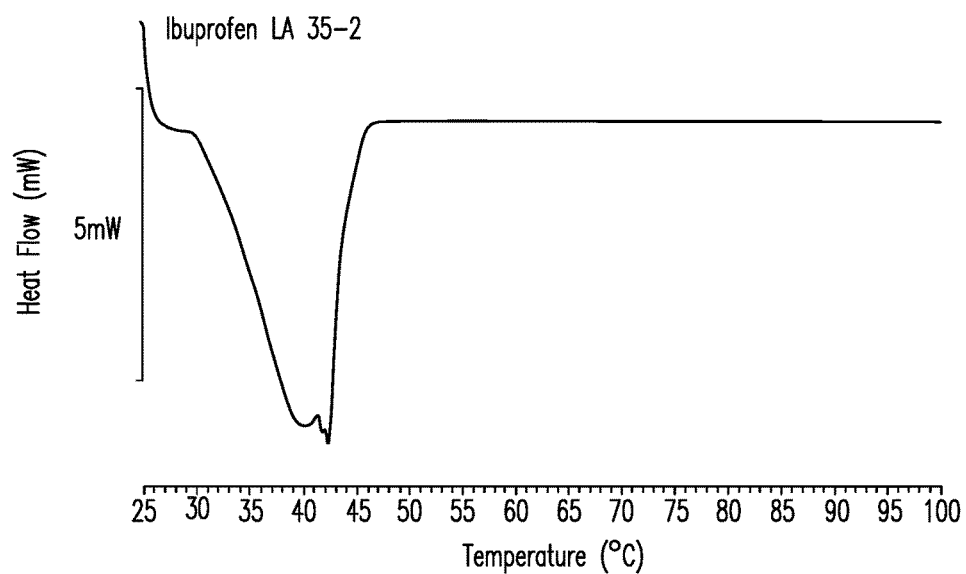

The formulation solidified with a clear appearance. In addition, DSC analysis indicated a new broad melting point temperature range of about 32° C. to about 43° C. (FIG. 1E). This temperature range was different than that for the individual components alone: 41° C. to 45° C. for GELUCIRE® 43/01 (Gattefosse) and 75° C. to 78° C. for Ibuprofen. MAISINE® 35-1 and PEG 400 are liquids at room temperature, and as such both have melting points below 20° C. These results indicate that a solid solution formulation as disclosed herein comprising Ibuprofen was formed.

To prepare a solid solution pharmaceutical composition disclosed herein using Ibuprofen, the following method was performed. About 1 g ibuprofen sodium salt, about 0.2 mL MAISINE® 35-1 (Gattefosse), a glyceryl monolinoleate (as room temperature liquid lipid), and about 0.4 mL PEG 400 were added to a vessel heated to about 50° C. to about 60° C. with stirring until all components of the mixture were dissolved. About 2.6 g GELUCIRE® 43/01 (Gattefosse), a waxy solid (as room temperature solid lipid) having a melting point of between 41° C. to 45° C. and comprising a mixture of saturated $C_{10}$-$C_{18}$ triglycerides, was added to this solution and stirred until incorporated. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds.

Figure 1F:
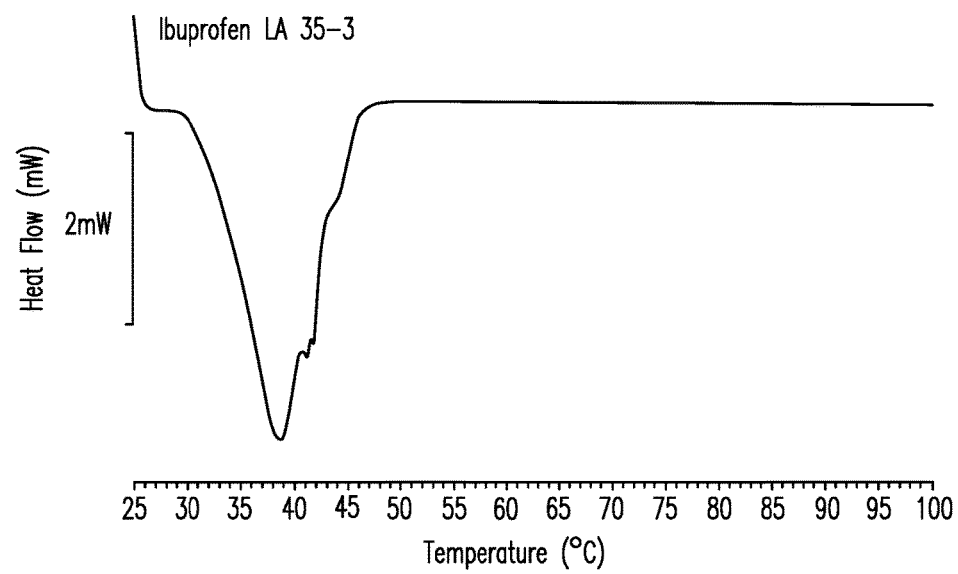

The formulation solidified with a clear appearance. In addition, DSC analysis indicated a new broad melting point temperature range of about 32° C. to about 42° C. (FIG. 1F). This temperature range was different than that for the individual components alone: 41° C. to 45° C. for GELUCIRE® 43/01 (Gattefosse) and 75° C. to 78° C. for Ibuprofen. MAISINE® 35-1 and PEG 400 are liquids at room temperature, and as such both have melting points below 20°

C. These results indicate that a solid solution formulation as disclosed herein comprising Ibuprofen was formed.

To prepare a solid solution pharmaceutical composition disclosed herein using Ibuprofen, the following method was performed. About 5 g ibuprofen sodium salt, about 9.5 mL MAISINE® 35-1 (Gattefosse), a glyceryl monolinoleate (as room temperature liquid lipid), and about 1.0 mL PEG 400 were added to a vessel heated to about 50° C. to about 60° C. with stirring until all components of the mixture were dissolved. About 4.0 g GELUCIRE® 43/01 (Gattefosse), a waxy solid (as room temperature solid lipid) having a melting point of between 41° C. to 45° C. and comprising a mixture of saturated $C_{10}$-$C_{18}$ triglycerides, was added to this solution and stirred until incorporated. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds.

Figure 1G:
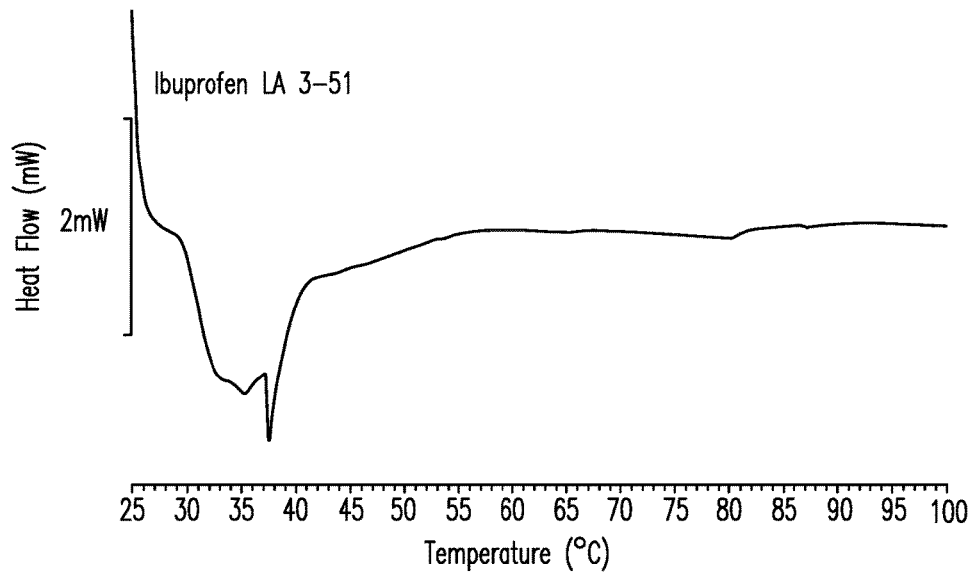

The formulation solidified with a clear appearance. In addition, DSC analysis indicated a new broad melting point temperature range of about 32° C. to about 38° C. (FIG. 1G). This temperature range was different than that for the individual components alone: 41° C. to 45° C. for GELUCIRE® 43/01 (Gattefosse) and 75° C. to 78° C. for Ibuprofen. MAISINE® 35-1 and PEG 400 are liquids at room temperature, and as such both have melting points below 20° C. These results indicate that a solid solution formulation as disclosed herein comprising Ibuprofen was formed.

To prepare a solid solution pharmaceutical composition disclosed herein using Ibuprofen, the following method was performed. About 5 g ibuprofen sodium salt, about 6.5 mL MAISINE® 35-1 (Gattefosse), a glyceryl monolinoleate (as room temperature liquid lipid), and about 1.5 mL PEG 400 were added to a vessel heated to about 50° C. to about 60° C. with stirring until all components of the mixture were dissolved. About 6.5 g GELUCIRE® 43/01 (Gattefosse), a waxy solid (as room temperature solid lipid) having a melting point of between 41° C. to 45° C. and comprising a mixture of saturated $C_{10}$-$C_{18}$ triglycerides, was added to this solution and stirred until incorporated. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds.

Figure 1H:
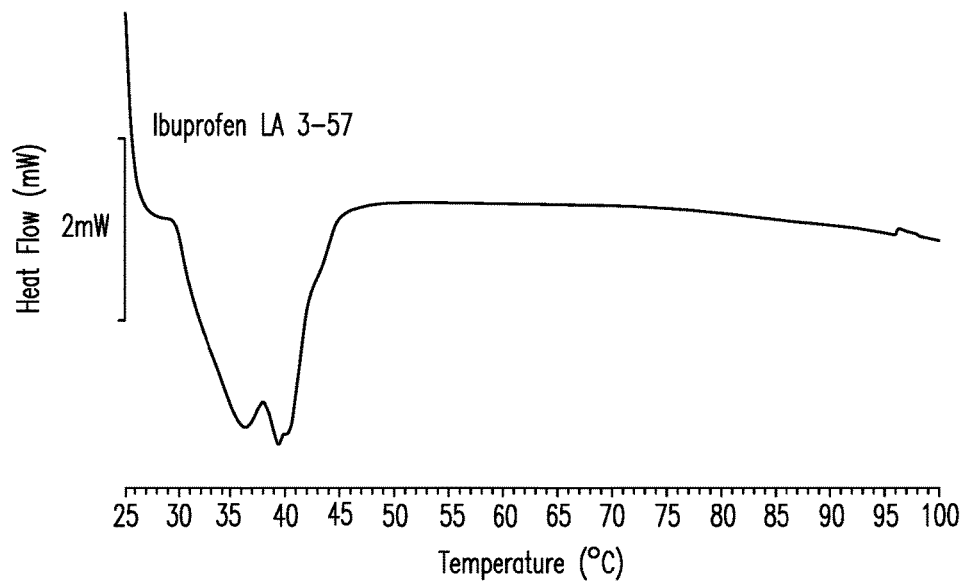

The formulation solidified with a clear appearance. In addition, DSC analysis indicated a new broad melting point temperature range of about 32° C. to about 42° C. (FIG. 1H). This temperature range was different than that for the individual components alone: 41° C. to 45° C. for GELUCIRE® 43/01 (Gattefosse) and 75° C. to 78° C. for Ibuprofen. MAISINE® 35-1 and PEG 400 are liquids at room temperature, and as such both have melting points below 20° C. These results indicate that a solid solution formulation as disclosed herein comprising Ibuprofen was formed.

To prepare a solid solution pharmaceutical composition disclosed herein using Ibuprofen, the following method was performed. About 1 g ibuprofen sodium salt, about 0.9 mL MAISINE® 35-1 (Gattefosse), a glyceryl monolinoleate (as room temperature liquid lipid), about 0.4 mL PEG 400, and about 0.3 mL propylene glycol were added to a vessel heated to about 50° C. to about 60° C. with stirring until all components of the mixture were dissolved. About 1.9 g GELUCIRE® 43/01 (Gattefosse), a waxy solid (as room temperature solid lipid) having a melting point of between 41° C. to 45° C. and comprising a mixture of saturated $C_{10}$-$C_{18}$ triglycerides, was added to this solution and stirred until incorporated. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds. The formulation solidified with a clear appearance and remelted without forming a precipitate. These results indicate that a solid solution formulation as disclosed herein comprising Ibuprofen was formed.

To prepare a solid solution pharmaceutical composition disclosed herein using Ibuprofen, the following method was performed. About 5 g ibuprofen free acid, about 5 g ibuprofen sodium salt, about 8 mL MAISINE® 35-1 (Gattefosse), a glyceryl monolinoleate (as room temperature liquid lipid), about 3 mL PEG 400, and about 1 mL propylene glycol were added to a vessel heated to about 50° C. to about 60° C. with stirring until all components of the mixture were dissolved. About 19 g GELUCIRE® 43/01 (Gattefosse), a waxy solid (as room temperature solid lipid) having a melting point of between 41° C. to 45° C. and comprising a mixture of saturated $C_{10}$-$C_{18}$ triglycerides, was added to this solution and stirred until incorporated. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds. The formulation solidified with a clear appearance and remelted without forming a precipitate. These results indicate that a solid solution formulation as disclosed herein comprising Ibuprofen was formed.

Example 9 Solid Solution Pharmaceutical Compositions Comprising Lidocaine

This example illustrates how to make a solid solution pharmaceutical composition disclosed herein comprising Lidocaine.

To prepare a solid solution pharmaceutical composition disclosed herein using Lidocaine, the following method was performed. About 200 mg Lidocaine base and about 2.0 mL isosorbide dimethyl ester (as stabilizing agent) were added to a vessel and heated to about 50° C. to about 60° C. with stirring until all components of the mixture were dissolved. About 8.8 g GELUCIRE®43/01 (Gattefosse), a waxy solid (as room temperature solid lipid) having a melting point of between 41° C. to 45° C. and comprising a mixture of saturated $C_{10}$-$C_{18}$ triglycerides, was added to this solution and stirred until incorporated. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds.

Figure 7:
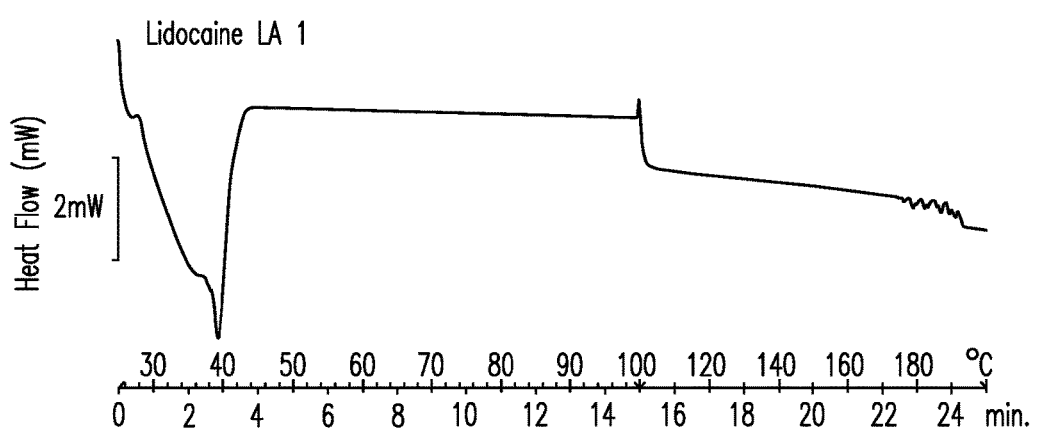
FIG. 7 shows a DSC graph of Lidocaine composition LA 3-101-2 exhibiting a melting point range of 34° C. to 40° C.

The formulation solidified with a clear appearance. In addition, DSC analysis indicated a new broad melting point temperature range of about 34° C. to about 40° C. (FIG. 7). This temperature range was different than that for the individual components alone: 41° C. to 45° C. for GELUCIRE® 43/01 (Gattefosse) and 66° C. to 69° C. for Lidocaine. Isosorbide dimethyl ester is a liquid at room temperature, and as such has a melting point below 20° C. These results indicate that a solid solution formulation as disclosed herein comprising Lidocaine was formed.

To prepare a solid solution pharmaceutical composition disclosed herein using Lidocaine, the following method was performed. About 250.1 mg Lidocaine base and about 1.74 mL isosorbide dimethyl ester (as stabilizing agent) were added to a vessel and heated to about 50° C. to about 60° C. with stirring until all components of the mixture were dissolved. About 8.72 g GELUCIRE® 43/01 (Gattefosse), a waxy solid (as room temperature solid lipid) having a melting point of between 41° C. to 45° C. and comprising a mixture of saturated $C_{10}$-$C_{18}$ triglycerides, was added to this solution and stirred until incorporated. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds.

To prepare a solid solution pharmaceutical composition disclosed herein using Lidocaine, the following method was performed. About 500.4 mg Lidocaine base and about 1.74 mL isosorbide dimethyl ester (as stabilizing agent) were added to a vessel and heated to about 50° C. to about 60° C. with stirring until all components of the mixture were dissolved. About 8.5 g GELUCIRE®43/01 (Gattefosse), a waxy solid (as room temperature solid lipid) having a melting point of between 41° C. to 45° C. and comprising a mixture of saturated $C_{10}$-$C_{18}$ triglycerides, was added to this solution and stirred until incorporated. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds.

To prepare a solid solution pharmaceutical composition disclosed herein using Lidocaine, the following method was performed. About 250.4 mg Lidocaine base and about 0.87 mL isosorbide dimethyl ester (as stabilizing agent) were added to a vessel and heated to about 50° C. to about 60° C. with stirring until all components of the mixture were incorporated. Separately, About 250.1 mg Prilocaine HCl base, 0.13 mL triethanolamine (as neutralizing agent), and about 0.87 mL isosorbide dimethyl ester (as stabilizing agent) were added to a vessel and heated to about 50° C. to about 60° C. with stirring until all components of the mixture were incorporated. The Lidocaine and Prilocaine mixtures were combined and heated to about 50° C. to about 60° C. with stirring until all components were dissolved. About 8.49 g GELUCIRE® 43/01 (Gattefosse), a waxy solid (as room temperature solid lipid) having a melting point of between 41° C. to 45° C. and comprising a mixture of saturated $C_{10}$-$C_{18}$ triglycerides, was added to this solution and stirred until incorporated. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds.

Example 10 Solid Solution Pharmaceutical Compositions Comprising Nabumetone

This example illustrates how to make a solid solution pharmaceutical composition disclosed herein comprising Nabumetone.

To prepare a solid solution pharmaceutical composition disclosed herein using Nabumetone, the following method was performed. About 126 mg Nabumetone and about 0.5 mL MAISINE® 35-1 (Gattefosse), a glyceryl monolinoleate (as room temperature liquid lipid), were added to a vessel and heated to about 50° C. to about 60° C. with stirring until all components of the mixture were dissolved. About 1.0 g GELUCIRE® 43/01 (Gattefosse), a waxy solid (as room temperature solid lipid) having a melting point of between 41° C. to 45° C. and comprising a mixture of saturated $C_{10}$-$C_{18}$ triglycerides, was added to this solution and stirred until incorporated. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds.

Figure 8:
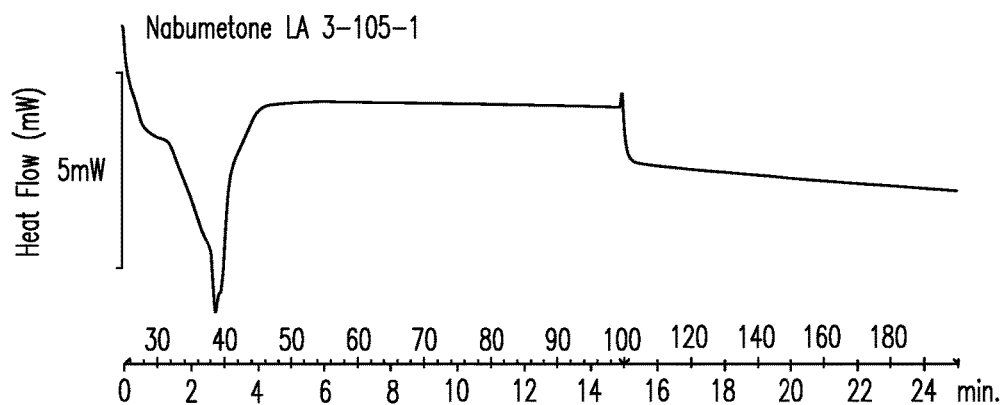
FIG. 8 shows a DSC graph of Nabumetone composition LA 3-105-1 exhibiting a melting point range of 35° C. to 40° C.

The formulation solidified with a clear appearance. In addition, DSC analysis indicated a new broad melting point temperature range of about 35° C. to about 40° C. (FIG. 8). This temperature range was different than that for the individual components alone: 41° C. to 45° C. for GELUCIRE® 43/01 (Gattefosse) and 80° C. to 81° C. for Nabumetone. MAISINE® 35-1 is a liquid at room temperature, and as such has a melting point below 20° C. These results indicate that a solid solution formulation as disclosed herein comprising Nabumetone was formed.

Example 11 Solid Solution Pharmaceutical Compositions Comprising Naproxen

This example illustrates how to make a solid solution pharmaceutical composition disclosed herein comprising Naproxen.

To prepare a solid solution pharmaceutical composition disclosed herein using Naproxen, the following method was performed. About 250.1 mg Naproxen and about 0.75 mL MAISINE® 35-1 (Gattefosse), a glyceryl monolinoleate (as room temperature liquid lipid), were added to a vessel and heated to about 50° C. to about 60° C. with stirring until all components of the mixture were dissolved. About 750.9 mg GELUCIRE® 43/01 (Gattefosse), a waxy solid (as room temperature solid lipid) having a melting point of between 41° C. to 45° C. and comprising a mixture of saturated $C_{10}$-$C_{18}$ triglycerides, was added to this solution and stirred until incorporated. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds. The formulation solidified with a clear appearance. These results indicate that a solid solution formulation as disclosed herein comprising Naproxen was formed.

To prepare a solid solution pharmaceutical composition disclosed herein using Naproxen, the following method was performed. About 650.5 mg Naproxen and about 1.2 mL MAISINE® 35-1 (Gattefosse), a glyceryl monolinoleate (as room temperature liquid lipid), were added to a vessel and heated to about 50° C. to about 60° C. with stirring until all components of the mixture were dissolved. About 1.234 g GELUCIRE® 43/01 (Gattefosse), a waxy solid (as room temperature solid lipid) having a melting point of between 41° C. to 45° C. and comprising a mixture of saturated $C_{10}$-$C_{18}$ triglycerides, was added to this solution and stirred until incorporated. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds.

Figure 9:
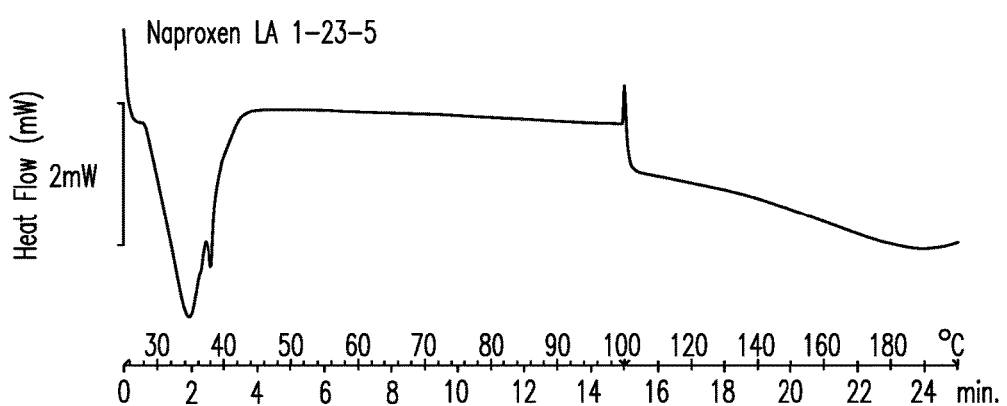
FIG. 9 shows a DSC graph of Naproxen composition LA 1-23-5 exhibiting a melting point range of 30° C. to 39° C.

The formulation solidified with a clear appearance. In addition, DSC analysis indicated a new broad melting point temperature range of about 30° C. to about 39° C. (FIG. 9). This temperature range was different than that for the individual components alone: 41° C. to 45° C. for GELUCIRE® 43/01 (Gattefosse) and 153° C. to 154° C. for Naproxen. MAISINE® 35-1 is a liquid at room temperature, and as such has a melting point below 20° C. These results indicate that a solid solution formulation as disclosed herein comprising Naproxen was formed.

Example 12 Solid Solution Pharmaceutical Compositions Comprising Pentoxifylline This example illustrates how to make a solid solution pharmaceutical composition disclosed herein comprising Pentoxifylline.

To prepare a solid solution pharmaceutical composition disclosed herein using Pentoxifylline, the following method was performed. About 208 mg Pentoxifylline, about 1.0 mL MAISINE® 35-1 (Gattefosse), a glyceryl monolinoleate (as room temperature liquid lipid), and about 0.2 mL isosorbide dimethyl ester (as stabilizing agent) were added to a vessel and heated to about 50° C. to about 60° C. with stirring until all components of the mixture were dissolved. About 1.0 g GELUCIRE®43/01 (Gattefosse), a waxy solid (as room temperature solid lipid) having a melting point of between 41° C. to 45° C. and comprising a mixture of saturated $C_{10}$-$C_{18}$ triglycerides, was added to this solution and stirred until incorporated. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds. The formulation solidified with a clear appearance and remelted without forming a precipitate. These results indicate that a solid solution formulation as disclosed herein comprising Pentoxifylline was formed.

Example 13 Solid Solution Pharmaceutical Compositions Comprising Salbutamol

This example illustrates how to make a solid solution pharmaceutical composition disclosed herein comprising Salbutamol.

To prepare a solid solution pharmaceutical composition disclosed herein using Salbutamol, the following method was performed. About 61 mg Salbutamol, about 0.6 mL MAISINE® 35-1 (Gattefosse), a glyceryl monolinoleate (as room temperature liquid lipid), 1.0 mL isosorbide dimethyl ether (as stabilizing agent), and about 1.0 mL absolute ethanol (as stabilizing agent) were added to a vessel and heated to about 50° C. to about 60° C. with stirring until all components of the mixture were dissolved. About 10 g GELUCIRE® 43/01 (Gattefosse), a waxy solid (as room temperature solid lipid) having a melting point of between 41° C. to 45° C. and comprising a mixture of saturated $C_{10}$-$C_{18}$ triglycerides, was added to this solution and stirred until incorporated. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds.

Figure 10:
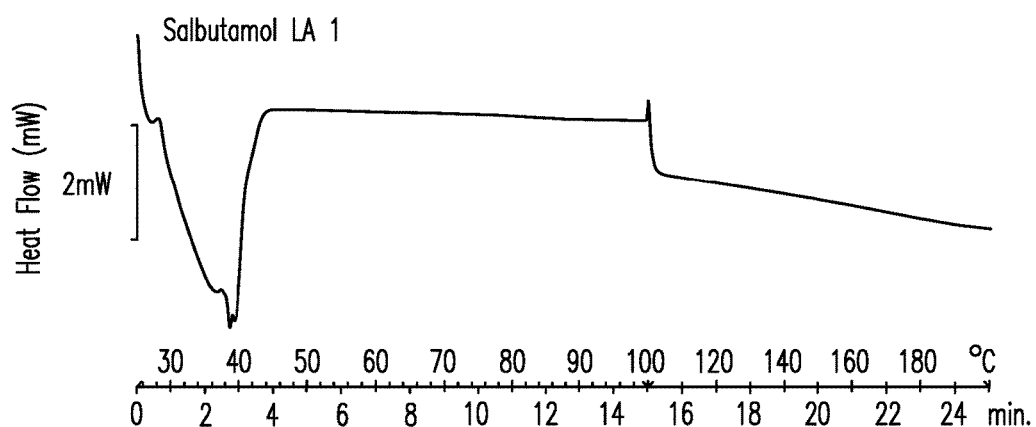
FIG. 10 shows a DSC graph of Salbutamol composition LA 1 exhibiting a melting point range of 32° C. to 40° C.

The formulation solidified with a clear appearance. In addition, DSC analysis indicated a new broad melting point temperature range of about 32° C. to about 40° C. (FIG. 10). This temperature range was different than that for the individual components alone: 41° C. to 45° C. for GELUCIRE® 43/01 (Gattefosse) and 157° C. to 158° C. for Salbutamol. MAISINE® 35-1, isosorbide dimethyl ether, and absolute ethanol are liquids at room temperature, and as such all have melting points below 20° C. These results indicate that a solid solution formulation as disclosed herein comprising Salbutamol was formed.

Example 14 Solid Solution Pharmaceutical Compositions Comprising Salmeterol

This example illustrates how to make a solid solution pharmaceutical composition disclosed herein comprising Salmeterol.

To prepare a solid solution pharmaceutical composition disclosed herein using Salmeterol, the following method was performed. About 11 mg Salmeterol xinafoate, about 1.0 mL MAISINE® 35-1 (Gattefosse), a glyceryl monolinoleate (as room temperature liquid lipid), and about 1.0 mL absolute ethanol (as stabilizing agent) were added to a vessel and heated to about 50° C. to about 60° C. with stirring until all components of the mixture were dissolved. About 2.04 g GELUCIRE® 43/01 (Gattefosse), a waxy solid (as room temperature solid lipid) having a melting point of between 41° C. to 45° C. and comprising a mixture of saturated $C_{10}$-$C_{18}$ triglycerides, was added to this solution and stirred until incorporated. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds.

Figure 11:
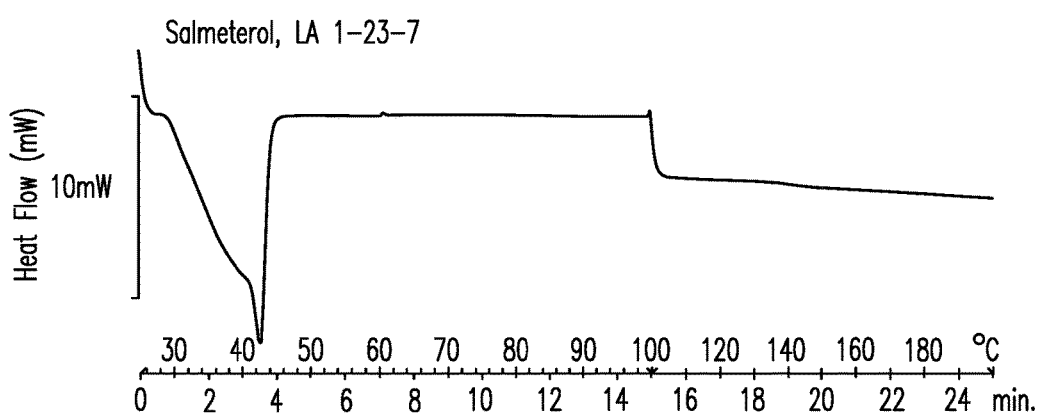
FIG. 11 shows a DSC graph of Salmeterol composition LA 1-23-7 exhibiting a melting point range of 34° C. to 43° C.

The formulation solidified with a clear appearance. In addition, DSC analysis indicated a new broad melting point temperature range of about 34° C. to about 43° C. (FIG. 11). This temperature range was different than that for the individual components alone: 41° C. to 45° C. for GELUCIRE® 43/01 (Gattefosse) and 137° C. to 138° C. for Salmeterol. MAISINE® 35-1 and absolute ethanol are liquids at room temperature, and as such both have melting points below 20° C. These results indicate that a solid solution formulation as disclosed herein comprising Salmeterol was formed.

Example 15 Solid Solution Pharmaceutical Compositions Comprising Simvastatin This example illustrates how to make a solid solution pharmaceutical composition disclosed herein comprising Simvastatin.

To prepare a solid solution pharmaceutical composition disclosed herein using Simvastatin, the following method was performed. About 200 mg Simvastatin and about 2.5 mL MAISINE® 35-1 (Gattefosse), a glyceryl monolinoleate (as room temperature liquid lipid) were added to a vessel and heated to about 50° C. to about 60° C. with stirring until all components of the mixture were dissolved. About 5 g GELUCIRE® 43/01 (Gattefosse), a waxy solid (as room temperature solid lipid) having a melting point of between 41° C. to 45° C. and comprising a mixture of saturated $C_{10}$-$C_{18}$ triglycerides, was added to this solution and stirred until incorporated. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds.

Figure 12:
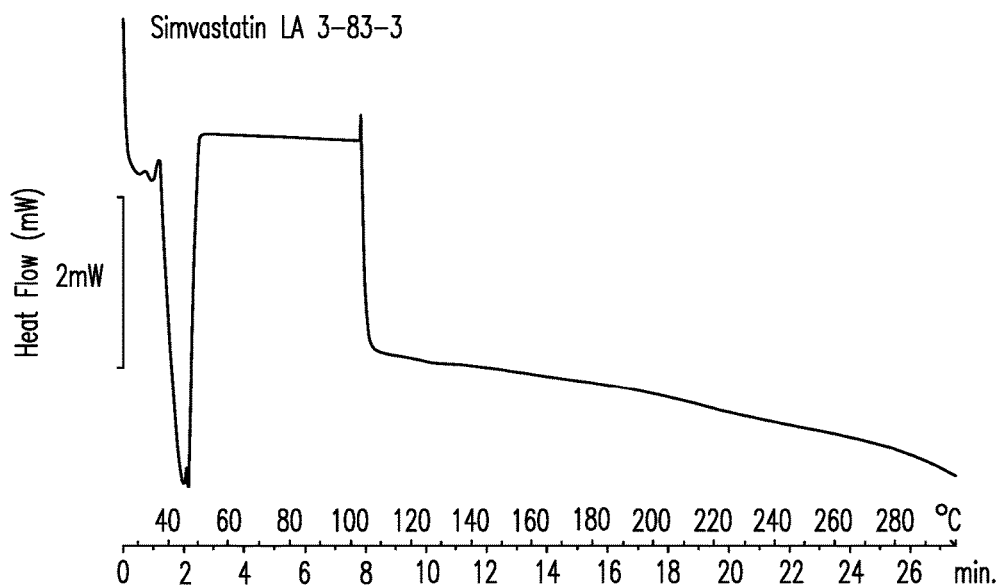
FIG. 12 shows a DSC graph of Simvastatin composition LA 3-83-3 exhibiting a melting point range of 32° C. to 43° C.

The formulation solidified with a clear appearance. In addition, DSC analysis indicated a new broad melting point temperature range of about 32° C. to about 42° C. (FIG. 12). This temperature range was different than that for the individual components alone: 41° C. to 45° C. for GELUCIRE® 43/01 (Gattefosse) and 135° C. to 138° C. for Simvastatin. MAISINE® 35-1 and absolute ethanol are liquids at room temperature, and as such both have melting points below 20° C. These results indicate that a solid solution formulation as disclosed herein comprising Simvastatin was formed.

Example 16 Solid Solution Pharmaceutical Compositions Comprising Telmisartan This example illustrates how to make a solid solution pharmaceutical composition disclosed herein comprising Telmisartan.

To prepare a solid solution pharmaceutical composition disclosed herein using Telmisartan, the following method was performed. About 60.1 mg Telmisartan and about 2.0 mL isosorbide dimethyl ether (as stabilizing agent) were added to a vessel and heated to about 50° C. to about 60° C. with stirring until all components of the mixture were dissolved. About 2.03 g GELUCIRE® 43/01 (Gattefosse), a waxy solid (as room temperature solid lipid) having a melting point of between 41° C. to 45° C. and comprising a mixture of saturated $C_{10}$-$C_{18}$ triglycerides, was added to this solution and stirred until incorporated. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds. The formulation solidified with a clear appearance and remelted without forming a precipitate. These results indicate that a solid solution formulation as disclosed herein comprising Telmisartan was formed.

To prepare a solid solution pharmaceutical composition disclosed herein using Telmisartan, the following method was performed. About 160.2 mg Telmisartan, about 1.0 mL MAISINE® 35-1 (Gattefosse), a glyceryl monolinoleate (as room temperature liquid lipid), and about 1.0 mL absolute ethanol (as stabilizing agent) were added to a vessel and heated to about 50° C. to about 60° C. with stirring until all components of the mixture were dissolved. About 2.03 g GELUCIRE®43/01 (Gattefosse), a waxy solid (as room temperature solid lipid) having a melting point of between 41° C. to 45° C. and comprising a mixture of saturated $C_{10}$-$C_{18}$ triglycerides, was added to this solution and stirred until incorporated. The heated mixture was then cooled to about 37° C. to about 40° C., and aliquoted by pouring into molds and cooled to room temperature. Alternatively, the mixture can be cooled to room temperature and then subsequently reheated to about 40° C. to about 45° C. for aliquoting into molds.

Figure 13:
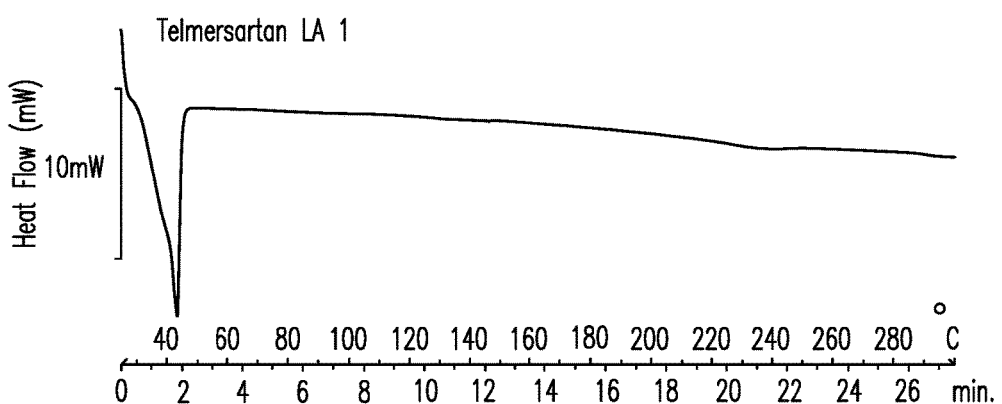
FIG. 13 shows a DSC graph of Telmisartan composition LA 1 exhibiting a melting point range of 34° C. to 43° C.

The formulation solidified with a clear appearance. In addition, DSC analysis indicated a new broad melting point temperature range of about 34° C. to about 43° C. (FIG. 13). This temperature range was different than that for the individual components alone: 41° C. to 45° C. for GELUCIRE® 43/01 (Gattefosse) and 261° C. to 263° C. for Telmisartan. MAISINE® 35-1 and absolute ethanol are liquids at room temperature, and as such both have melting points below 20° C. These results indicate that a solid solution formulation as disclosed herein comprising Telmisartan was formed.

Example 17 Macrophage Uptake Experiment

This example illustrates that a solid solution pharmaceutical composition disclosed herein preferentially targets a therapeutic compound to the immune system.

Cultures of U937 monocyte cell line were grown in RPMI-1640 supplemented with 10% fetal calf serum (FCS) until the cells reached 90% confluent monolayer. These cells were then treated with PMA and incubated in a 37° C. incubator under 5% carbon dioxide until the cells differentiated into macrophages. Monolayers of macrophages were washed with fresh medium and then 3 mL of one of the following test solutions were added: A) solid solution formulation as disclosed herein comprising ibuprofen, GELUCIRE® 43/01 (Gattefosse), MAISINE® 35-1 (Gattefosse), and PEG 400; B) liquid formulation disclosed herein comprising ibuprofen, rapeseed oil and ethanol; C) ibuprofen free acid; and D) vehicle with no therapeutic compound. After incubation for 45 minutes the test solution supernatants were removed and saved for analysis, and the cells were then washed in PBS several times and lysed using two cycles of freeze-thawing. Therapeutic compound concentration present in the test solution, test solution supernatant, and cell lysate fractions was measured by HPLC. The percentage therapeutic compound taken up by the macrophages was calculated using the following formula: % therapeutic compound adsorbed=100×(compound mass recovered from cell lysate)/(compound mass delivered in test solution compound mass recovered from test solution supernatant). Results are shown in the Table 1 below. These results indicate that mean uptake of a therapeutic compound by macrophage increase 550% or more using the formulations of the pharmaceutical compositions presently claimed relative to compositions not formulated in this manner.

TABLE 3

Macrophage Uptake of Therapeutic Compound

| Formulation | N | Mean Mass Compound Uptake | % Increase Compound Uptake |
|---|---|---|---|
| A | 2 | 2.4% | 600% |
| B | 2 | 2.2% | 550% |
| C | 2 | 0.4% | — |
| D | 2 | 0.0% | — |

Example 18 Animal Model for Intestinal Erosion

To assess whether a pharmaceutical composition disclosed herein reduced gastric irritation, experiments were conducted using an intestinal erosion murine model.

Sprague-Dawley rats were divided into seven experimental groups containing five animals each. After fasting overnight, the animals were challenged with one with one of seven different treatments. Group A was a control in which each mouse was orally administered 1% methylcellulose/0.5% polysorbate 80 vehicle only. Group B was a control in which each mouse was orally administered solvent/adjuvant vehicle only (gavage of 10% ethanol and 90% linseed oil). Group C was a control in which each mouse was orally administered 150 mg/kg aspirin. Group D was a control in which each mouse was orally administered 100 mg/kg ibuprofen suspended in 1% methylcellulose/0.5% polysorbate 80. Group E was the experimental group in which each mouse was administered a pharmaceutical composition disclosed herein (BC1054-100) comprising 100 mg/kg of ibuprofen, 10% ethanol, and 90% linseed oil. Group F was a control in which each mouse was orally administered 100 mg/kg ibuprofen suspended in 1% methylcellulose/0.5% polysorbate 80. Group G was the experimental group in which each mouse was administered a pharmaceutical composition disclosed herein (BC1054-200) comprising 200 mg/kg of ibuprofen, 10% ethanol, and 90% linseed oil. Animals were sacrificed 4 hours after treatment and the stomachs were examined for degree of hemorrhage and severity of mucosal erosive lesions. Gastric irritation was scored as follows: 0, no lesions; 1, hyperemia; 2, one or two slight lesions; 3, more than two slight lesions or severe lesions; and 4, very severe lesions. A score of 50% or more relative to Group C (aspirin-treated control group), which was set to 100%, was considered a positive score for gastric irritation.

Results are shown in Table 4. Group D (100 mg/kg of ibuprofen-treated control group) and Group F (200 mg/kg of ibuprofen-treated control group) produced gastric lesions that were 75% and 95%, respectively, severe as those induced by Group C (aspirin-treated control group). However, Group E (BC1054-100-treated experimental group) and Group G (BC1054-200-treated experimental group) produced gastric lesions that were 20% and 40%, respectively, as severe as those associated with Group C (aspirin-treated control group). These results demonstrate that that a pharmaceutical composition disclosed herein reduced the extent to which a therapeutic compound may cause mucosal lesions and cause gastric irritation.

TABLE 4

Results from Intestinal Erosion Assay

| Group | Mean Ulceration Score | % Aspirin Erosion |
|---|---|---|
| A | 0 | 0 |
| B | 0 | 0 |
| C | 4 | (100) |
| D | 3 | 75[1] |
| E | 0.8 | 20 |
| F | 3.8 | 95[1] |
| G | 1.6 | 40 |

[1]Positive score for gastric erosion.

Example 19 Animal Model for Inflammatory Bowel Disease

To assess the effectiveness of a pharmaceutical composition disclosed herein in treating an inflammatory bowel disease, experiments were conducted using a TBS-induced colitis murine model.

C57Bl/6 male mice (6-7 weeks old) were divided into seven experimental groups containing at least ten animals each. On day 0, colitis was induced in mice from Groups B-G by intrarectal administration of 100 µL of TNBS (4 mg) in 50% ethanol under isoflurane anesthesia. Animals were dosed either once or three times a day from day −1 to day 5 with one of seven different treatments. Group A was a control in which each mouse was orally administered ethanol vehicle only. Group B was a control in which each mouse was orally administered 1% methylcellulose vehicle only. Group C was a control in which each mouse was orally administered solvent/adjuvant vehicle only (gavage of 10% ethanol and 90% linseed oil). Group D was a control in which each mouse was orally administered 3 mg/kg of Prednisolone. Group E was a control in which each mouse was orally administered 20 mg/kg of ibuprofen suspended in 1% methylcellulose (1 mL/kg) (no adjuvant). Group F was the experimental group in which each mouse was administered a pharmaceutical composition disclosed herein (BC1054-20) comprising 20 mg/kg of ibuprofen, 10% ethanol, and 90% linseed oil. Group G was the experimental group in which each mouse was administered a pharmaceutical composition disclosed herein (BC1054-30) comprising 30 mg/kg of ibuprofen, 10% ethanol, and 90% linseed oil. All animals were weighed daily and assessed visually for the presence of diarrhea and/or bloody stool. On day 3 and on day 5 colitis severity was assessed in all animals using video endoscopy, where images were taken and colitis severity scored visually by a blinded observer on a scale from 0 to 4 as follows: 0, normal; 1, loss of vascularity; 2, loss of vascularity and friability; 3, friability and erosions; and 4, ulcerations and bleeding. Following endoscopy on day 5, animals were sacrificed and the colon removed and its length and weight measured. Serum samples were obtained and the colon was fixed in 10% formalin. An additional piece of colon tissue was collected, weighed, and snap frozen in liquid nitrogen.

Results from these experiments are shown in Table 5. Group B (TNBS-treated control group) showed a statistically significant difference in mean weight change when compared to Group A (untreated ethanol control group), all other group comparisons showed no difference in mean weight change. Group B (TNBS-treated control group) showed a statistically significant decrease in mean colon length when compared to Group A (untreated ethanol control group). Additionally, Group D (Prednisolone-treated control group), Group F (BC1054-20-treated experimental group), and Group G (BC1054-30-treated experimental group) all showed a statistically significant increase in mean colon length when compared to Group B (TNBS-treated control group). Although Group B (TNBS-treated control group) showed a statistically significant increase in mean colon weight when compared to Group A (untreated ethanol control group), all other group comparisons showed no difference in mean colon weight. With regards to the endoscopy colitis score, Group D (Prednisolone-treated control group) showed a statistically significant reduced mean colitis scores on both day 3 and day 5 when compared to Group B (TNBS-treated control group). In a similar manner, both Group F (BC1054-20-treated experimental group) and Group G (BC1054-30-treated experimental group) showed a statistically significant reduced mean colitis scores on day 5 when compared to Group B (TNBS-treated control group). These results indicate that a pharmaceutical composition disclosed herein was effective in treating an inflammatory bowel disease.

TABLE 5

Results from Inflammatory Bowel Disease

| Group | Mean Animal Weight | Mean Colon Length | Mean Colon Weight | Endoscopy Colitis Severity Score Day 3 | Day 5 |
|---|---|---|---|---|---|
| A | 23.93 g | 8.5 cm | 215 mg | 0.2 | 0 |
| B | 21.98 g[1] | 7.3 cm[2] | 295 mg[6] | 3.1 | 2.7 |
| C | 23.64 g | 7.8 cm | 239 mg | 2.9 | 2.4 |

TABLE 5-continued

Results from Inflammatory Bowel Disease

| Group | Mean Animal Weight | Mean Colon Length | Mean Colon Weight | Endoscopy Colitis Severity Score Day 3 | Endoscopy Colitis Severity Score Day 5 |
|---|---|---|---|---|---|
| D | 23.33 g | 8.4 cm[3] | 267 mg | 2.3[7] | 1.7[8] |
| E | 23.82 g | 7.9 cm | 267 mg | 2.7 | 2.2 |
| F | 23.69 g | 8.4 cm[4] | 258 mg | 2.6 | 1.9[9] |
| G | 24.25 g | 7.9 cm[5] | 284 mg | 2.4 | 1.4[10] |

[1] Statistically significance difference compared to Group A (p = 0.029).
[2] Statistically significance difference compared to Group A (p = 0.001).
[3] Statistically significance difference compared to Group B (p = 0.001).
[4] Statistically significance difference compared to Group B (p = 0.001).
[5] Statistically significance difference compared to Group B (p = 0.034).
[6] Statistically significance difference compared to Group A (p = 0.009).
[7] Statistically significance difference compared to Group B (p = 0.005).
[8] Statistically significance difference compared to Group B (p = 0.002).
[9] Statistically significance difference compared to Group B (p = 0.045).
[10] Statistically significance difference compared to Group B (p = 0.002).

Example 20 Animal Model for a Systemic Arthritis

To assess the effectiveness of a pharmaceutical composition disclosed herein in treating arthritis, experiments were conducted using an α-collagen antibody induced arthritis (ACAIA) murine model that mimics a systemic arthritis like rheumatoid arthritis.

Male BALB/c mice were divided into eight groups, each containing 10 animals. To induce arthritic symptoms, mice from all eight groups were intravenously injected with 200 μL of an antibody solution comprising a 2 mg cocktail of four α-collagen II monoclonal antibodies (ARTHRITOMAB™, MD Biosciences) on study day 0 (study commencement), followed by a 200 μL intraperitoneal injection of a solution containing 100 μg lipopolysaccharide (LPS) on study day 3. Each group was subjected daily to a control or test treatment administered from day 0-11 as follows: Group 1 mice (1M) were treated orally with a vehicle preparation containing 1% methyl cellulose administered thrice daily; Group 2 mice (2M) were treated intraperitoneally with a positive control preparation containing 10 mg/kg etanercept (ENBREL®, Wyeth) administered once daily; Group 3 mice (3M) were treated orally with a 20 mg/kg test liquid formulation comprising ibuprofen and rapeseed oil (BC1054 LF-RO) administered once daily; Group 4 mice (4M) were treated orally with a 20 mg/kg test liquid formulation comprising ibuprofen and rapeseed oil (BC1054 LF-RO) administered thrice daily; Group 5 mice (5M) were treated orally with a 20 mg/kg test liquid formulation comprising ibuprofen and a glyceryl monolinoleate (MAISINE® 35-1, Gattefosse) (BC1054 LF-MA) administered thrice daily; Group 6 mice (6M) were treated orally with a 20 mg/kg test solid formulation comprising ibuprofen and *theobroma* oil (BC1054 LF-TO) administered thrice daily; Group 7 mice (7M) were treated orally with a control preparation 1 comprising 20 mg/kg of ibuprofen administered thrice daily; and Group 8 mice (8M) were treated orally with a 20 mg/kg test solid formulation comprising ibuprofen and a waxy solid having a melting point of between 37° C. to 41° C. and comprising a mixture of saturated $C_{10}$-$C_{18}$ triglycerides (GELUCIRE® 39/01, Gattefosse) (BC1054 LF-GE) administered thrice daily (Table 6). The dose administered was calculated based on the assumption that each animal weighed, on average, 20 g. A fixed volume of 100 μL was administered to each mouse, except those animals receiving the positive control (2M) were administered 200 μL.

TABLE 6

Constitution of Test Groups and Dose Levels

| Group | Size | Treatment | Dose | Volume | Route | Regime |
|---|---|---|---|---|---|---|
| 1M | 10 | Vehicle | N/A | 5 ml/kg | PO | Thrice daily |
| 2M | 10 | Etanercept | 10 mg/kg | 10 ml/kg | IP | Once daily |
| 3M | 10 | BC1054 LF-RO | 20 mg/kg | 5 ml/kg | PO | Once daily |
| 4M | 10 | BC1054 LF-RO | 20 mg/kg | 5 ml/kg | PO | Thrice daily |
| 5M | 10 | BC1054 LF-MA | 20 mg/kg | 5 ml/kg | PO | Thrice daily |
| 6M | 10 | BC1054 SF-TO | 20 mg/kg | 5 ml/kg | PO | Thrice daily |
| 7M | 10 | Ibuprofen | 20 mg/kg | 5 ml/kg | PO | Thrice daily |
| 8M | 10 | BC1054 SF-GE | 20 mg/kg | 5 ml/kg | PO | Thrice daily |

IP = Intraperitoneal
PO = Per Os
N/A = Not applicable

Arthritic development and clinical examinations were monitored in all mice on study day 0 shortly before arthritis induction and subsequently on study days 3-7, 9, 10 and 12 (study termination). To access arthritic development, both an arthritis score and paw thickness (plethysmography) measurements were obtained. The arthritis score was based on visual assessment of arthritis reactions using a 0-4 scale in ascending order of severity with Grade 0 indicating no arthritis reaction; Grade 1 indicating mild, but definite redness and swelling of the ankle/wrist or apparent redness and swelling limited to individual digits, regardless of the number of affected digits; Grade 2 indicating moderate to severe redness and swelling of the ankle/wrist; Grade 3 indicating redness and swelling of the entire paw including digits; and Grade 4 indicating maximally inflamed limb with involvement of multiple joints. Paw thickness was measured for both hind paws just above the foot pad and below the calcaneum using a dial caliper (Kroeplin, Munich, Germany). Mean values for paw thickness measurements were determined, and where appropriate, analysis of the data by ANOVA with Tukey post hoc analysis was applied to determine significance of treatment effects.

Clinical examinations included changes in body weight, condition of skin, fur, eyes, mucous membranes, occurrence of secretions and excretions (e.g. diarrhea), and autonomic activity (e.g. lacrimation, salivation, piloerection, pupil size, unusual respiratory pattern). Changes in gait, posture and response to handling, as well as the presence of bizarre behavior, tremors, convulsions, sleep and coma were also noted. Serum was collected at study termination.

Arthritis incidence increased in all groups from day 3. In Group 1M animals incidence peaked on day 7 with 9/10 animals showing arthritis reactions which remained relatively constant until the end of the study. In Etanercept-treated Group 2M mice, incidence peaked on day 6 at 9/10 animals showing signs, but had decreased to 1/10 by day 12. The peak incidence of arthritis in Group 3M and Group 4M animals receiving BC1054 LS-RO once or thrice daily was on day 7 (9/10 and 7/10 animals, respectively), and this had decreased to 4/10 mice in both groups by day 12. The arthritis incidence peaked on day 6 in the Group 5M animals receiving BC1054 LS-MA with 8/10 animals affected, and the incidence fluctuated with between 6 and 8 animals scoring until the end of the study. By day 6, 9/10 animals presented with arthritis in Group 6M animals receiving BC1054 SF-TO, but this also fluctuated and ended at 7/10 on day 12. In the Ibuprofen-treated Group 7M, the peak of arthritis incidence was recorded on day 6 with 8/10 animals affected, and this remained relatively constant until the study termination. Group 8M mice receiving a BC1054 LS-GE exhibited peak incidence on day 6 with 9/10 animals presenting with signs of arthritis, but this had decreased to 4/10 by day 12.

Clinical signs associated with LPS-administration developed in all groups following the LPS boost on day 3. These had disappeared in all groups by day 12. No mortalities occurred during this study or significant differences in body weight between the vehicle-treated group and test item-treated groups.

The results of mean paw thickness are given in Table 7. Mean rear paw thickness in Group 1M animals (vehicle-treated) was 1.72±0.01 on day 0. Thickness increased and peaked on day 9 at 2.33±0.15, and ended at 2.17±0.11 on day 12. In Etanercept-treated Group 2M mice, mean rear paw thickness began at 1.70±0.02 on day 0. This increased, peaking at 1.96±0.05 on day 6 before decreasing back to 1.77±0.02 on day 12. Etanercept treatment resulted in significantly decreased paw volume compared to the positive control mice on days 9, 10 and 12. In Group 3M, which received BC1054 LS-RO once daily, rear paw thickness was 1.71±0.02 on day 0. By day 7 the swelling in this group had peaked at 1.96±0.05 where it remained relatively constant thereafter. There were significant reductions in the mean paw swelling on days 6 and 9 following administration of BC1054 LS-RO. The mean rear paw thickness in Group 4M, which received BC1054 LS-RO thrice daily, increased to 1.97±0.08 on day 10 (from 1.70±0.03 on day 0), from day 10 paw volumes remained relative constant till the end of the study. BC1054 LS-RO thrice daily resulted in significantly reduced mean paw thickness compared to vehicle-treated mice (Group 1M) on days 6, 7 and 9. Group 5M mice treated with BC1054 LS-MA had peak paw volume at day 7 (1.97±0.05 from 1.69±0.02 on day 0), this group had significantly reduced measurements on day 6 and day 9 when compared to the vehicle treated Group 1M animals. In Group 6M animals treated with BC1054 LS-TO, mean rear paw thickness began at 1.74±0.01 on day 0. This increased to a peak of 2.05±0.10 on day 7 before decreasing back to 1.94±0.06 on day 12. No significant differences were recorded between BC1054 LS-TO-treated animals (Group 6M) and those treated with vehicle control (Group 1M). In the group which received Ibuprofen (Group 7M), rear paw thickness was 1.71±0.02 on day 0. By day 7 the swelling in this group had peaked at 2.15±0.10 before decreasing to 2.02±0.08 on day 12. No significant differences were observed when this group was compared to the vehicle control Group 1M. Group 8M animals treated with BC1054 LS-GE exhibited a slight increase in rear paw thickness from 1.72±0.02 on day 0 to 1.85±0.06 on day 7, this remained relatively constant finishing at 1.77±0.03 on day 12. Administration of BC1054 LS-GE resulted in significantly reduced paw swelling in animals (Group 8M) compared to vehicle controls (Group 1M) on days 6, 7, 9, 10 and 12.

TABLE 7

Mean Rear Paw Thickness

| Group | N | Treatment | Mean Rear Paw Thickness (mm) | | | | | | | | |
|---|---|---|---|---|---|---|---|---|---|---|---|
| | | | 0 | 3 | 4 | 5 | 6 | 7 | 9 | 10 | 12 |
| 1M | 10 | Vehicle | 1.72 ± 0.01 | 1.72 ± 0.02 | 1.63 ± 0.02 | 1.69 ± 0.02 | 2.03 ± 0.09 | 2.26 ± 0.13 | 2.33 ± 0.15 | 2.32 ± 0.15 | 2.17 ± 0.11 |
| 2M | 10 | Etanercept | 1.70 ± 0.02 | 1.73 ± 0.03 | 1.64 ± 0.02 | 1.63 ± 0.02 | 1.96 ± 0.05 | 1.95 ± 0.04 | 1.88 ± 0.03* | 1.80 ± 0.04* | 1.77 ± 0.02* |
| 3M | 10 | BC1054 LF-RO | 1.71 ± 0.02 | 1.75 ± 0.02 | 1.68 ± 0.02 | 1.71 ± 0.03 | 1.78 ± 0.03* | 1.96 ± 0.05 | 1.91 ± 0.08* | 1.94 ± 0.10 | 1.90 ± 0.08 |
| 4M | 10 | BC1054 LF-RO | 1.70 ± 0.03 | 1.70 ± 0.01 | 1.61 ± 0.02 | 1.65 ± 0.03 | 1.75 ± 0.03* | 1.89 ± 0.07* | 1.91 ± 0.09* | 1.97 ± 0.08 | 1.93 ± 0.07 |
| 5M | 10 | BC1054 LF-MA | 1.69 ± 0.02 | 1.73 ± 0.02 | 1.66 ± 0.02 | 1.67 ± 0.02 | 1.79 ± 0.04* | 1.97 ± 0.05 | 1.92 ± 0.06* | 1.96 ± 0.07 | 1.91 ± 0.06 |
| 6M | 10 | BC1054 SF-TO | 1.74 ± 0.01 | 1.72 ± 0.03 | 1.64 ± 0.01 | 1.70 ± 0.03 | 1.91 ± 0.06 | 2.05 ± 0.10 | 1.96 ± 0.09 | 1.99 ± 0.07 | 1.94 ± 0.06 |
| 7M | 10 | Ibuprofen | 1.71 ± 0.02 | 1.72 ± 0.01 | 1.64 ± 0.02 | 1.71 ± 0.02 | 1.90 ± 0.05 | 2.15 ± 0.10 | 2.08 ± 0.11 | 2.07 ± 0.11 | 2.02 ± 0.08 |
| 8M | 10 | BC1054 SF-GE | 1.72 ± 0.02 | 1.71 ± 0.02 | 1.63 ± 0.01 | 1.67 ± 0.03 | 1.78 ± 0.03* | 1.85 ± 0.06* | 1.73 ± 0.04* | 1.83 ± 0.03* | 1.77 ± 0.03* |

In view of the findings above, significant anti-arthritic activity was observed in Group 3M animals receiving once daily administration of BC1054 LS-RO, Group 4M animals receiving thrice daily administration of BC1054 LS-RO, Group 5M animals receiving thrice daily administration of BC1054 LS-MA, and Group 8M animals receiving thrice daily administration of BC1054SF-GE.

Example 21 Case Studies for the Treatment of Chronic Inflammation

A 47 year old female was diagnosed with reactive arthritis in one knee was treated with a pharmaceutical composition disclosed herein (BC1054) comprising 20 mg/kg of ibuprofen, 10% ethanol, and 90% rapeseed oil (1200 mg uid) over a 3 day period and found that the swelling and pain started to go away after 1 day and was completely better after 3 days. Ineffective standard ibuprofen treatment was subsequently ceased. At a 3 month follow up, no signs of the reactive arthritis have been observed.

A 50 year old male was diagnosed with a chronically inflamed ankle after a maison neuve fracture in the ankle. The patient was taking 30 mg codeine with 500 mg paracetamol bid, along with 10 mg diclofenac tid for 8 months to control pain. He took a 5 day course of a pharmaceutical composition disclosed herein (BC1054) comprising 20 mg/kg of ibuprofen, 10% ethanol, and 90% rapeseed oil (600 mg bid) and after 2 days reported a significant improvement in his pain, and then after 3 days he reported that the pain was completely controlled. He has subsequently ceased the codeine, paracetamol and diclofenac, and after a 2 month follow the patient is still pain free.

A 33 year old female diagnosed with stress related eczema, had an acute flare of moderate eczema on arms and chest. A pharmaceutical composition disclosed herein (BC1054) comprising 20 mg/kg of ibuprofen, 10% ethanol, and 90% rapeseed oil (1200 mg uid) was administered for 7 days. After a couple of hours the lesion ceased itching, after 1 day a noticeable improvement in lesion swelling was reported. 2-3 days later the eczema lesions erythema had resolved and after 7 days the lesions had completely disappeared. In the past the patient had used emollients and hydrocortisone creams, which made the lesions worse and would often lead to a course of antibiotics. The patient commented that her response to the BC1054 treatment was quick and complete, and was a marked improvement on previously pharmacological therapies.

An 85 year old male diagnosed with reactive osteoarthritis, with marked swelling and severe pain in both knee. For 1 year, the patient had been prescribed prednisolone and NSAIDS to control arthritis, with no effect. In addition the patient had taken daily glucosamine. Despite considerable pharmacological intervention, the patient regularly flared resulting in considerable restriction of mobility. The patient was given a 10 day course of a pharmaceutical composition disclosed herein (BC1054) comprising 20 mg/kg of ibuprofen, 10% ethanol, and 90% rapeseed oil (400 mg tid) and experience an appreciable improvement by day 3 and a complete resolution after the completion of the course. The patient reported that his mobility was returned to normal and he has remained in remission at is 1 month examination.

A 38 years old male with reactive osteoarthritis in 1 knee, for 6 months (pain and swelling). Over that period, the patient had tried a comprehensive spectrum of pharmacological therapies: prednisolone, Humira and sulfasalazine, alongside NSAIDs to control pain. Only the sulfasalazine had any appreciable effect, however the patient disliked its side effects, so requested to come off the sulfasalazine. After 2 weeks of being sulfasalazine free, the patient experienced a flare of the reactive arthritis and commenced a 4 day course of a pharmaceutical composition disclosed herein (BC1054) comprising 20 mg/kg of ibuprofen, 10% ethanol, and 90% rapeseed oil (600 mg bid), experiencing complete remission of the arthritis. After 2 weeks of being drug free, the arthritis began to flare again and the patient was put on another 4 day treatment of BC1054, again experiencing complete remission. This time the arthritis flared again 1 week later. To account for this, the patient was given a final 10 day course of BC1054. Subsequently, the arthritis remained in remission for 11 months, as per the last examination.

A 49 year old male diagnosed with hypercholesterolemia (LDL of 4.35 mmol/L) was placed on a pharmaceutical composition disclosed herein (BC1054) comprising 20 mg/kg of ibuprofen, 10% ethanol, and 90% rapeseed oil (600 mg bid) for 7 days. After 5 days of treatment the patient's LDL levels had normalized to 3.89 mmol/L. The normalization of LDL level persisted for 2 months after cessation of BC1054 dosing, as determined at the last examination.

A 60 year old male newly diagnosed with hypercholesterolemia (LDL of 4.31 mmol/L) was given a course of a pharmaceutical composition disclosed herein (BC1054) comprising 20 mg/kg of ibuprofen, 10% ethanol, and 90% rapeseed oil (1200 mg uid) to lower LDL levels to within the normal range. After 5 days of treatment the patients LDL levels were lowered to 3.36 mmol/L. The patient was followed up for 1 month and his LDL remained within the normal range, despite there being no further BC1054 dosing.

Example 22 Treatment of Chronic Inflammation

A 62 year old female complains of joint stiffness and swelling and is diagnosed with rheumatoid arthritis. A physician determines that the joint stiffness and swelling is due to chronic inflammation. The woman is treated by oral administration a pharmaceutical composition comprising ibuprofen as disclosed herein taken twice daily. Alternatively, the woman is treated by oral administration a pharmaceutical composition comprising aspirin as disclosed herein taken thrice daily. Alternatively, the woman is treated by oral administration a pharmaceutical composition comprising naproxen as disclosed herein taken twice daily. The woman's condition is monitored and after about 3 days of treatment the woman indicates there is reduced joint stiffness and swelling. At one and three month check-ups, the woman indicates that she continues to have reduced joint stiffness and swelling in the area treated. This reduction in chronic inflammation symptoms indicates successful treatment with the pharmaceutical composition disclosed herein. A similar type of oral administration of a pharmaceutical composition disclosed herein will be used to treat a patient suffering from chronic inflammation associated with any monoarthritis, oligoarthritis, or polyarthritis, such as, e.g., osteoarthritis, juvenile idiopathic arthritis, septic arthritis, a spondyloarthropathy (including ankylosing spondylitis, reactive arthritis (Reiter's syndrome), psoriatic arthritis, enteropathic arthritis associated with inflammatory bowel disease, Whipple disease or Behcet disease), a synovitis, gout, pseudogout, or Still's disease, as well as, a bursitis, a rheumatic fever, or a tenosynovitis. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 58 year old male complains of breathing difficulty and is diagnosed with chronic obstructive pulmonary disease (COPD). A physician determines that the breathing difficulty is due to chronic inflammation. The man is treated by oral administration a pharmaceutical composition comprising ibuprofen as disclosed herein taken twice daily. Alternatively, the man is treated by oral administration a pharmaceutical composition comprising aspirin as disclosed herein taken thrice daily. Alternatively, the man is treated by oral administration a pharmaceutical composition comprising naproxen as disclosed herein taken twice daily. The man's condition is monitored and after about 3 days of treatment the man indicates there is improvement in his ability to breath. At one and three month check-ups, the man indicates that he continues to have improved breathing. This reduction in a chronic inflammation symptom indicates successful treatment with the pharmaceutical composition disclosed herein. A similar type of oral administration of a pharmaceutical composition disclosed herein will be used to treat a patient suffering from chronic inflammation associated with an asthma, a bronchiolitis, a bronchitis, an emphysema, a laryngitis, a pharyngitis, a pleuritis, a pneumonitis, a rhinitis, a sinusitis, or any other type of chronic respiratory disorder. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 67 year old male complains of muscle soreness and is diagnosed with dermatomyositis. A physician determines that the soreness is due to chronic inflammation. The man is treated by oral administration a pharmaceutical composition comprising ibuprofen as disclosed herein taken twice daily. Alternatively, the man is treated by oral administration a pharmaceutical composition comprising aspirin as disclosed herein taken thrice daily. Alternatively, the man is treated by oral administration a pharmaceutical composition comprising naproxen as disclosed herein taken twice daily. The man's condition is monitored and after about 3 days of treatment the man indicates there is reduced soreness. At one and three month check-ups, the man indicates that he continues to have improved muscle movement and reduced soreness This reduction in a chronic inflammation symptom indicates successful treatment with the pharmaceutical composition disclosed herein. A similar type of oral administration of a pharmaceutical composition disclosed herein will be used to treat a patient suffering from chronic inflammation associated with an inclusion body myositis, a myasthenia gravis, a polymyositis or any other type of inflammatory myopathy, as well as, a fasciitis, a fibrositis, a myositis, a neuromyotonia, a tendinosis, or a tendonitis. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 73 year old female complains of wheezing when she breathes and is diagnosed with Churg-Strauss arteritis. A physician determines that the wheezing is due to chronic inflammation. The woman is treated by oral administration a pharmaceutical composition comprising ibuprofen as disclosed herein taken twice daily. Alternatively, the woman is treated by oral administration a pharmaceutical composition comprising aspirin as disclosed herein taken thrice daily. Alternatively, the woman is treated by oral administration a pharmaceutical composition comprising naproxen as disclosed herein taken twice daily. The woman's condition is monitored and after about 3 days of treatment the woman indicates that she no longer is wheezing. At one and three month check-ups, the woman indicates that she still does not wheeze when she breathes. This reduction in a chronic inflammation symptom indicates successful treatment with the pharmaceutical composition disclosed herein. A similar type of oral administration of a pharmaceutical composition disclosed herein will be used to treat a patient suffering from chronic inflammation associated with any vasculitis, such as, e.g., a Buerger's disease, a cerebral vasculitis, a cryoglobulinemia, an essential cryoglobulinemic vasculitis, a giant cell arteritis, a Golfer's vasculitis, a Henoch-Schonlein purpura, a hypersensitivity vasculitis, a Kawasaki disease, a microscopic polyarteritis/polyangiitis, a polyarteritis *nodosa*, a polymyalgia rheumatica (PMR), a rheumatoid vasculitis, a Takayasu arteritis, or a Wegener's granulomatosis, as well as, an arteritis, a carditis, an endocarditis, a heart disease, high blood pressure, inflammatory cardiomegaly, an ischemic heart disease, a myocarditis, a pericarditis, a phlebitis, a pylephlebitis, or a thrombophlebitis. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 37 year old male complains of skin redness and is diagnosed with rosacea. A physician determines that the redness is due to chronic inflammation. The man is treated by oral administration a pharmaceutical composition comprising ibuprofen as disclosed herein taken twice daily. Alternatively, the man is treated by oral administration a pharmaceutical composition comprising aspirin as disclosed herein taken thrice daily. Alternatively, the man is treated by oral administration a pharmaceutical composition comprising naproxen as disclosed herein taken twice daily. The man's condition is monitored and after about 3 days of treatment the man indicates there is reduced skin redness. At one and three month check-ups, the man indicates that he continues to have improved skin tone and reduced redness This reduction in a chronic inflammation symptom indicates successful treatment with the pharmaceutical composition disclosed herein. A similar type of oral administration of a pharmaceutical composition disclosed herein will be used to treat a patient suffering from chronic inflammation associated with an acne, a cervicitis, a dermatitis, an eczema (including an atopic eczema, a contact eczema, a xerotic eczema, a seborrhoeic dermatitis, a dyshidrosis, a discoid eczema, a venous eczema, a dermatitis herpetiformis, a neurodermatitis, or an autoeczematization), an endometritis, a gingivitis, a glossitis, a hidradenitis suppurativa, a keratitis, a keratoconjunctivitis, a mastitis, a psoriasis (including a plaqure psoriasis, a nail psoriasis, a guttate psoriasis, a scalp psoriasis, an inverse psoriasis, a pustular psoriasis, or an erythrodermis psoriasis), a scleroderma, a statis dermatitis, a stomatitis, a tonsillitis, a vaginitis, a vitiligo, or a vulvitis. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 33 year old female complains of abdominal pain and diarrhea and is diagnosed with Crohn's disease. A physician determines that the abdominal pain and diarrhea is due to chronic inflammation. The woman is treated by oral administration a pharmaceutical composition comprising ibuprofen as disclosed herein taken twice daily. Alternatively, the woman is treated by oral administration a pharmaceutical composition comprising aspirin as disclosed herein taken thrice daily. Alternatively, the woman is treated by oral administration a pharmaceutical composition comprising naproxen as disclosed herein taken twice daily. The woman's condition is monitored and after about 3 days of treatment the woman indicates that there is a reduction in abdominal pain and she no longer has diarrhea. At one and three month check-ups, the woman indicates that she continues to have reduced abdominal pain and diarrhea. This reduction in a chronic inflammation symptom indicates successful treatment with the pharmaceutical composition disclosed herein. A similar type of oral administration of a pharmaceutical composition disclosed herein will be used to treat a patient suffering from neurogenic inflammation associated with any inflammatory bowel disease, such as, e.g., an ulcerative colitis (including ulcerative proctitis, left-sided colitis, pancolitis and fulminant colitis), any irritable bowel disease, as well as, a colitis, an enteritis, an enterocolitis, a gastritis, a gastroenteritis, a metabolic syndrome (syndrome X), a spastic colon, or any other gastrointestinal disorder. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 46 year old male complains of fever, joint pains, and fatigue and is diagnosed with systemic lupus erythematosus. A physician determines that these symptoms are due to chronic inflammation. The man is treated by oral administration a pharmaceutical composition comprising ibuprofen as disclosed herein taken twice daily. Alternatively, the man is treated by oral administration a pharmaceutical composition comprising aspirin as disclosed herein taken thrice daily. Alternatively, the man is treated by oral administration a pharmaceutical composition comprising naproxen as disclosed herein taken twice daily. The man's condition is monitored and after about 3 days of treatment the man indicates there is improvement in his health, his fever is gone, the pain in his joints is reduced and his is not as tired. At one and three month check-ups, the man indicates that he continues to have reduced joint pain and does not suffer from fevers or fatigue. This reduction in a chronic inflammation symptom indicates successful treatment with the pharmaceutical composition disclosed herein. A similar type of oral administration of a pharmaceutical composition disclosed herein will be used to treat a patient suffering from chronic inflammation associated with any other systemic autoimmune disorder, including, without limitation, an anti-phospholipid antibody syndrome (APS), a bullous pemphigoid, a Chagas disease, a discoid lupus erythematosus, a drug-induced lupus erythematosus, a Goodpasture's syndrome, a Guillain-Barre syndrome, an idiopathic thrombocytopenic purpura, a myasthenia gravis, a neonatal lupus, a pernicious anemia, a polymyalgia rheumatica, a rheumatoid arthritis, a scleroderma, a Sjögren's syndrome, a subacute cutaneous lupus erythematosus, or a Wegener's granulomatosis. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 58 year old male complains of depression, sensitivity to cold, weight gain, forgetfulness, and constipation and is diagnosed with Hashimoto's thyroiditis. A physician determines that these symptoms are due to chronic inflammation. The man is treated by oral administration a pharmaceutical composition comprising ibuprofen as disclosed herein taken twice daily. Alternatively, the man is treated by oral administration a pharmaceutical composition comprising aspirin as disclosed herein taken thrice daily. Alternatively, the man is treated by oral administration a pharmaceutical composition comprising naproxen as disclosed herein taken twice daily. The man's condition is monitored and after about 3 days of treatment the man indicates there is reduction in all the symptoms complained of. At one and three month check-ups, the man indicates that he still does not experience depression, sensitivity to cold, weight gain, forgetfulness, and constipation. This reduction in a chronic inflammation symptom indicates successful treatment with the pharmaceutical composition disclosed herein. A similar type of oral administration of a pharmaceutical composition disclosed herein will be used to treat a patient suffering from chronic inflammation associated with any other local autoimmune disorder, including, without limitation, an acute disseminated encephalomyelitis (ADEM), an Addison's disease, an autoimmune hemolytic anemia, an autoimmune hepatitis (including primary biliary cirrhosis), an autoimmune inner ear disease, a celiac disease, a Crohn's disease, a diabetes mellitus type 1, an endometriosis, a giant cell arteritis, a Graves' disease, an interstitial cystitis, a lupus nephritis, a multiple sclerosis, a morphea, a pemphigus vulgaris, a recurrent disseminated encephalomyelitis, a sclerosing cholangitis, an ulcerative colitis, or a vitiligo. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

A 59 year old female complains of joint stiffness and swelling and is diagnosed with reactive arthritis. A physician determines that the joint stiffness and swelling is due to chronic inflammation. The woman is treated by oral administration a pharmaceutical composition comprising ibuprofen as disclosed herein taken twice daily. Alternatively, the woman is treated by oral administration a pharmaceutical composition comprising aspirin as disclosed herein taken thrice daily. Alternatively, the woman is treated by oral administration a pharmaceutical composition comprising naproxen as disclosed herein taken twice daily. The woman's condition is monitored and after about 3 days of treatment the woman indicates there is reduced joint stiffness and swelling. At one and three month check-ups, the woman indicates that she continues to have reduced joint stiffness and swelling in the area treated. This reduction in a chronic inflammation symptom indicates successful treatment with the pharmaceutical composition disclosed herein. A similar type of oral administration of a pharmaceutical composition disclosed herein will be used to treat a patient suffering from chronic inflammation associated with any monoarthritis, oligoarthritis, or polyarthritis, such as, e.g., osteoarthritis, juvenile idiopathic arthritis, septic arthritis, a spondyloarthropathy (including ankylosing spondylitis, reactive arthritis (Reiter's syndrome), psoriatic arthritis, enteropathic arthritis associated with inflammatory bowel disease, Whipple disease or Behcet disease), a synovitis, gout, pseudogout, or Still's disease, as well as, a bursitis, a rheumatic fever, or a tenosynovitis. In a similar manner, any of the therapeutic compounds such as, e.g., a salicylate derivative NSAID, a p-amino phenol derivative NSAID, a propionic acid derivative NSAID, an acetic acid derivative NSAID, an enolic acid derivative NSAID, a fenamic acid derivative NSAID, a non-selective cyclo-oxygenase (COX) inhibitor, a selective cyclooxygenase 1 (COX 1) inhibitor, a selective cyclooxygenase 2 (COX 2) inhibitor, or a fibrate, will be formulated into a pharmaceutical composition and administered to the patient as described above.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The invention claimed is:

1. A solid solution pharmaceutical composition comprising:
   a) one or more propionic acid derived non-steroidal anti-inflammatory drugs (NSAIDs) in an amount of about 15% to about 40% by weight of the pharmaceutical composition;
   b) one or more pharmaceutically-acceptable hard fats comprising one or more glycerolipids, the one or more pharmaceutically-acceptable hard fats in an amount of at least 30% by weight of the pharmaceutical composition;
   c) one or more pharmaceutically-acceptable liquid lipids comprising one or more monoglycerides, the one or more pharmaceutically-acceptable liquid lipids in an amount of less than 45% by weight of the pharmaceutical composition, and wherein the solid solution pharmaceutical composition is formulated to have a melting point temperature of about 25° C. or higher.

2. The solid solution pharmaceutical composition according to claim 1, wherein the amount of the one or more propionic acid derivative NSAIDS is about 20% to about 40% by weight of the pharmaceutical composition.

3. The solid solution pharmaceutical composition according to claim 1, wherein the amount of the one or more propionic acid derivative NSAIDS is at about 15% to about 35% by weight of the pharmaceutical composition.

4. The solid solution pharmaceutical composition according to claim 3, wherein the amount of the one or more propionic acid derivative NSAIDS is at about 20% to about 30% by weight of the pharmaceutical composition.

5. The solid solution pharmaceutical composition according to claim 1, wherein the one or more propionic acid derived NSAID comprises an Alminoprofen, a Benoxaprofen, a Dexketoprofen, a Fenoprofen, a Flurbiprofen, an Ibuprofen, an Indoprofen, a Ketoprofen, a Loxoprofen, a Naproxen, an Oxaprozin, a Pranoprofen, or a Suprofen.

6. The solid solution pharmaceutical composition according to claim 5, wherein the one or more propionic acid derived NSAID is an ibuprofen.

7. The solid solution pharmaceutical composition according to claim 1, wherein the amount of the one or more pharmaceutically-acceptable hard fats is at least 35% by weight of the pharmaceutical composition.

8. The solid solution pharmaceutical composition according to claim 1, wherein the amount of the one or more pharmaceutically-acceptable hard fats is about 35% to about 45% by weight of the pharmaceutical composition.

9. The solid solution pharmaceutical composition according to claim 1, wherein the one or more pharmaceutically-acceptable hard fats have a melting point of about 40° C. to about 50° C.

10. The solid solution pharmaceutical composition according to claim 1, wherein the one or more glycerolipids comprise a triglyceride with one saturated or unsaturated fatty acid having a carbon length of $C_{12}$-$C_{24}$, two saturated or unsaturated fatty acids each having a carbon length of $C_{12}$-$C_{24}$, or three saturated or unsaturated fatty acids each having a carbon length of $C_{12}$-$C_{24}$.

11. The solid solution pharmaceutical composition according to claim 10, wherein the one or more glycerolipids comprise a mixture of saturated $C_{10}$-$C_{18}$ triglycerides having a melting point range of about 41° C. to 45° C.

12. The solid solution pharmaceutical composition according to claim 1, wherein the amount of the one or more pharmaceutically-acceptable liquid lipids is less than 40% by weight of the pharmaceutical composition.

13. The solid solution pharmaceutical composition according to claim 1, wherein the amount of the one or more pharmaceutically-acceptable liquid lipids is about 8% to about 40% by weight of the pharmaceutical composition.

14. The solid solution pharmaceutical composition according to claim 13, wherein the amount of the one or more pharmaceutically-acceptable liquid lipids is about 8% to about 30% by weight of the pharmaceutical composition.

15. The solid solution pharmaceutical composition according to claim 1, wherein the one or more monoglycerides comprises glycerol monomyristoleate, glycerol monopalmitoleate, glycerol monosapienate, glycerol monooleate, glycerol monoelaidate, glycerol monovaccenate, glycerol monolinoleate, glycerol monolinoelaidate, glycerol monolinolenate, glycerol monostearidonate, glycerol monoeicosenoate, glycerol monomeadate, glycerol monoarachidonate, glycerol monoeicosapentaenoate, glycerol monoerucate, glycerol monodocosahexaenoate, or glycerol mononervonate.

16. The solid solution pharmaceutical composition according to claim 15, wherein the one or more monoglycerides is glycerol monolinoleate.

17. The solid solution pharmaceutical composition according to claim 1, wherein the one or more pharmaceutically-acceptable liquid lipids further comprises one or more diglycerides, one or more triglycerides, or a combination thereof.

18. The solid solution pharmaceutical composition according to claim 1, wherein the amount of the one or more propionic acid derived NSAIDs is about 25% to about 35% by weight of the pharmaceutical composition, wherein the amount of the one or more pharmaceutically-acceptable hard fats is about 35% to about 45% by weight of the pharmaceutical composition, and wherein the amount of the one or more pharmaceutically-acceptable liquid lipids is about 8% to about 30% by weight of the pharmaceutical composition.

19. The solid solution pharmaceutical composition according to claim 18, wherein the one or more propionic acid derived NSAID is an ibuprofen, wherein the one or more pharmaceutically-acceptable glycerolipids includes one or more glycerolipids comprising a mixture of saturated $C_{10}$-$C_{18}$ triglycerides having a melting point range of about 41° C. to 45° C., and wherein the one or more monoglycerides includes glycerol monolinoleate.

20. The solid solution pharmaceutical composition according to claim 1, further comprising one or more liquid polyethylene glycol (PEG) polymer in an amount of about 5% to about 18% by weight of the pharmaceutical composition.

21. The solid solution pharmaceutical composition according to claim 20, wherein the one or more liquid PEG polymer in an amount of about 7% to about 15% by weight of the pharmaceutical composition.

22. The solid solution pharmaceutical composition according to claim 21, wherein the one or more liquid PEG polymer in an amount of about 9% to about 12% by weight of the pharmaceutical composition.

23. The solid solution pharmaceutical composition according to claim 20, wherein the amount of the one or more propionic acid derived NSAIDs is about 25% to about 35% by weight of the pharmaceutical composition, wherein the amount of the one or more pharmaceutically-acceptable hard fats is about 35% to about 45% by weight of the pharmaceutical composition, wherein the amount of the one or more pharmaceutically-acceptable liquid lipids is about 8% to about 30% by weight of the pharmaceutical composition, and wherein the one or more liquid PEG polymer is about 9% to about 12% by weight of the pharmaceutical composition.

24. The solid solution pharmaceutical composition according to claim 23, wherein the one or more propionic acid derived NSAID is an ibuprofen, wherein the one or more pharmaceutically-acceptable glycerolipids includes one or more glycerolipids comprising a mixture of saturated $C_{10}$-$C_{18}$ triglycerides having a melting point range of about 41° C. to 45° C., wherein the one or more monoglycerides includes glycerol monolinoleate, and wherein the liquid PEG polymer is a PEG 100, PEG 200, PEG 300, PEG 400, PEG 500, PEG 600, or any combination thereof.

25. A solid solution pharmaceutical composition comprising:

a) one or more propionic acid derived non-steroidal anti-inflammatory drugs (NSAIDs) in an amount of about 25% to about 35% by weight of the pharmaceutical composition;
b) one or more pharmaceutically-acceptable hard fats comprising one or more glycerolipids, the one or more pharmaceutically-acceptable hard fats in an amount of about 35% to about 45% by weight of the pharmaceutical composition;
c) one or more pharmaceutically-acceptable liquid lipids comprising one or more monoglycerides, the one or more pharmaceutically-acceptable liquid lipids in an amount of about 8% to about 30% by weight of the pharmaceutical composition, and
d) one or more liquid polyethylene glycol (PEG) polymers in an amount of about 9% to about 12% by weight of the pharmaceutical composition;

wherein the solid solution pharmaceutical composition is formulated to have a melting point temperature of about 25° C. or higher.

26. A solid solution pharmaceutical composition comprising:
a) an ibuprofen in an amount of about 25% to about 35% by weight of the pharmaceutical composition;
b) one or more pharmaceutically-acceptable hard fats comprising one or more glycerolipids, the one or more pharmaceutically-acceptable hard fats in an amount of about 35% to about 45% by weight of the pharmaceutical composition;
c) one or more pharmaceutically-acceptable liquid lipids comprising one or more monoglycerides, the one or more pharmaceutically-acceptable liquid lipids in an amount of about 8% to about 30% by weight of the pharmaceutical composition; and
d) one or more liquid polyethylene glycol (PEG) polymers in an amount of about 9% to about 12% by weight of the pharmaceutical composition;

wherein the solid solution pharmaceutical composition is formulated to have a melting point temperature of about 25° C. or higher.

* * * * *